US007547817B2

(12) United States Patent
Green et al.

(10) Patent No.: US 7,547,817 B2
(45) Date of Patent: Jun. 16, 2009

(54) TRANSGENIC ANIMALS FOR PRODUCING SPECIFIC ISOTYPES OF HUMAN ANTIBODIES VIA NON-COGNATE SWITCH REGIONS

(75) Inventors: Larry L Green, San Francisco, CA (US); Vladimir E Ivanov, Fremont, CA (US); Geoffrey C Davis, Burlingame, CA (US)

(73) Assignee: Amgen Fremont Inc., South San Francisco, CA (US)

( * ) Notice: Subject to any disclaimer, the term of this patent is extended or adjusted under 35 U.S.C. 154(b) by 323 days.

(21) Appl. No.: 11/223,359

(22) Filed: Sep. 9, 2005

(65) Prior Publication Data

US 2006/0134780 A1 Jun. 22, 2006

Related U.S. Application Data

(63) Continuation of application No. 09/999,321, filed on Nov. 30, 2001, now Pat. No. 7,049,426, which is a continuation of application No. PCT/US00/15782, filed on Jun. 8, 2000, and a continuation-in-part of application No. 09/329,582, filed on Jun. 10, 1999, now Pat. No. 6,833,268.

(51) Int. Cl.
*A01K 67/00* (2006.01)
*A01K 67/027* (2006.01)
*C12N 15/00* (2006.01)
*C12P 21/00* (2006.01)

(52) U.S. Cl. .................. 800/18; 800/13; 800/21; 800/6

(58) Field of Classification Search .................. 800/18, 800/13, 21, 6
See application file for complete search history.

(56) References Cited

U.S. PATENT DOCUMENTS

| 5,569,825 A | * | 10/1996 | Lonberg et al. | ............... 800/18 |
| 5,625,126 A | * | 4/1997 | Lonberg et al. | ............... 800/18 |
| 5,877,397 A | | 3/1999 | Lonberg et al. | |

FOREIGN PATENT DOCUMENTS

| WO | WO 94/02602 | 2/1994 |
| WO | WO 96/30498 | 10/1996 |
| WO | WO 98/24884 | 6/1998 |
| WO | WO 98/24893 | 6/1998 |

OTHER PUBLICATIONS

Campbell et al. (1997) Theriogenology, vol. 47, 63-72.*
Bulter et al. (1998) Revue Scientifique et Technique Office International Des Epizooties. vol. 17, No. 1, pp. 43-70.*
V. Arulampalam et al., "Elevated Expression Levels of an Ig Transgene in Mice Links the IgH 3' Enhancer to the Regulation of IgH Expression," *International Immunology*, 8:1149-11 57 (1996).
V. Arulampalam et al., "The Enhancer Shift: A Model to Explain the Developmental Control of IgH Gene Expression in B-lineage Cells," *Immunology Today*, 18:549-554 (1997).
F.D. Batista et al., "Affinity Dependence of the B Cell Response to Antigen: A Threshold, a Ceiling, and the Importance of Off-Rate," *Immunity*, 8:751-759 (1998).
A.G. Betz et al., "Discriminating Intrinsic and Antigen-selected Mutational hotspots in Immunoglobulin V Genes," *Immunology Today*, 14:405-409 (1993).
A.G. Betz et al., "Elements Regulating Somatic Hypermutation of an Immunoglobulin κ Gene: Critical Role for the Intron Enhancer/Matrix Attachment Region," *Cell*, 77:239-248 (1994).
C.I. Bindon et al., "Human Monoclonal IgG Isotypes Differ in Complement Activating Function at the Level of C4 as Well AS C1q," *J. Exp. Med.*, 168:127-142 (1988).
S. Biocca et al., "Expression and Targeting of Intracellular Antibodies in Mammalian Cells," *The EMBO Journal*, 9:101-108 (1990).
J.B. Bolen, "Protein Tyrosine Kinases in the Initiation of Antigen Receptor Signaling," *Current Opinion in Immunology*, 7:306-311 (1995).
A. Bottaro et al., "S Region Transcription per se Promotes Basal IgE Class Switch Recombination But Additional Factors Regulate the Efficiency of the Process," *The EMBO Journal* 13:665-674 (1994).
M. Brüggemann et al., "Production of Human Antibody Repertoires in Transgenic Mice," *Current Opinion in Biotechnology*, 8:455-458 (1997).
M. Brüggemann et al., "Strategies for Expressing; Human Antibody Repertoires in Transgenic Mice," *Immunology Today*, 17:391-397 (1996).
M. Brüggemann et al., "Designer Mice: The Production of Human Antibody Repertoires in Transgenic Animals," *Generation of Antibodies by Cell and Gene Immortalization*, 7:33-40 (1993)
M. Brüggemann et al., "Human Antibody Production in Transgenic Mice: Expression from 100 kb of the Human IgH Locus, " *Eur. J. Immunol.*, 21:1323-1326 (1991).

(Continued)

*Primary Examiner*—Anne Marie S Wehbe
(74) *Attorney, Agent, or Firm*—Ropes & Gray LLP

(57) ABSTRACT

The present invention provides fully human antibodies in a transgenic animal of a desired isotype in response to immunization with any virtually any desired antigen. The human immunoglobulin heavy chain transgene in the foregoing animals comprises a human constant region gene segment comprising exons encoding the desired heavy chain isotype, operably linked to switch segments from a constant region of a different heavy chain isotype, i.e., a non-cognate switch region. Said additional constant region segment comprises a switch region and human constant region coding segment, wherein the constant region coding segment is operably linked to a switch region that it is not normally associated with, i.e., a non-cognate switch region. In the transgenes of the invention, the non-cognate switch region may be a switch region from a different species than the constant region coding segment. The switch region and membrane exons of the invention may comprise a human gamma-2 constant region and the secreted constant region exons are from a human gamma-1 or a human gamma-4 constant region.

26 Claims, 8 Drawing Sheets

OTHER PUBLICATIONS

M. Brüggemann et al., "Construction, Function and Immunogenicity of Recombinant Monoclonal Antibodies," *Behring, Inst. Mitt.*, 87:21-24 (1990).

M. Brüggemann et al., "A Repertoire of Monoclonal Antibodies with Huamn Heavy Chains from Transgenic Mice," *Proc. Natl. Acad. Sci. USA*, 86:6709-6713 (1989).

M. Brüggemann et al., "The Immunogenicity of Chimeric Antibodies," *J. Exp. Med.*, 170:2153-2157 (1989).

M. Brüggemann, "Evolution of the Rat Immunoglobulin Gamma Heavy-chain Gene Family," *Gene*, 74:473-482 (1988).

M. Brüggemann et al., "Novel Antibodies bv DNA Manipulation", *Monoclonal Antibody Therapy*. 45:91-105 (1988).

M. Brüggemann et al., "Sequence of a Rat Immunoglobulin $Y_{2c}$ Heavy Chain Constant Region cDNA: Extensive Homology to Mouse $Y_3$," *Eur. J. Immunol.*, 18:317-319 (1988).

M. Brüggemann et al., "Comparison of the Effector Functions of Human Immunoglobulins Using a Matched Set of Chimeric Antibodies," *J.Exp. Med.* 166:1351-1361 (1987).

C. Bützler et al., "Rapid Induction of B-cell Lymphomas in Mice Carrying a Human IgH/c-*myc*YAC," *Oncogene*, 14:1383-1388 (1997).

A. Cattaneo et al., "Polymeric Immunoglobulin M is Secreted by Transfectants of Non-lymphoid Cells in the Absence of Immunoglobulin J Chain", *EMBO Jour.*, 6:2753-2758 (1987).

J. Chen et al., "Mutations of the Intronic IgH and its Flanking Sequences Differentially Affect Accessibility of the $J_H$ Locus," *The EMBO Journal*, 12:4635-4645 (1993).

T.K. Choi et al., "Transgenic Mice Containing a Human Heavy Chain Immunoglobulin Gene Fragment Cloned in a Yeast Artificial Chromosome," *Nature Genetics*, 4:117-123 (1993).

M. Cogné et al., "A Class Switch Control Region at the 3' End of the Immunoglobulin Heavy Chain Locus," *Cell*, 77:737-747 (1994).

G.P. Cook et al., "Regulated Activity of the IgH Intron Enhancer (Eμ) in the T Lymphocyte Lineage," *International Immunology*, 7:89-95 (1995).

P. Dariavach et al., "The Mouse IgH 3' -Enhancer," *Eur. J. Immunol.*, 21:1499-1504 (1991).

N.P. Davies et al., "Extension of Yeast Artificial Chromosomes by Cosmid Multimers," *Nucleic Acids Research*, 21:767-768 (1993).

N.P. Davies et al., "Creation of Mice Expressing Human Antibody Light Chains by Introduction of a Yeast Artificial Chromosome Containing the Core Region of the Human Immunoglobulin κ Locus," *Bio/Technology*, 11:911-914 (1993).

N.P. Davies et al., "Targeted Alterations in Yeast Artificial Chromosomes for Inter-species Gene Transfer," *Nucleic Acids Research*, 20:2693-2698 (1992).

A.L. DeFranco, "The Complexity of Signaling Pathways Activated by the BCR," *Current Opinion in Immunology*, 9:296-308 (1997).

S. Delphin et al., "Characterization of an Interleukin 4(IL-4) Responsive Region in the Immunoglobulin Heavy Chain Germline e Promoter; Regulation by NF-IL-4, a C/EBP Family Member and NF-KB/p50," *J. Exp. Med.*, 181:181-192 (1995).

J. Durdik et al., "Isotype Switching by a Microinjected μ Immunoglobulin Heavy Chain Gene in Transgenic Mice", *Proc. Natl. Acad. Sci. USA*, 86:2346-2350 (1989).

M. R. Ehrenstein et al., "Targeted Gene Disruption Reveals a Role For Natural Secretory IgM in the Maturation of the Primary Immune Response," *Proc. Natl. Acad. Sci. USA*, 95:10089-10093 (1998).

J. Ellison et al., "Linkage and Sequence Homology of Two Human Immunoglobulin Y Heavy Chain Constant Region Genes," *Proc. Natl. Acad. Sci. USA*, 79:1984-1988 (1982).

J.W. Ellison et al., "Nucleotide Sequence of a Human Immunoglobulin $CY_1$ Gene, " *Nucleic Acids Research*, 10:4071-4079 (1982).

J. Ellison et al., "Nucleotide Sequence of a Human Immunoglobulin $CY_4$ Gene," *DNA*, 1: 11-18 (1981).

D.M. Fishwild et al., "High-avidity Human IgGK Monoclonal Antibodies from a Novel Strain of Minilocus Transgenic Mice," *Nature Biotechnology*, 14:845-851 (1996).

B. Goyenechea et al., "Cells Strongly Expressing IgK Transgenes Show Clonal Recruitment of Hypermutation: A Role for Both MAR and the Enhancers," *The EMBO Journal*, 16:3987-3994 (1997).

L. Green et al., "Regulation of B Cell Development by Variable Gene Complexity in Mice Reconstituted with Human Immunoglobulin Yeast Artificial Chromosomes," *J. Exp. Med.*, 188, pp. 483-495 (1998).

I.J. Harmer et al., "Chimaeric Monoclonal Antibodies Encoded by the Human $V_H26$ Gene from Naïve Transgenic Mice Display a Wide Range of Antigen-binding Specificities," *Immunology*, 88;174-182 (1996).

H. Hayashida et al., "Concerted Evolution of the Mouse Immunoglobulin Gamma Chain Genes," *The EMBO Journal*, 3:2047-2053 (1984).

T. Honjo et al., "Constant-Region Genes of the Immunoglobulin Heavy Chain and the Molecular Mechanism of Class Switching," *Immunoglobulin Genes*, 123-149 (1989), Academy Press.

M.T.F. Huang, "Gene Targeting Technology for Creating Transgenic Models of Lymphopoiesis," *Laboratory Animal Science*, 43:156-159 (1993).

M.T.F. Huang, "T Cell Development in CD3-ç Mutant Mice," *Intern. Rev. Immunol.*, 13:29-41 (1995).

S. Huck et al., "Sequence of a Huamn Immunoglobulin Gamma 3 Heavy Chain Constant Region Gene: Comparison With the Other Human CY Genes," *Nucleic Acids Research*, 14:1779-1789 (1986).

A. Jakobovits et al., "Analysis og Homozygous Mutant Chimeric Mice: Deletion of the Immunoglobulin Heavy-chain Joining Region Blocks B-Cell Development and Antibody Production," *Proc. Natl. Acad. Sci. USA*, 90:2551-2555 (1993).

A. Jakobovits, "The Long-Awaited Magic Bullets: Therapeutic Human Monoclonal Antibodies From Transgenic Mice," *Exp. Opin. Invest. Drugs*, 7:607-614 (1998).

C.J. Jolly et al., "The Targeting of Somatic Hypermutation," *Seminars in Immunology*, 8:159-168 (1996).

C.J. Jolly et al., "Rapid Methods for the Analysis of Immunoglobin Gene Hvpermutation: Application to Transgenic and Gene Targeted Mice", *Nuceleic Acids Research*, 25:1913-1919 (1997).

P.T. Jones et al., "Replacing The Complementarity-determining Regions in a Human Antibody with Those From a Mouse" *Nature*, 321:522-525 (1986).

S. Jung et al., "Shutdown of Class Switch Recombination by Deletion of a Switch Region Control Element," *Science*, 259: 984-987 (1993).

N. Klix et al., "Multiple Sequences from Downstream of the Jχ Cluster Can Combine to Recruit Somatic Hypermutation to a Heterologous, Upstream Mutation Domain," *Eur. J. Immunol.*, 28:317-326 (1998).

T. Kurosaki, "Molecular Mechanisms in B Cell Antigen Receptor Signaling," *Current Opinion in Immunology*, 9:309-318 (1997).

K. Kuze et al., "Characterization of the Enhancer Region for Germline Transcription of the Gamma 3 Constant Region Gene of Human Immunoglobulin," *International Immunology*, 3:647-655 (1991).

S.C. Li et al., "Expression of 1 μ-Cy Hybrid Germline Transcripts Subsequent to Immunoglobulin Heavy Chain Class Switching," *International Immunology*, 6:491-497 (1994).

R. Lieberson et al., "An Enhancer at the 3' End of the Mouse Immunoglobulin Heavy Chain Locus," *Nucleic Acids Research*, 19:933-937 (1991).

Y. Liu et al., "Gene-targeted B-deficient Mice Reveal a Critical Role for B Cells in the CD4 T Cell Response," *International Immunology*, 7:1353-1362 (1995).

N. Lonberg et al., "Antigen-specific Human Antibodies from Mice Comprising Four Distinct Genetic Modifications," *Nature*, 368:856-859 (1994).

N. Lonberg et al., "Human Antibodies from Transgenic Mice," *Intern. Rev. Immunol.*, 13:65-93 (1995).

J.F. Lorina et al., "Rational Design of an Animal Model for Alzheimer's Disease: Introduction of Multiple Human Genomic Transgenes to Reproduce AD Pathology in a Rodent," *Neurobiology of Aging*, 17:173-182 (1996).

J.J. MacQuitty, "GenPharm's Knockout Mice," *Science*, 257:1188 (1992).

J.J. MacQuitty, "The Real Implications of Dolly," *Nature Biotechnology*, 15:294 (1997).

J.P. Manis et al., "Class Switching in B Cells Lacking 3' Immunoglobulin Heavy Chain Enhancers", *J. Exp. Med.*, 188:1421-1431 (1998).

J.O. Mason et al., "Transcription Cell Type Specificity Is Conferred by an Immunoglobulin $V_H$ Gene Promoter That Includes a Functional Consensus Sequence," *Cell*, 41:479-487 (1985).

P. Matthias et al., "The Immunoglobulin Heavy Chain Locus Contains Another B-Cell-Specific 3' Enhancer Close to the α Constant Region," *Molecular and Cellular Biology*, 13:1547-1553 (1993).

M.J. Mendez et al., "Functional Transplant of Megabase Human Immunoglobin Loci Recapitulates Human Antibody Response in Mice", *Nature Genetics*, 15:146-156 (1997).

K.B. Meyer et al., "The IgK 3' -Enhancer Triggers Gene Expression in Early B Lymphocytes but Its Activity in Enhanced on B cell Activation," *International Immunology*, 8:1561-1568 (1996).

K.B. Meyer et al., "The Importance of the 3' -Enhancer Region in Immunoglobulin χ Gene Expression," *Nucleic Acids Research*, 18:5609-5615 (1990).

K.B. Meyer et al., "The Immunoglobulin χ Locus Contains a Second, Stronger B-cell-specific Enhancer Which is Located Downstream of the Constant Region," *The EMBO Journal*, 8:1959-1964 (1989).

J.S. Michaelson et al., "Regulation of 3' IgH Enhancers by a Common Set of Factors, Including KB-Binding Proteins," *The Journal of Immunology*, 156:2828-2839 (1996).

J.S. Michaelson et al., "Identification of 3' α-hs4, a Novel Ig Heavy Chain Enhancer Element Regulated at Multiple Stages of B Cell Differentiation," *Nucleic Acids Research*, 23:975-981 (1995).

F.C. Mills et al., "Human IgSγ Regions and Their Participation in Sequential Switching to IgE," *The Journal of Immunology*, 155:3021-3036 (1995).

F.C. Mills et al., "Sequences of Human Immunoglobulin Switch Regions: Implications for Recombination and Transcription," *Nucleic Acids Research*, 18:73Q5-7316 (1990).

C. Milstein et al., "Both DNA Strands of Antibody Genes are Hypermutation Targets," *Proc. Natl. Acad. Sci. USA*, 95:8791-8794 (1998).

R. Mocikat et al., "The effect of the Rat Immunoglobulin Heavy-chain 3' Enhancer is position Dependent," *Gene*, 136:349-353 (1993).

M.R. Mowatt et al., "DNA Sequence of the Murine γ1 Switch Segment Reveals Novel Structural Elements," *J. Immunology*, 136, pp. 2674-2683 (1986).

M.S. Neuberger, "Antigen Receptor Signaling Gives Lymphocytes a Long Life," *Cell*, 90:971-973 (1997).

M. Neuberger et al., "Mice Perform a Human Repertoire," *Nature*, 386:25-26 (1997).

M.S. Neuberger et al., "Activation of Mouse Complement by Monoclonal Mouse Antibodies," *Eur. J. Immunol.*, 11:1012-1016 (1981).

M.S. Neuberger et al., " Isotype Exclusion and Transgene Down-regulation in Immunoglobulin-λ Transgenic Mice,"*Nature*, 338:350-352 (1989).

M.S. Neuberger et al., "Recombinant Antibodies Possessing Novel Effector Functions," *Nature*, 312:604-608 (1984).

L. O'Rourke et al., "Co-receptors of B Lymphocytes,"*Current Opinion in Immunology*, 9:324-329 (1997).

Q. Pan et al., "Characterization of Human γ4 Switch Region Polymorphisms Suggests a Meiotic Recombinational Hot Spot Within the Ig Locus: Influnece of S Region Length on IgG4 Production," *The Journal of Immunology*, 161:3520-3526 (1998).

K.J. Patel et al., "Antigen Presentation by the B Cell Antigen Receptor Is Driven by the α/β Sheath and Occurs Independently of Its Cytoplasmic Tyrosines," *Cell*, 74:939-946 (1993).

B.E. Pearson et al., "Expression of the Human β-amyloid Precursor Protein Gene from a Yeast Artificial Chromosome in Transgenic Mice," *Proc. Natl. Acad, Sci. USA*, 90:10578-10582 (1993).

S. Pettersson et al., "A Second B cell-specific Enhancer 3' of The Immunoglobulin Heavy-chain Locus." *Nature*, 344:165-168 (1990).

S. Pettersson et al., "Cellular Selection Leads to Age-Dependent and Reversible Down-requlation of Transqenic Immunoqlobulin Liqht Chain Genes," *International Immunology*, 1:509-516 (1989).

S. Pettersson et al., "Temporal Control of IgH Gene Expression in Developing B Cells by the 3'Locus Control Region," *Immunobiol.*, 198:236-248 (1997).

G. Pluschke et al., "Generation of Chimeric Monoclonal Antibodies from Mice that Carry Human Immunoglobulin Cγ1 Heavy or CK Light Chain Gene Segments," *Journal of Immunological Methods*, 215:27-37 (1998).

A.V. Popov et al., "Yeast Colony Size Reflects YAC Copy Number.," *Nucleic Acids Research*, 25:2039-2040 (1997).

A.V. Popov et al., "Assembly and Extension of Yeast Artificial Chromosomes to Build Up a Large Locus," *Gene*, 177:195-201 (1996).

L. Pricop et al., "Antibody Response Elicited by T-dependent and "T"-independent Antigens in Gene Targeted K-deficient Mice," *International Immunology*, 6:1839-1847 (1994).

L.E. Reid et al., "A Single DNA response element can confer inducibility by both α- and γ-interferons," *Proc. Natl. Acad. Sci. USA*, 86:840-44 (1989).

P. Rothman et al., "Structure and Expression of Germline Immunoglobulin γ3 Heavy Chain Gene Transcripts: Implications for Mitogen and Lymphokine Directed class-switching," *International Immunology*, 2:621-627 (1990).

J.E. Sale et al., "TdT-Accessible Breaks Are Scattered over the Immunoglobulin V Domain in a Constitutively Hypermutating B Cell Line," *Immunity*, 9:859-869 (1998).

M.J. Sharpe et al., "Somatic Hypermutation of Immunoglobulin χ may depend on Sequences 3' of Cχ and Occurs on Passenger Transgenes," *The EMBO Journal*, 10:2139-2145 (1991).

R. Sherman-Gold, "Monoclonal Antibodies: The Evolution from '80s Magic Bullets to Mature, Mainstream Applications as Clinical Therapeutics," *Genetic Engineering News*, 17 (1997).

M.J. Shlomchik et al., "The Role of B Cells in 1pr/1pr-induced Autoimmunity," *J. Exp. Med.*, 180:1295-1306 (1994).

P. Sideras et al., "Production of Sterile Transcripts of Cγ Genes in an IgM-producing Human Neoplastic B Cell Line that Switches to IgG-producing Cells," *International Immunology*, 1:631-642 (1989).

R. Sitia et al., "Regulation of Membrane IgM Expression in Secretory B Cells: Translational and Post-translational Events," *The EMBO Journal*, 6:3969-3977 (1987).

J. Stavnezer et al., "Immunoglobulin Heavy-chain Switching May be Directed by Prior Induction of Transcripts from Constant-region genes," *Proc. Natl. Acad. Sci. USA*, 85:7704-7708 (1988).

N. Takahashi et al., "Structure of Human Immunoglobulin Gamma Genes: Implications for Evolution of a Gene Family," *Cell*, 29:671-679 (1982).

L.D. Taylor et al., "A Transgenic Mouse That Expreses a Diversity of Human Sequence Heavy and Light Chain Immunoglobulins," *Nucleic Acids Research*, 20:6287-6295 (1992).

L.D. Taylor et al., "Human Immunoglobulin Transgenes Undergo Rearrangement, Somatic Mutation and Class Switching in Mice that Lack Endogenous IgM", *International Immunology*, 6:579-591 (1994).

Y. Teh et al., "The Immunoglobulin (la) α andlaβ Cvtoplasmic Domains Are Independently Sufficient to Signal B Cell Maturation and Activation in Transgenic Mice", *J. Ex. Med.*, 185:1753-1758 (1997).

N. Tuaillon et al., "Human Immunoglobulin Heavy-chain Minilocus Recombination in Transgenic Mice: Gene-segment Use in μ and γ Transcripts," *Proc. Natl. Acad. Sci. USA*, 90;3720-3724 (1993).

A.R. Venkitaraman et al., "The B-cell Antigen Receptor of the Five Immunoglobulin Classes," *Nature*, 352:777-781 (1991).

S.D. Wagner et al., "Antibody Expression from the Core Region of the Human IgH Locus Reconstructed in Transgenic Mice Using Bacteriophage P1 Clones," *Genomics*, 35:405-414 (1996).

S.D. Wagner et al., "The Diversity of Antigen-specific Monoclonal Antibodies from Transgenic Mice Bearing Human Immunoglobulin Gene Miniloci," *Eur. J. Immunol.*, 24:2672-2681 (1994).

S.D. Wagner et al., "Antibodies Generated from human Immunoglobulin Miniloci in Transgenic Mice," *Nucleic Acids Research*, 22:1389-1393 (1994).

S.D. Wagner et al., "Codon bias Targets Mutation," *Nature*, 376:732 (1995).

H. Waldmann et al., "Monoclonal Antibodies for Immunosuppression," *Monoclonal Antibody Therapy Prog Allergy*, 45:16-30 (1988).

M.R. Walker et al., "Interaction of Human IgG Chimeric Antibodies with the Human FcRI and FcRII Receptors: Requirements for Antibody-Mediated Host Cell-Target Cell Interaction," *Molecular Immunology*, 26:403-411 (1989).

G.T. Williams et al., "The α/β Sheath and Its Cytoplasmic Tyrosine Are Required For Signaling By The B-cell Antigen Receptor But Not for Capping or For Serine/Threonine-Kinase Recruitment," *Proc. Natl. Acad. Sci. USA*, 91:474-478 (1994).

G.T. Williams et al., "The Sequence of The μ Transmembrane Segment Determines the Tissue Specificity of the Transport of Immunoglobulin M to The Cell Surface," *J. Exp. Med.* 171:947-952 (1990).

G.T. Williams et al., "Membrane Immunoglobulin Without Sheath or Anchor", *Molecular Immunology*, 30:1427-1432 (1993).

L. Xu et al., "Replacement of Germ-line ε promoter by Gene Targeting Alters Control of Immunoglobulin Heavy Chain Class Switching," *Proc. Natl. Acad. Sci. USA*, 90:3705-3709 (1993).

J. Yélamos et al., "Targeting of Non-Ig Sequences in Place of the V Segment by Somatic Hypermutation," *Nature*, 376:225-229 (1995).

J. Zhang et al., "A Selective Defect in IgG2b Switching as a Result of Targeted Mutation of the Iγ2b Promoter and Exon," *The EMBO Journal*, 12:3529-3537 (1993).

Y.-R. Zou et al., "Cre-loxP Mediated Gene Replacement: a Mouse Strain Producing Humanized Antibodies," *Current Biol.*, 4, pp. 1099-1103 (1994).

X. Zou et al., "Subtle Differences in Antibody Responses and Hypermutation of λ Light Chains in Mice with a Disrupted χ Constant Region," *Eur. J. Immunol.*. 25:2154-2162 (1995).

X. Zou et al., "Dominant Expression of a 1.3 Mb Human IgK Locus Replacing Mouse Light Chain Production," *The FASEB Journal*, 10:1227-1232 (1996).

F.A. Harding et al., "Class Switching in Human Immunoglobulin Transgenic Mice," GenPharm International, Annals New York Academy of Science 764:536-546, 1995.

Trinh et al., "Site-specific and directional gene replacement mediated by Cre recombinase," *Journal of Immunological Methods*, 244:185-193 (2000).

* cited by examiner

TV G1/2 AND TV G4/2

D

Sγ2

μ

Cγ1

VH

SEQUENCE LISTING

```
<160> NUMBER OF SEQ ID NOS: 31

<210> SEQ ID NO 1
<211> LENGTH: 32
<212> TYPE: DNA
<213> ORGANISM: Unknown Organism
<220> FEATURE:
<223> OTHER INFORMATION: Description of Unknown Organism: Lox P site

<400> SEQUENCE: 1
acttcgtata gcatacatta tacgaagtta ta                                      32
```

<210> SEQ ID NO 2
<211> LENGTH: 72
<212> TYPE: DNA
<213> ORGANISM: Artificial Sequence
<220> FEATURE:
<223> OTHER INFORMATION: Description of Artificial Sequence: Linker

<400> SEQUENCE: 2
ctagtcgaca aatattcccc gggcggccgc ttacgtatga attcagcgcg cttctagaac    60
tcgagtgagc tc    72

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence:
      Complimentary strand

<400> SEQUENCE: 3
gatcgagctc actcgagttc tagaagcgcg ctgaattcat acgtaagcgg ccgcccgggg    60
aatatttgtc ga    72

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Linker

<400> SEQUENCE: 4
ctaggcaatt gataatatta agctttacgt atctgatcat cctcgagacg cgtg    54

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence:
      Complementary strand

<400> SEQUENCE: 5
cgttaactat tataattcga aatgcataga ctagtaggag ctctgcgcac gatc    54

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Linker

<400> SEQUENCE: 6
aattaagctt gtacgtactg atcaagatct ggatccagat ct    42

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:
      Complementary strand

<400> SEQUENCE: 7
agatctggat ccagatcttg atcagtacgt acaagtt    37

```
<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
cacaccgcgg tcacatggc                                                    19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ctactctagg gcacctgtcc                                                   20

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
gtcgacgggc tcggggctgg tttctct                                           27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
gggccctgat tcaaattttg tgtctcc                                           27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
ctggagtcct attgacatcg cc                                                22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
ggttctttcc gcctcagaag g                                                 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 14
gctgacacgt gtcctcactg c                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 15
ccccagttgc ccagacaacg g                                              21

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Linker

<400> SEQUENCE: 16
agcttgtcga cacgcgttta attaaggccg gcca                                34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      Complementary strand

<400> SEQUENCE: 17
agcttggccg gccttaatta aacgcgtgtc gaca                                34

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
tggtggccga gaaggcaggc ca                                             22

<210> SEQ ID NO 19
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 19
ccgcgggcat gcaacttcgt ataatgtatg ctatacgaag ttattgtggg acagagctgg    60
gcccagg                                                              67

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20
gtctggcccc tctgctgc                                                  18
```

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
cacccataaa aggctgga                                                   18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
acggctcatg cccattgg                                                   18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 23
tagtgagtgg gcctgact                                                   18

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Linker

<400> SEQUENCE: 24
ggccatggcc ggccat                                                     16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Linker

<400> SEQUENCE: 25
ggccatggcc ggccat                                                     16

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Linker

<400> SEQUENCE: 26
gatccggtac cgatatccaa ttgggccggc cggccatata ggcct                     45

<210> SEQ ID NO 27
<211> LENGTH: 45
<212> TYPE: DNA
<213> ORGANISM: Artificial Sequence

```
<220> FEATURE:
<223> OTHER INFORMATION: Description of Artificial Sequence: Linker

<400> SEQUENCE: 27
gatcaggcct atatggccgg ccggcccaat tggatatcgg taccg                45

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctctccctg tctctgggta aatgagtgcc                                 30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tatccatcac actggcgacc gctcgagcat                                 30

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 30
gcagagcctg ctgaattctg gctg                                       24

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 31
gtaatacaca gccgtgtcct cg                                         22
```

TRANSGENIC ANIMALS FOR PRODUCING SPECIFIC ISOTYPES OF HUMAN ANTIBODIES VIA NON-COGNATE SWITCH REGIONS

CROSS REFERENCE TO RELATED APPLICATIONS

This application claims priority under 35 U.S.C. § 120 as a continuation application of U.S. application Ser. No. 09/999,321, filed Nov. 30, 2001, which issued as U.S. Pat. No. 7,049,426, which is a continuation application of International Application No. PCT/US00/15782, filed Jun. 8, 2000 and published in English, and a continuation-in-part of U.S. application Ser. No. 09/329,582, filed Jun. 10, 1999, which issued as U.S. Pat. No. 6,833,268. The disclosures of all prior applications are incorporated by reference herein in their entirety.

BACKGROUND OF THE INVENTION

A quarter century after the discovery of monoclonal antibodies (mAbs) [G. Kohler and C. Milstein, Nature 256:495-497 (1975)], their therapeutic utility is finally being realized. Monoclonal antibodies have now been approved as therapies in transplantation, cancer, infectious disease, cardiovascular disease and inflammation. Many monoclonal antibodies are in late stage clinical trials to treat a broad range of disease indications. As a result, mAbs represent one of the largest classes of drugs currently in development.

The utility of mAbs stems from their specific recognition of a complex target followed by high affinity binding to that target. Because different $C_H$ isotypes have different effector functions, it is desirable to tailor the mAb isotype to the desired effector function. For example, a mAb bearing a constant region with effector functions, e.g., human $IgG_1$, can be used to direct complement dependent cytotoxicity or antibody-dependent cytotoxicity to a target cell. Alternatively, a mAb with a constant region essentially lacking effector function, e.g., human $IgG_2$ or $IgG_4$, can be used to block signal transduction, either by binding to and neutralizing a ligand, or by blocking a receptor binding site.

Many therapeutic applications for monoclonal antibodies require repeated administrations, especially for chronic diseases such as autoimmunity or cancer. Because mice are convenient for immunization and recognize most human antigens as foreign, mAbs against human targets with therapeutic potential have typically been of murine origin. However, murine mAbs have inherent disadvantages as human therapeutics. They require more frequent dosing to maintain a therapeutic level of mAb because of a shorter circulating half-life in humans than human antibodies. More critically, repeated administration of murine immunoglobulin creates the likelihood that the human immune system will recognize the mouse protein as foreign, generating a human anti-mouse antibody (HAMA) response. At best, a HAMA response will result in a rapid clearance of the murine antibody upon repeated administration, rendering the therapeutic useless. More likely is that a HAMA response can cause a severe allergic reaction. This possibility of reduced efficacy and safety has lead to the development of a number of technologies for reducing the immunogenicity of murine mAbs.

In order to reduce the immunogenicity of antibodies generated in mice, various attempts have been made to replace murine protein sequences with human protein sequences in a process now known as humanization. The first humanization attempts utilized molecular biology techniques to construct recombinant antibodies. For example, the complementarity determining regions (CDR) from a mouse antibody specific for a hapten were grafted onto a human antibody framework, effecting a CDR replacement. The new antibody retained the binding specificity conveyed by the CDR sequences. [See P. T. Jones et al. Nature 321: 522-525 (1986)]. The next level of humanization involved combining an entire mouse VH region (HuVnp) with a human constant region such as γ1. [S. L. Morrison et al., Proc. Natl. Acad. Sci., 81, pp. 6851-6855 (1984)]. Such chimeric antibodies, which still contain greater than 30% xenogeneic sequences, are sometimes only marginally less immunogenic than totally xenogeneic antibodies. [M. Bruggemann et al., J. Exp. Med., 170, pp. 2153-2157 (1989)].

Subsequently, attempts were carried out to introduce human immunoglobulin genes into the mouse, thus creating transgenic mice capable of responding to antigens with antibodies having human sequences. [See Bruggemann et al. Proc. Nat'l. Acad. Sci. USA 86:6709-6713 (1989)]. These attempts were thought to be limited by the amount of DNA which could be stably maintained by available cloning vehicles. As a result, many investigators concentrated on producing mini-loci containing limited numbers of V region genes and having altered spatial distances between genes as compared to the natural or germline configuration. [See U.S. Pat. No. 5,569,825 to Lonberg et al., (1996)]. These studies indicated that producing human sequence antibodies in mice is possible, but serious obstacles remained regarding obtaining sufficient diversity of binding specificities and effector functions (isotypes) from these transgenic animals to meet the growing demand for antibody therapeutics.

In order to provide additional diversity, work has been conducted to add large germline fragments of the human Ig locus into transgenic mammals. For example, a majority of the human V, D, and J region genes arranged with the same spacing found in the unrearranged germline of the human genome and the human $C_\mu$ and $C_\delta$ constant regions was introduced into mice using yeast artificial chromosome (YAC) cloning vectors. [See PCT patent application WO 94/02602 to Kucherlapati et al.]. A 22 kb DNA fragment comprising sequences encoding a human gamma-2 constant region and the upstream sequences required for class-switch recombination was latter appended to the foregoing transgene. In addition, a portion of a human kappa locus comprising $V_k$, $J_k$ and $C_k$ region genes, also arranged with substantially the same spacing found in the unrearranged germline of the human genome, was introduced into mice using YACS. Gene targeting was used to inactivate the murine IgH & kappa light chain immunoglobulin gene loci and such knockout strains were bred with the above transgenic strains to generate a line of mice having the human V, D, J, $C_\mu$, $C_\delta$ and Cγ2 constant regions as well as the human $V_k$, $J_k$ and $C_k$ region genes all on an inactivated murine immunoglobulin background. [See PCT patent application WO 94/02602 to Kucherlapati et al.; see also Mendez et al., Nature Genetics 15:146-156 (1997)].

Yeast artificial chromosomes as cloning vectors in combination with gene targeting of endogenous loci and breeding of transgenic strains provided one solution to the problem of antibody diversity. Several advantages were obtained by this approach. One advantage was that YACs can be used to transfer hundreds of kilobases of DNA into a host cell. Therefore, use of YAC cloning vehicles allows inclusion of substantial portions of the entire human Ig Heavy and light chain regions into a transgenic animal thus approaching the level of potential diversity available in the human. Another advantage of this approach is that the large number of V genes has been shown to restore full B cell development in mice deficient in murine immunoglobulin production. This ensures that these reconstituted mice are provided with the requisite cells for mounting a robust human antibody response to any given immunogen. [See PCT patent application WO 94/02602 to Kucherlapati et al.; L. Green and A. Jakobovits, *J. Exp. Med.* 188:483-495 (1998)]. A further advantage is that sequences can be deleted or inserted onto the YAC by utilizing high frequency homologous recombination in yeast. This provides for facile engineering of the YAC transgenes.

As mentioned above, there are several strategies that exist for the generation of mammals that produce human antibodies. In particular, there is the "minilocus" approach that is typified by work of GenPharm International, Inc. and the Medical Research Council, YAC introduction of large and substantially germline fragments of the Ig loci that is typified by work of Abgenix, Inc. (formerly Cell Genesys), and introduction of entire or substantially entire loci through the use microcell fusion as typified by work of Kirin Beer Kabushiki Kaisha.

In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described or related to work in U.S. Pat. No. 5,545,807 to Surani et al. and U.S. Pat. Nos. 5,545,806, 5,625,825, 5,625,126, 5,633,425, 5,661,016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International U.S. patent application Ser. Nos. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al. "A transgenic mouse that expresses a diversity of human sequence heavy and light chain immunoglobulins." *Nucleic Acids Research* 20:6287-6295 (1992), Chen et al. "Immunoglobulin gene rearrangement in B-cell deficient mice generated by targeted deletion of the $J_H$ locus" *International Immunology* 5:647-656 (1993), Tuaillon et al. "Analysis of direct and inverted $DJ_H$ rearrangements in a human Ig heavy chain transgenic minilocus" *J. Immunol.* 154:6453-6465 (1995), Choi et al. "Transgenic mice containing a human heavy chain immunoglobulin gene fragment cloned in a yeast artificial chromosome" *Nature Genetics* 4:117-123 (1993), Lonberg et al. "Antigen-specific human antibodies from mice comprising four distinct genetic modifications." *Nature* 368:856-859 (1994), Taylor et al. "Human immunoglobulin transgenes undergo rearrangement, somatic mutation and class switching in mice that lack endogenous IgM." *International Immunology* 6:579-591 (1994), Tuaillon et al. "Analysis of direct and inverted $DJ_H$ rearrangements in a human Ig heavy chain transgenic minilocus" *J. Immunol.* 154:6453-6465 (1995), and Fishwild et al. "High-avidity human IgG monoclonal antibodies from a novel strain of minilocus transgenic mice." *Nature Biotech.* 14:845-851 (1996), the disclosures of which are hereby incorporated by reference in their entirety.

In connection with YAC introduction, Green et al. *Nature Genetics* 7:13-21 (1994) describes the generation of YACs containing 245 kb and 190 kb-sized germline configuration fragments of the human heavy chain locus and kappa light chain locus, respectively, which contained core variable and constant region sequences. Id. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J. Exp. Med.* 188:483-495 (1998), and U.S. patent application Ser. No. 08/759,620, filed Dec. 3, 1996, the disclosures of which are hereby incorporated by reference. Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In connection with the microcell fusion approach, portions or whole human chromosomes can be introduced into mice as described in European Patent Application No. EP 0 843 961 A1, the disclosure of which is hereby incorporated by reference. It will be understood that mice generated using this approach and containing the human Ig heavy chain locus will generally possess more than one, and potentially all, of the human constant region genes. Such mice will produce, therefore, antibodies that bind to particular antigens having a number of different constant regions. Thus, there is no way to preselect the desired constant region for particular effector function.

Also, the transchromosomes are mitotically and meiotically unstable. As a result, either the human IgH, the human IgK or both transchromosomes are lost with a frequency approaching 80%. This results in aberrantly high recovery of mouse Igλ mAbs and hybridoma instability.

Technology exists for in vitro isotype switching of antibodies. Antibodies produced from transgenic mice that produce only IgG1 isotypes, from transgenic mice that produce multiple IgG isotypes, or from phage display technologies may have the desired antigen-specificity and affinity, but not have the desired effector function. In this instance, the variable region of the heavy chain, at the least, and most likely, the entire light chain of the antibody must be cloned.

Methods for cloning include recovery of genomic DNA from a library, recovery of cDNA from a library, recovery of genomic DNA using specific oligonucleotide primers, and PCR using specific oligonucleotide primers and cDNA as template (RT-PCR). Each method, especially PCR-based methods, require that the clone be sequenced to verify faithful reproduction of the antibody coding sequences. Then the variable region of the heavy chain must be operably linked via DNA ligation to the desired constant region gene. Then, the engineered VH-CH gene must be operably linked to expression controlling regions such as a promoter-enhancer and a polyadenylation site. Such an expression construct might also be needed for the Ig light chain of the antibody.

The expression construct(s) must be stably transfected into a suitable host cell for transcription and translation to produce a secreted form of the engineered mAb. Typically, at the least, extensive screening must be performed to find a clone of the cell line that expresses sufficient levels of mAb for further experiments and subsequent manufacturing. More likely, methodologies such as DNA amplification must be employed to raised the copy number of the antibodies expression constructs and consequently, the expression level of the mAb.

Finally, the re-engineered mAb must be re-tested to confirm that it has retained the desired qualities and has the desire function, including specificity, affinity, and presence or absence of effector function. Other technologies for isotype switching exist, but all such programs to re-engineer the mAb isotype require experimentation and expertise in molecular biology and tissue culture, and are labor intensive, slow, expensive, and covered by issued and pending intellectual property, requiring additional licensing fees, if even available for licensing. Thus, re-engineering of mAb from one isotype to another requires expertise, extra monetary expenditure and slows down the development of the monoclonal antibody for pre-clinical and clinical trials.

Having a technology that would produce the mAb with the desired Cγ isotype a priori would obviate the need for antibody re-engineering. By having three different XenoMouse strains, one each capable of making only Cγ2, Cγ4 or Cγ1, a transgenic mouse can be pulled off the shelf, and then can be immunized to produce mAbs with the desired affinity, antigen-specificity and the desired isotype and with the desired effector function a priori. This increases the efficiency and user-friendliness for development of monoclonal antibody based therapeutics. No expertise in molecular biology or antibody engineering is required. The antigen-specific mAb can be taken directly into pre-clinical studies without the extra expenditure of money and time, resulting in a decrease in the development cost and an acceleration of the timeline for development of the therapeutic mAb.

The present invention is directed to solving the problem of obtaining a pre-selected human antibody isotype from a transgenic mouse, in addition to the desired specificity, which is compatible with the therapeutic goals for which the antibody will be used.

SUMMARY OF THE INVENTION

The present invention solves the problems referred to above by providing, in one aspect of the invention, transgenic non-human animals capable of producing high affinity, fully human antibodies of a desired isotype in response to immunization with any virtually any desired antigen. The aforementioned transgenic non-human animals have in their somatic and germline cells an unrearranged human immunoglobulin heavy chain transgene that encodes, on rearrangement, a fully human immunoglobulin heavy chain of the desired isotype.

The human immunoglobulin heavy chain transgene in the foregoing animals comprises a human constant region gene segment comprising exons encoding the desired heavy chain isotype, operably linked to switch segments from a constant region of a different heavy chain isotype, i.e., a non-cognate switch region.

The foregoing transgenic non-human animal also has in its somatic and germ cells a human immunoglobulin light chain transgene. In a preferred embodiment, the endogenous immunoglobulin heavy and light chain loci of the transgenic non-human animal are inactivated so that the animal is incapable of producing endogenous heavy or light chains. In a particularly preferred embodiment, the non-human transgenic animal is a mouse.

In another aspect, the invention provides an unrearranged human immunoglobulin heavy chain transgene that encodes, on rearrangement, for a human heavy chain of a desired isotype. The transgenes of the invention comprise a DNA sequence identical to the DNA sequence of human chromosome 14 starting at least from the first D segment gene of the human immunoglobulin heavy chain locus, continuing through the J segment genes and the constant region genes through Cμ of that locus. In the transgenes of the invention, the aforementioned DNA fragment is operably linked to and is capable of isotype switching to an additional constant region segment. Said additional constant region segment comprises a switch region and human constant region coding segment, wherein the constant region coding segment is operably linked to a switch region that it is not normally associated with, i.e., a non-cognate switch region. In transgenes of the invention, the foregoing DNA fragment and constant region segment is operably linked to at least one human V segment gene. In one embodiment of the invention, the transgene is a yeast artificial chromosome (YAC).

In the transgenes of the invention, the non-cognate switch region may be a switch region from a different species than the constant region coding segment. In one embodiment, the non-cognate switch region is a mouse switch region operably linked to a human constant region coding segment encoding a human gamma, alpha or epsilon constant region. In a preferred embodiment, the switch region is a mouse gamma-1 switch region. In more preferred embodiments, the switch region is a mouse gamma-1 switch region and the human constant region coding segment encodes a gamma-1 or a gamma-4 constant region. In a particularly preferred embodiment, the transgene is the yH2Bm yeast artificial chromosome (YAC) or the yH2Cm YAC.

In another embodiment, both the non-cognate switch region and the constant region coding segment are human sequences, the non-cognate switch region being from a human constant region of a different isotype than the constant region coding segment. In a preferred embodiment, the switch region is a human gamma-2 switch region and the constant region coding segment is an isotype other than gamma-2. In a more preferred embodiment, a transgene of the invention comprises a human gamma-2 switch region and a human gamma-1 or human gamma-4 constant region coding segment. In particularly preferred embodiments, the transgene is the yHG1 YAC or the yHG4 YAC.

In still another embodiment, a transgene of the invention comprises a human non-cognate switch region and a human constant region coding segment, wherein the switch region and the membrane exons of the constant region coding segment are from the same human constant region isotype and the secreted constant region exons are from a different isotype. The transgenes of the invention also may comprise a human non-cognate switch region and a human constant region coding segment wherein the switch region is from one isotype, the secreted constant region exons are from a second isotype and the membrane constant region exons are from yet a third isotype.

In a preferred embodiment, the switch region and membrane exons are from a human gamma-2 constant region. In particularly preferred embodiments, the switch region and membrane exons are from a human gamma-2 constant region and the secreted constant region exons are from a human gamma-1 or a human gamma-4 constant region. In preferred embodiments, the transgene is the yHG1/2 YAC or the yHG4/2 YAC.

In another embodiment, any of the foregoing transgenes of the invention comprise a plurality of different human VH genes. In a preferred embodiment, the transgene comprises at least 50% of the human germline VH genes. In another embodiment, the transgene comprises at least 40 different human VH genes. Preferably, the transgene comprises at least 66 different human VH genes. Most preferably, the transgene comprises the entire human VH region of a human heavy chain locus. In another embodiment, the transgene comprises a sufficient number of different human VH genes so that the transgene is capable of encoding at least $1 \times 10^5$ different functional human immunoglobulin heavy chain sequence combinations, without taking into account junctional diversity or somatic mutation events. In still another embodiment, the number of human VH genes in the transgene is sufficient to produce at least 50% of the B-cell population of a wild-type mouse in a transgenic mouse containing the transgene.

A transgene of the invention further comprises a murine 3' enhancer, positioned 3' of the constant region gene containing the non-cognate switch region. In one embodiment the murine 3' enhancer is an approximately 0.9 kb core region of the native enhancer. In an alternative embodiment, the 3' enhancer is an approximately 4 kb region of the murine enhancer that includes the core region. In still another embodiment, the transgene includes the mouse major enhancer locus.

In another aspect, the invention provides methods for producing the transgenic non-human animals of the invention. According to the methods, an unrearranged human immunoglobulin heavy chain transgene is introduced into the germline of a non-human animal to produce a transgenic non-human animal having the transgene in its somatic and germ cells. Breeding of the human heavy chain transgenic animals with transgenic non-human animals containing a human immunoglobulin light chain transgene produces transgenic non-human animals containing a human heavy chain transgene of the invention and a human light chain transgene. Either of the aforementioned transgenic non-human animals can be bred with animals having inactivated heavy and/or light chain loci to produce a transgenic non-human animal that produces a fully human antibody and is incapable of producing an endogenous antibody.

In one embodiment, a transgene of the invention is introduced into an embryonic stem (ES) cell which is then inserted into a blastocyst. The blastocyst with the ES cell containing the transgene of the invention is then surgically inserted into the uterus of the non-human animal to produce a chimeric non-human animal. The chimeric animal is bred to obtain germline transmission of the transgene of the invention to produce a transgenic, non-human animal having somatic and germ cells containing the transgene of the invention. Accordingly, a further aspects of the invention are an ES cell comprising a transgene of the invention and non-human animals having the transgene in some or all of its cells.

In still another aspect, the invention provides a method for producing high affinity, fully human antibodies of a desired isotype that are specific for an antigen of interest in a transgenic non-human animal of the invention. According to the method, a transgenic non-human animal of the invention is contacted with an antigen of interest under conditions that induce the production of an antibody by the B-cells of the animal. High affinity, fully human, antigen-specific antibodies of the desired isotype can be collected from the blood stream of the transgenic non-human animal.

Alternatively, according to the methods of the invention, the antibody producing B-cells can be harvested from the animal and immortalized by any means known in the art, for the continuous production of antibodies. In one embodiment, the B-cells are fused with a mouse myeloma cell-line to produce antibody-secreting hybridomas. Such hybridomas can be screened to select those secreting high affinity, fully human, antigen-specific antibodies.

In a further aspect, the invention provides hybridomas derived from antibody producing B-cells harvested from a transgenic animal of the invention.

The antibodies of this invention may also be by the expression of B-cells expressing a desired antibody, by cloned human immunoglobulin genes, by phage-display, or by any other method known in the art.

DETAILED DESCRIPTION OF THE INVENTION

Figure 1:
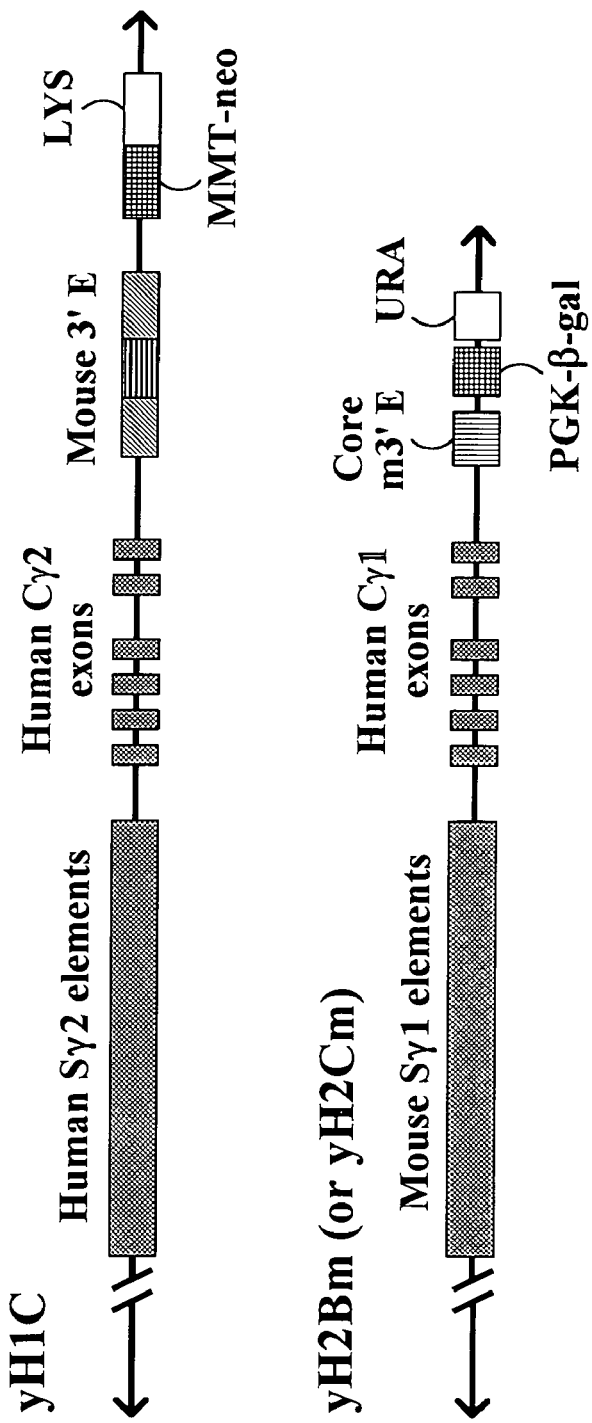
FIG. 1 is a schematic depiction of the yH1C and yH2Bm (or yH2Cm) yeast artificial chromosomes (YACs).
Figure 2:
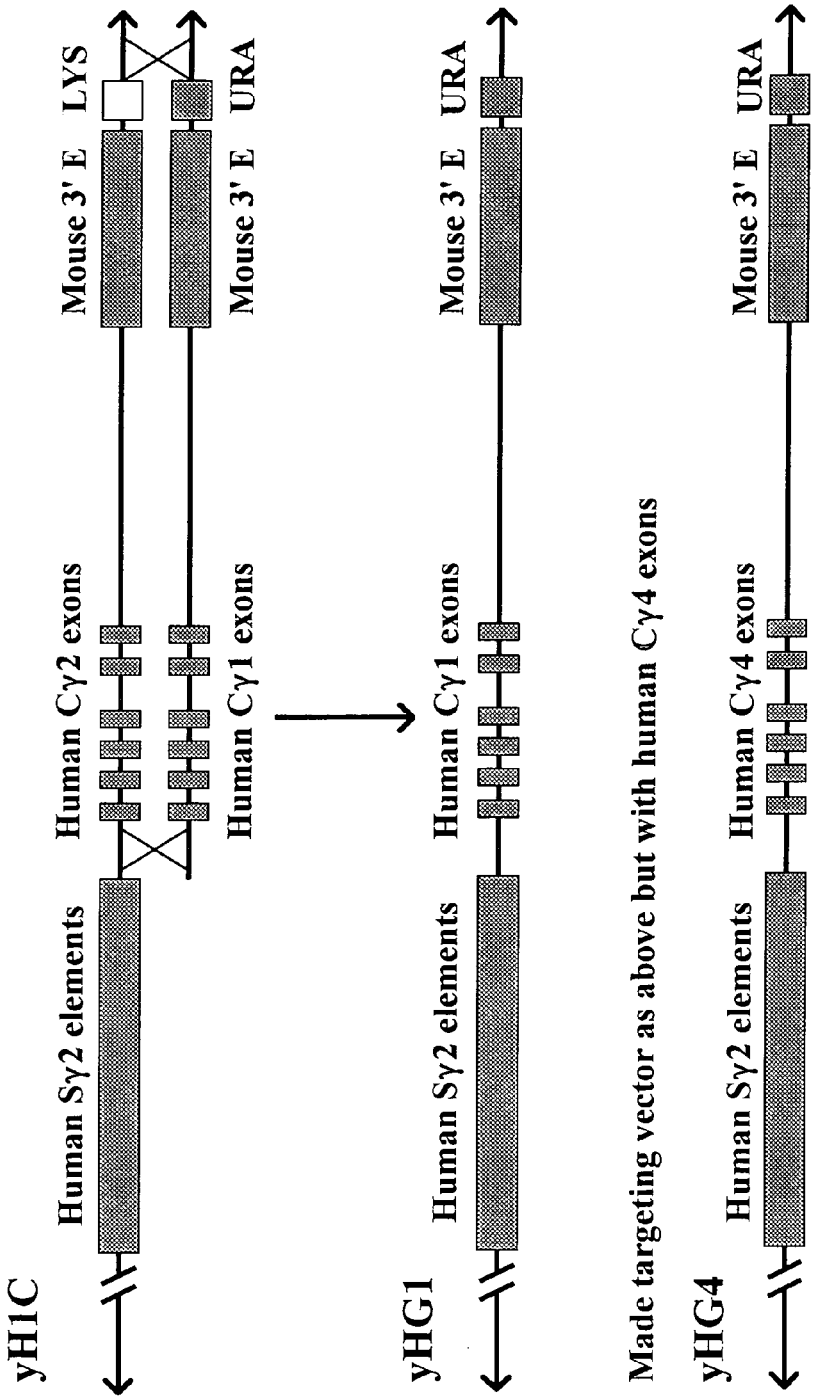
FIG. 2 is a schematic depiction of the yH1C and yHG1 yeast artificial chromosomes (YACs).

This invention relates to novel transgenes for the production of human immunoglobulin heavy chains of a desired isotype and to embryonic stem (ES) cells and transgenic non-human animals comprising the transgenes. This invention also relates to methods for producing such transgenic non-human animals and for producing fully human antibodies of a desired isotype in response to an antigen of interest in a transgenic animal of the invention.

The transgenes and transgenic non-human animals of the invention are useful in the production of fully human antibodies of various isotypes or classes. For therapeutic uses of such antibodies, the different effector functions of the individual antibody isotypes permits the use of a particular isotype to achieve a desired therapeutic effect. It is desirable, thus, to produce strains of transgenic non-human animals that produce antibodies of a single isotype following immunization with an antigen of interest.

In order that the invention herein described may be more fully understood, the following detailed description is set forth. In the description, the following terms are employed:

Gene regions—the DNA involved in producing or selecting a particular polypeptide chain; including promoters, enhancers, any switch regions preceding a constant gene as well as upstream and downstream preceding and following coding regions, and intervening sequences such as introns between coding segments or exons.

Gene segments—the coding segments in a multi-exon gene such as an immunoglobulin heavy chain constant region. For example, the gene for the secreted form of the human immunoglobulin heavy chain gamma constant region contains 4 gene segments: CH1, H, CH2, and CH3.

Germline configuration—the arrangement and spacing of immunoglobulin gene segments before any somatic gene rearrangement has occurred.

Klenow Fragment—A large fragment of the enzyme Polymerase I, usually from E. coli. This fragment does not contain any 5' to 3' exonuclease activity and only has polymerase activity. It can be used for end-filling of DNA molecules to create blunt ends.

Library—A mixture of cloned DNA fragments usually propagated on DNA-based vectors, e.g., plasmids in bacteria, lambda bacteriophage in E. coli, P1 bacteriophage in E. coli, bacterial artificial chromosomes in E. coli, yeast artificial chromosomes in Saccharomyces cerevisiae, mammalian artificial chromosomes in cultured cells, mammalian chromosome fragments in somatic cell hybrids.

Linker—Synthetic DNA fragments that are designed to contain restriction sites and other properties which can be added to larger DNA molecules, e.g., to facilitate cloning and/or build back portions of DNA fragments encoding desired polypeptides.

Screening the Library—The process of searching for a specific sequence of cloned DNA in a library.

Sterile transcripts—Transcripts produced from the Ig loci thought not to be translated into required somatic gene segment rearrangement or class switch recombination. In a B cell or a pre-B cell producing IgM there may be, for example, germline mRNA transcripts corresponding to the CH genes which potentially indicate which isotype the cell will switch to and produce.

Vector—A DNA molecule used to transport a foreign DNA into a host and being replicated in that host, to transform that host. available vectors include but are not limited to viruses (prokaryotes and eukaryotes), bacterial plasmids or artificial chromosomes.

Yeast artificial chromosomes (YACS)—cloning vehicles constructed from elements of yeast chromosomes which allow the vector to be replicated and maintained in yeast cells in vivo. Yeast elements include a centromere, an autonomous replication sequence, a pair of telomeres, yeast selectable markers, and usually a bacterial origin of replication and selectable marker for replication and selection of the YAC vector arms in bacteria. DNA inserts of up to at least 2000 kb can be cloned and maintained using YACs.

XenoMouse Development

XenoMouse is a mouse which has inactivated mouse IgH and Igk loci and is transgenic for functional megabase-sized human IgH and Igk transgenes. The generation and characterization of XenoMouse has been described [See Mendez et al., Genomics 26:294-307 (1995); Mendez et al., Nature Genetics, 15, pp. 146-156 (1997); Green et al., Nature Genetics 7:13-21 (1994); International Patent application WO 94/02602, by Kucherlapati et al., published on Feb. 3, 1994]. More particularly, there have been deletions of key elements of the mouse IgH and Igk loci by homologous recombination in mouse embryonic stem cells, followed by germline transmission of the mutations and subsequent breeding to produce mice which are homozygous for both inactivated loci (DI mice). Such mice are incapable of making mouse IgH and Igk chains and display an arrest in B cell development in the bone marrow at the proB/preB-I stage. [Green et al, Nature Genetics, 7, pp. 13-21 (1994); Green and Jakobovits, J. Exp. Med., 188:483 (1998)]. The human IgH and Igk loci, cloned on yeast artificial chromosomes, were introduced into ES cells via yeast spheroplast-ES cell fusion [Jakobovits et al., Nature 362:255-258 (1993)]. After germline transmission and subsequent breeding onto the DI background, the human IgH and Igk YAC transgenes, yH1C and yK2, were able to functionally substitute for their murine counterparts and support B cell development. In addition, these mice produced fully human IgMκ and IgG2κ antibodies, and ultimately, hybridomas secreting antigen-specific, high affinity fully human IgG2κ monoclonal antibodies with therapeutic potential were generated.

The yH1C Transgene

The human IgH transgene, yH1C, is composed of 66 VH, all the D elements, all J elements, Cμ and Cδ, all regulatory elements, all in germline configuration. By using homologous recombination in yeast, the 3' end of yH1C was appended with a 22 kb fragment containing the human γ2 gene, including its switch regulatory elements, and a 4 kb fragment containing the mouse 3' enhancer element [See Mendez et al., Nature Genetics 15:146-156 (1997) the disclosure of which is hereby incorporated by reference]. The left YAC arm carries expression cassettes for the yeast selectable marker ADE2, the mammalian selectable marker and the right YAC arm carries expression cassettes for the yeast selectable marker LYS2 and a mammalian selectable marker Neo, encoding resistance to the drug, G418. The latter is non-functional in ES cells as its promoter, MMT (mouse metallothionine), is probably non-functional in ES cells. In other cell types, the MMT promoter drives transcription at only very low levels, if at all, under normal physiological conditions and requires heavy metals, e.g., Cd, for higher level transcription. Indeed, ES cells transfected with this construct never became resistant to even low levels of G418.

B-Cell Development

B cell development initiates in the bone marrow with a deletional recombination between a D and J gene. Subsequently, a V gene recombines with the DJ to make a VDJ, which is transcribed, producing a spliced VDJCμ transcript. If the transcript is in-frame, then a μ chain is synthesized upon translation. Similarly, and generally after $V_H DJ_H$ recombination and successful pairing of the μ chain with surrogate light chain, the Ig light chain loci rearrange their V and J gene segments. Successful B cell development in the bone marrow results in B cells expressing IgMκ or IgMλ on the cell surface. In the mouse, 95% of the B cells express IgMκ; in the human, approximately 60% of the B cells express IgMκ.

These IgM producing B cells form the primary immune repertoire and perform immune surveillance for recognition of foreign antigens. In the mouse or in humans, these IgM producing B cells can subsequently undergo isotype class-switching from IgM to the IgG or IgA, or IgE isotypes. The frequency of class switching increases during an immune response. Mice and humans each have genes for four different isotypes of IgG. They are IgG1, IgG2a, IgG2b, and IgG3 in the mouse, and IgG1, IgG2, IgG3, IgG4 in the human. Humans have two IgA isotypes, IgA1 and IgA2, and one IgE isotype. In a mouse, there is, on average, 6500, 4200 and 1200 μg/ml of IgG1, IgG2a, and IgG2B respectively, and 260 μg/ml IgA. In the human, of the total IgG, about 70% is IgG1, 18% is IgG2, 8% is IgG3 and 3% is IgG4. In the total IgA in humans, about 80% is IgA1 and 20% is IgA2.

Effector Functions of Antibodies

Different isotypes have different effector functions. Such differences in function are reflected in distinct 3-dimensional structures for the various immunoglobulin isotypes [P. M. Alzari et al., Annual Rev. Immunol. 6:555-580 (1988)]. For example, the human IgG1 and IgG3 isotypes are involved in complement mediated-lysis or antibody-dependent cellular cytotoxicity (ADCC) and the IgG2 and IgG4 have little or no known effector functions. [Snapper and F. D. Finkelman, *Fundamental Immunology* 3d Ed., pp. 837-863]. Since different effector functions are associated with different IgG isotypes, it is therefore desirable to be able to select the isotype and the binding specificity of the mAb to produce optimal therapeutic benefit. For example, if a mAb is desired to neutralize a cytokine response or block the activity of a receptor, then a mAb lacking effector functions, such as an IgG2 or an IgG4 might be desired. On the other hand, if the killing of a cell via binding of a mAb to an antigen on the cell surface is desired, then a mAb such as an IgG1, with its specific effector functions, either ADCC or CML, is desired. Thus, a transgenic mouse engineered for the generation of fully human monoclonal antibodies would be desirable to control the isotype of the resulting monoclonal antibodies. In this case, one could select a particular antibody isotype by immunizing a particular transgenic mouse strain which produces only the desired human antibody isotype. Such mice would ensure that any resulting antigen-specific IgG mAbs would possess the desired effector functions. This would preclude subsequent re-engineering of the antibody gene to change the constant region including the isolation (cloning) of the variable region and the ligation of said VH region to the desired CH gene.

In one embodiment of the present invention, the sole Cγ gene on the yH1C human IgH YAC, Cγ2, is replaced by another CH gene. For example, instead of the 22 kb fragment carrying the complete human Cγ2 gene other inserts carrying human CH genes could be cloned into the targeting vector of Mendez et al. [See Mendez et al., *Nature Genetics* 15:146-156 (1997)]. The human Cγ1-4 genes have been sequenced and can be isolated from bacteriophage lambda libraries of human genomic DNA and subsequently recovered on EcoRI fragments of about 20-25 kb [See J. W. Ellison et al., *Nucleic Acids Res.*, 13:4071-4079 (1982); J. Ellison et al., Proc. Natl. Acad. Sci. USA, 79:1984-1985 (1982); S. Huck et al., *Nucleic Acids Res.*, 14:1779-1789 (1986); J. Ellison et al., DNA, 1:11-18 (1981) the disclosures of which are hereby incorporated by reference]. Similarly, the sequences for mouse Cγ1, Cγ2a, Cγ2b, and Cγ3 are all known [See H. Hayashida et al., EMBO Journal, 3:2047-2053 (1984) the disclosure of which is hereby incorporated by reference].

Class Switching

Class switch recombination (CSR) from IgM to IgG, IgA or IgE is mediated through a deletional recombination event occurring between tandem directly repetitive switch regions present 5' of all IgH constant region genes except Cδ. Switch regions are known to be composed of the I promoter, the I exon and a set of direct repeats flanked by inverted repeat sequences. Enhancers and cytokine response sequences are known to lie in the region near the I promoter. At least one transcriptional enhancer, located immediately 3' of the downstream inverted repeat, in the mouse Cγ1 gene has been hypothesized [J. P. Manis et al., J. Exp. Med. 188:1421-1431 (1998)]. Also required is iEm, an enhancer located between JH and Cm. Transcription initiates at the I promoter and proceeds through the I exon to the end of the C gene. This transcript is processed to yield a non-coding sterile transcript with the I exon spliced to the CH exons. Transcription through the switch region is required for class switch recombination. The human and mouse Sµ and Sγ regions have been sequenced, the sequences of which are publicly available from the Genbank database.

In the mouse, different combinations of lymphokines and activators have profoundly different effects on class switching from IgM to individual CH genes. For example, in vitro the combination of LPS and interleukin-4 induces class switching to IgG1 and IgE and suppresses switching to IgG2b and IgG3. Other lymphokines affecting CSR include but are not limited to, IL-5, TGF-β, interferon-γ. These lymphokines are secreted in vivo by helper cells such as the antigen presenting T- and follicular dendritic cells in the germinal centers of secondary lymphoid tissues. These lymphokines modulate transcription of their responding CH genes prior to CSR, probably through activation of the corresponding I promoter. For example, the IL-4 response element in the mouse Cγ1 I promoter has been mapped. [Rothman et al., *Int. Immunol* 2, pp. 621-627 (1990).] The lymphokine responsiveness of the human switch regions is not yet as well-characterized as that of the mouse. However, the different human switch (S) regions may also have different responses to different lymphokines and activators. This may in part be the source of the different levels of the IgG subclasses in human serum.

Non-Cognate Switching

In view of the real and possible differential responsiveness of mouse and human S regions, respectively, to lymphokines and other activators, it is desirable to have heterologous switch regions controlling CSR in human antibody producing transgenic mice. For example, Igγ1 is the most abundant class of IgG in the mouse. It is known also that CSR can occur from human Sµ regions to mouse Sγ1. [Taylor et al., *Int. Immunol*, 6, pp. 579-591 (1994).] Using standard tools of molecular biology and the well-characterized and cloned mouse Sγ1 sequence [Mowatt and Dunnick, *J. Immuno.*, 136, pp; 2674-2683 (1986), Genbank accession #M12389], it is possible to engineer a DNA vector having the mouse Sγ1 functionally linked to a human CH coding sequence, e.g., human Cγ1. Included downstream of the human CH coding sequences would be a sequence encompassing the mouse 3' enhancer. The m3'E sequence could be a 4 kb XbaI fragment or a 900 bp Stu I fragment, both of which encompass the core DNAse I hypersensitive sites, HS1,2. [Dariavach et al., *Eur. J. Immunol.* 21, pp. 1499-1504 (1991); Petterson et al., *Immunobiol.*, 198, pp. 236-248 (1997)]. By having 5' and 3' flanking homology to yH1C and an appropriate selectable marker, such a vector can be recombined in vivo in yeast to replace the human Cγ2 gene on yH1C. A YAC engineered in this way would retain intact all of the VH, $D_H$, $J_H$, $C_\mu$, and $C_\delta$ of yH1C, but would have a chimeric CH gene: the mouse Sγ1 elements would control switching from human IgM to the downstream human CH coding sequences.

In another embodiment, the human Cγ2 coding sequences, including all of the exons for the secreted and membrane-bound forms of the $C_H$ gene are replaced by another human $C_H$ gene. In this way, the human Sγ2 sequences control CSR from $C_\mu$ to the downstream $C_H$ gene. It is known that the hSg2 sequences are stable in yH1C while other human S sequences, some of which have longer tandem arrays of S repeats may be less stable. It is also known that CSR in transgenic mice with the human Cγ2 gene is efficient and generates high serum levels of human IgG2 and results in efficient production of fully human IgG2 mAbs. Thus, it may be preferable to retain the human Sγ2 with their favorable stability and in vivo response to antigen challenge while engineering CSR to occur to another isotype, e.g., either Cγ1 or Cγ4. To accomplish this, a vector with the following elements would be constructed: 5' homology located between human Sγ2 and the human Cγ2 coding exon 1, a human CH gene other than Cγ2, the mouse 3' enhancer, a yeast selectable marker, and 3' targeting homology in the YAC arm for example. Such a vector would be introduced into yeasts carrying yH1C and targeted recombinants would be selected and screened. It should be understood that in these examples many variations can be created be one skilled in the art and that these examples are not meant to indicate that these are the only means to achieve the end of a transgenic mouse having CSR driven by heterologous S regions.

The Role of Enhancers

In addition to S regions, other cis regulatory elements are known to be or may be required for CSR. The requirement for iEm has been mentioned. Also, an enhancer required for expression of normal levels of IgG has been hypothesized to be between the 3' inverted repeat of mouse Sγ1 and the $C_H1$ exon. This enhancer could be conserved in other $C_H$ genes in the mouse and humans and this interval should be retained in any vector designed for CSR via heterologous switch sequences. [Elenich et al., *J. Immunol.* 157, pp. 176-182 (1996); Cunningham et al., *Int. Immunol.*, 10, pp. 1027-1037 (1998)]. Also important is a cluster of enhancers 3' of the Cα gene in mouse and humans. In the mouse the 40 kb region downstream of Cα contains four enhancer elements, hallmarks of which are Dnase I hypersensitive sites (HS). These enhancers are in 5' to 3' order: HS3a, 4 kb downstream of Cα; HS1,2 (known in the literature and in this application as m3'E), 15 kb 3' of Cα; HS3b 25 kb 3' of Cα; and HS4, ca; 30 kb 3' of Cα; HS1,2, HS3a, and HS3b enhance expression in activated B cells and plasma cells. HS4 is active over the course of B cell development, but is apparently dispensable as the yH1C YAC lacks HS4 and yet supports efficient B cell development in mice. Together, these elements can act synergistically to enhance transcription and are hypothesized to form a locus control region (LCR) for the IgH locus in mouse and humans. It has been hypothesized that there is some redundancy of function of the individual HS units. The unimpaired activity of these elements may be required for CSR although HS1,2 and HS3a are separately dispensable CSR [See J. P. Manis et al., J. Exp. Med. 188:1421-1431 (1998)].

HS1,2 (3'E) was the first discovered enhancer of this set. The HS1,2 sites and sequences homologous to consensus binding domains for transcription factors such as AP-1 can be isolated on a 900 bp Stu-I fragment. [Dariavich et al., *Eur. J. Immunol.*, 21, pp. 1499-1504 (1991); Genbank accession #X62778]. The 3'E in the mouse is oriented opposite to the 3'E of the rat, suggesting that like other enhancers, its function is orientation independent. However, the 3'E has been shown to have position dependent activity and enhance transcription more effectively when positioned further from the promoter. *Gene,* 136, pp. 349-353 (1993). It is known that a 4 kb XbaI fragment encompassing the 900 bp StuI fragment with HS1, 2, positioned 3' of the human Cg2 gene, can support CSR and high level expression of IgG2 in transgenic mice [See Mendez et al., *Nature Genetics* 15:146-156 (1997)].

The insertion of a strong promoter (PGK) into the mouse IgH 3' LCR can abrogate class switching to some IgG isotypes (IgG2a, IgG3, IgG2b) and lower expression of others (IgG1, IgA). Curiously, the promoter and its expressed gene also come under the control of the LCR: the PGK-driven expression construct is down-regulated and can be up-regulated in activated B cells [J. P. Manis et al., J. Exp. Med. 188:1421-1431 (1998)]. Thus, in YAC transgenes carrying a β-gal expression construct driven by the strong constitutive promoter, PGK, with construct 3' and adjacent to the mouse 3'E core construct (900 bp StuI), it may be advantageous to screen for YACs that have integrated into the ES cell genome with concomitant loss of the PGK-β-gal construct. This can be accomplished by PCR using primers for β-gal, or by Southern blots probed with the β-gal gene.

Immunoglobulin Membrane Exons

Two forms of each IgH isotype and class, secreted (s) and membrane (m), can be made by a B cell. Ig(s) and Ig(m) are synthesized through alternative splicing of IgH transcripts. Two membrane exons lie 2 kb downstream of the CH3 exon of each human IgG gene. Encoded by the membrane exons are a hydrophobic transmembrane sequence and a short approximately 3 amino acid cytoplasmic tail. Alternative splicing from CH3 to the first membrane exon results in membrane bound IgG. The membrane bound Ig interacts with other proteins in the B cell, e.g., Igα, Igβ and CD45, among others, to form a complex called the B cell receptor (BCR) that is capable of signal transduction. Binding of antigen by the V region of the IgG displayed in the extracellular environment, e.g., soluble or on antigen presenting cells, can lead to signal transduction. This signal transduction by the BCR leads to activation of the B cells and ultimately efficient affinity maturation and germinal center formation in the secondary immune response.

Additionally, binding of antigen by the Ig of the BCR may lead to internalization, processing of and presentation of antigen fragments by MHC molecules for presentation to helper cells. Clearly, efficient assembly of a functional BCR is required for an efficient primary and secondary immune response.

The human IgG1 membrane exons may not complex well with the other components of the BCR, resulting in a chimeric BCR that may not signal as efficiently as that of the mouse. G. Pluschke et al., *J. Immunolog. Methods,* 215, pp. 27-37 (1998). A human IgG1 construct with all of the human exons encoding the secreted and membrane forms of IgG1 was inserted into the mouse IgG2a locus such that all of the mouse Cγ2a exons were replaced and CSR to the human coding exons was under the control of the mouse Sγ2a region. Chimeric human IgG1 (mouse VDJ-human IgG1) was expressed at levels 100× less than mouse IgG2a and antigen specific mAbs were not recovered. Thus, although class switching driven by the mouse Sγ2a did occur, the normal immune response was compromised. Alternatively, exons coding for secreted human IgG1 have been used to replace only the exons encoding the secreted form of mouse IgG1. This construct produced a chimeric IgG1 heavy chain gene that contained all of the human exons for secreted IgG1 but with the downstream mouse membrane exons intact. Class switching would have been driven by the mouse Sγ1 regions. Membrane bound Ig would be mouse V-human γ1 CH1-CH3-mouse Cγ1(mem). In this transgenic mouse, the serum levels of human IgG1 were equivalent to mouse IgG1 in normal naive mice. Thus, the mouse Sγ1 can drive efficient class switching and the mouse IgG1 membrane exons can function with at least the human γ1 CH1-CH3 exons. The authors did not test the mice for production of antigen-specific mAbs. As in the previous construct, the resulting IgG1 mAbs would have been chimeric: mouse VDJ functionally linked to the secreted form of human Cγ1.

Given these results, an intact set of human Cγ1 exons, coding both the secreted and membrane forms of Cγ1, and functionally linked to a human IgH locus ($V_H$, $D_H$, $J_H$, $C_\mu$, $C_\delta$ and Sγ regions) may function sub-optimally because of inefficient assembly of the membrane-bound human IgG1 may not yield a fully functional BCR. Thus, it may be preferable to replace the human Cγ1 membrane exons with those from another isotype known to assemble efficiently into a functional BCR. Such exons may include the mouse Cγ1 exons or other murine C membrane exons. Alternatively, the human Cγ2 membrane exons would be expected to function well in the BCR of the mouse because the XenoMouse G2 has high levels of secreted IgG2 and produces high affinity antigen-specific mAbs efficiently. Thus, the human Cγ2 membrane exons could be functionally linked to the human Cγ1 CH1-CH3 exons. The sequence for the membrane exons is known (X52847 for hγ1; AB006775 for hγ2).

Vector Construction

In one embodiment, a targeting vector is generated to introduce only the CH1-CH3 exons into the yH1C YAC. The sequence of all of the human CH1-CH3 as well as introns and flanking DNA is available [See J. W. Ellison et al., *Nucleic Acids Res.*, 13:4071-4079 (1982); J. Ellison et al., Proc. Natl. Acad. Sci. USA, 79:1984-1985 (1982); S. Huck et al., *Nucleic Acids Res.*, 14:1779-1789 (1986); J. Ellison et al., DNA, 1:11-18 (1981) the disclosures of which are hereby incorporated by reference], allowing all restriction sites to be mapped electronically and a targeting vector to be constructed. One such vector would contain 5' homology upstream of human Cγ2 CH1 exon, an expression construct for a positive/negative selectable marker in yeast (URA3), a direct repeat of the 5' targeting homology, sequence containing the human Cγ1 exons CH1-CH3, and 3' targeting homology. This vector would be transfected into yeasts carrying yH1C and homologous recombinants positively selected on plate lacking uracil and then screened by Southern blot hybridization or PCR to test for the loss of human Cγ2 CH1-CH3 exons and the concomitant gain of human Cγ1 CH1-CH3. Once identified, the deletion of the URA3 gene can be selected with 5'-florouracil. Such loss would be expected to occur at high frequency ($10^{-4}$-$10^{-5}$) because of efficient intrachromosomal recombination between direct repeat sequences in yeast. Deletion of the URA3 gene restores a fully human IgH in a configuration functional for class switch recombination and the expression of antibodies. It is obvious that there are other strategies for accomplishing such engineering. Also, there may be motivation to engineer other human Cγ genes, e.g., human Cγ4, into the human Cγ2 locus.

CRE-Lox Mediated Class Switching

The CRE-lox system allows the targeted insertion of DNA into pre-defined sites. Derived from P1 bacteriophage, the CRE recombinase drives intra-DNA or inter-DNA recombination between loxP sites [B. Sauer et al., *New Biologist* 2:441-449 (1990); S. Fukushige et al., *Proc. Natl. Acad. Sci. USA,* 89:7905-7909 (1992); Y.-R. Zou et al., *Current Biol.,* 4:1099-1103 (1994)]. A lox P site (sequence:TA ACT TCG TAT AGC ATA CAT TAT ACG AAG TTA TA (SEQ ID NO: 1)) is introduced into the DNA of a yH YAC. The sequence is positioned 3' of the 3' inverted repeat of the downstream S region, e.g., Sg2, and 5' of the splice acceptor sequence of the CH1 exon of the downstream Cg gene, e.g., Cg1. The lox P site can be inserted directly into the YAC via homologous recombination in yeast, or it can be incorporated into a larger targeting vector, such as the ones described earlier in this description. When incorporating the site into such YAC targeting vectors, the loxP site can be introduced on a PCR primer used for amplifying the targeting homology, e.g., 5' targeting homology, or can be inserted as an oligonucleotide ligated in vitro. As homologous recombination between 2 loxP sites is orientation dependent, it is important to note the orientation in which the first loxP site is inserted into the YAC.

In the second phase, a plasmid vector for insertion of the alternative Cγ gene is generated. At the core of this vector is a cassette carrying the Cg gene to be introduced and a loxP site to enable the introduction: this cassette starts with a lox P site in the same 5'-3' orientation as in the YAC, followed by the DNA upstream of CH1, corresponding to the site of lox P insertion upstream of the Cg on the YAC, and continuing in germline configuration through CH1, with the CH1 exon splice acceptor intact, through downstream of the polyadenylation site 3' of the second membrane exon. For example, an approximately 7 kb Hind III fragment will capture all of the required DNA for all human Cg genes. Alternatively, only the CH1-CH3 exons including appropriate 3' signals for transcription and translation (untranslated region, polyadenylation site) could be used to generate only the secreted form of the mAb. To abrogate possible read through transcription, a eucaryotic transcriptional terminator sequence can be appended downstream of the CH gene on the vector. To facilitate selection of transformants, an expression cassette for a selectable marker such as puromycin or hygromycin may be appended downstream of the CH gene.

Once hybridomas are generated from the transgenic mouse carrying the yH transgene engineered with the lxoP site, CRE-lox mediate class switching can be induced by co-transfecting, e.g., by electroporation or lipofection, the circularized insertion vector, and either purified CRE recombinase or a CRE expression vector. In co-transfected cells, CRE will mediate insertion of the novel CH gene into the locus, where it would be transcribed and spliced in cis to the upstream VHDJH encoding the desired mAb specificity. The transcriptional terminator would preclude run on transcription into the downstream CH gene. If the vector has a selectable marker, then transfected hybridomas can be selected with the appropriate drug, and then pools or individual clones screened by ELISA for mAbs of the desired novel isotype. If the vector lacks a selectable marker, then pools of transfected hybridomas can be screened by ELISA and hybridomas producing the desired isotype can be subcloned from the pool. If the replacement CH gene encodes membrane bound IgH also, then the hybridomas can be screened and sorted by flow cytometry.

In some instances, it may be preferable to possess two different isotypes of a single antigen-specific mAb, with one isotype having one activity, such as ADCC or CML, and the other isotype lacking effector function, but with identical antigen-binding characteristics such as epitope specificity and affinity. This goal could be achieved by molecularly cloning the variable regions of the heavy chain and light chain and then functionally linking them to the appropriate constant regions, followed by transfection into cells for production of the mAb. However, this process can be labor and time intensive. Alternatively, using the CRE-lox process described above, the monoclonal antibody can be efficiently class-switched in vivo in the hybridoma.

Mouse Strains

The following mouse strains are described and/or utilized herein:

Double Inactivated (DI) Strain

The DI strain of mice are mice that do not produce functional endogenous mouse Ig. In preferred embodiments, the DI mice possess an inactivated mouse $J_H$ region and an inactivated mouse Cκ region. The construction of this strain is discussed extensively elsewhere. For example, the techniques utilized for generation of the DI strains are described in detail in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/724,752, filed Oct. 2, 1996. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and PCT Application No. PCT/US96/05928, filed Apr. 29, 1996. The disclosures of each of the above-cited patent and patent applications are hereby incorporated by reference in their entirety. DI mice possess a very immature B-cell development. The mice do not produce mature B-cells, only pro-B-cells. [Green and Jakobovits, *J. Exp. Med.*, 188, pp. 483-495 (1998)].

XenoMouse I Strain

The design, construction, and analysis of the XenoMouse I strain was discussed in detail in Green et al., *Nature Genetics*, 7:13-21 (1994). Such mice produced human IgMκ antibodies against a DI background. The mice showed improved B-cell function when compared to the DI strain of mice which have little to no B-cell development. While XenoMouse I strains of mice mount a sizeable immune response to antigenic challenge, their production of B-cells ws only 20-25% of wild-type mice and they possessed a limited response to antigens. Both characteristics appear to be related to their limited V-gene repertoire.

L6 Strain

The L6 strain is a mouse producing human IgMκ antibodies against a DI background of endogenous mouse Ig. L6 mice contain an inserted human heavy chain and an inserted human kappa light chain. The L6 strain is generated through breeding of a mouse containing a heavy chain insert against a double inactivated background (L6H) and a mouse having a kappa light chain insert against a double inactivated background (L6L). The heavy chain insert comprises an intact approximately 970 kb human DNA insert from a YAC containing approximately 66 $V_H$ segments, starting at $V_H$ 6-1 and ending at $V_H$ 3-65, and including the major D gene clusters (approximately 32), $J_H$ genes (6), the intronic enhancer (Em), Cμ, and through about 25 kb past Cδ, in germline configuration. The light chain insert, yK2, comprises an intact approximately 800 kb human DNA insert from a YAC which contains approximately 32 Vκ genes starting at $V_{K-B3}$ and ending at $V_{K-Op11}$. The 800 kb insert contains a deletion of approximately 100 kb starting at $V_{K-Lp-13}$ and ending at $V_{K-Lp-5}$. However, the DNA is in germline configuration from $V_{K-Lp-13}$ to 100 kb past $V_{K-Op-1}$, and also contains the Jκ genes, the intronic and 3' enhancers, the constant $C_K$ gene, and Kde. [Mendez et al., *Nature Genetics*, 15, pp. 146-156 (1997)]. Furthermore, L6 mice exhibit predominant expression of human kappa light chain, a large population of mature B-cells, and normal levels of IgM$_K$ human antibodies. [Green and Jakobovits, *J. Exp. Med.*, 188, pp. 483-495 (1998)].

XenoMouse IIa Strain:

The XenoMouse IIa mice represent second generation XenoMouse™ strains equipped with germline configuration megabase-sized human Ig loci, against a DI background, such that the mice do not produce functional endogenous Ig. Essentially, the mice are equivalent in construction to the L6 strain, but additionally include the human Cγ2 gene with its entire switch and regulatory sequences and the mouse 3' enhancer in cis. The mice contain an approximately 1020 kb heavy and an approximately 800 kb kappa light chain loci, which include the majority of the human variable region genes, including heavy chain genes (approximately 66 $V_H$) and kappa light chain genes (approximately 32 $V_K$), human heavy constant region genes (μ, δ, and γ) and kappa constant region genes ($C_K$), and all of the major identified regulatory elements. These mice have been shown to access the full spectrum of the variable genes incorporated into their genome. Furthermore, they exhibit efficient class switching and somatic hypermutation, predominant expression of human kappa light chain, a large population of mature B-cells, and normal levels of IgM$_K$ and IgG$_K$ human antibodies. Such mice mount a vigorous human antibody response to multiple immunogens, including human IL-8, human EGF receptor (EGFR), and human tumor necrosis factor-α (TNF-α), ultimately yielding antigen-specific fully human mAbs with sub-nanomolar affinities. This last result conclusively demonstrates XenoMouse™ as an excellent source for rapid isolation of high affinity, fully human therapeutic mAbs against a broad spectrum of antigens with any desired specificity.

As will be appreciated from the above introduction, the XenoMouse II strain appears to undergo mature B-cell development and mount powerful adult-human-like immune responses to antigenic challenge. The L6 strain also appear to undergo mature B-cell development. When XenoMouse II strains, a markedly different B-cell development profile is observed. Owing to this difference, it appears that the quantity and complexity of variable region sequences introduced into the animals are essential to the induction of B-cell maturation and development and the generation of an adult-human-like immune response. Thus, in addition to the strains' utility to generate human antibodies, the strains provide a valuable tool for studying the production and function of human antibodies in the normal immune response, as well as the abnormal response characteristic of autoimmune disease and other disorders.

Variable Region—Quantitative Diversity

It is predicted that the specificity of antibodies (i.e., the ability to generate antibodies to a wide spectrum of antigens and indeed to a wide spectrum of independent epitopes thereon) is dependent upon the variable region genes on the heavy chain ($V_H$) and kappa light chain ($V_K$) genome. The human heavy chain genome includes approximately 95 VH genes of which 41 are functional genes which encode variable regions of the human heavy chain of immunoglobulin molecules. In addition, the human light chain genome includes approximately 40 Vk genes on its proximal end of which 25 are functional which encode variable regions of the human kappa light chain of immunoglobulin molecules. We have demonstrated that the specificity of antibodies can be enhanced through the inclusion of a plurality of genes encoding variable light and heavy chains.

Provided in accordance with the present invention are transgenic mice having a substantial portion of the human Ig locus, preferably including both a human heavy chain locus and a human kappa light chain locus. In preferred embodiments, therefore, greater than 10% of the human $V_H$ and $V_K$ genes are utilized. More preferably, greater than about 20%, 30%, 40%, 50%, 60%, or even 70% or greater of $V_H$ and $V_K$ genes are utilized. In a preferred embodiment, heavy and light chain constructs that include 32 genes from the proximal region of the human $V_K$ light chain genome and/or 66 genes from the $V_H$ portion of the human IgH locus, respectively, are utilized. As will be appreciated, genes may be included either sequentially, i.e., in the order found in the human genome, or out of sequence, i.e., in an order other than that found in the human genome, or a combination thereof. Thus, by way of example, an entirely sequential portion of either the human $V_H$ or human $V_K$ region of the locus can be utilized, or various V genes in either the $V_H$ or $V_K$ genome can be skipped while maintaining an overall sequential arrangement, or V genes within either the $V_H$ or $V_K$ genome can be reordered, and the like. In a preferred embodiment, the entire human loci are inserted in the mouse genome in substantially germline configuration as found in humans. In any case, it is expected and the results described herein demonstrate that the inclusion of a diverse array of genes from the $V_H$ and $V_K$ genome leads to enhanced antibody specificity and ultimately to enhanced antibody affinities.

Such mice preferably further include the entire human $D_H$ region, the entire human $J_H$ region and the human mu constant region, and can additionally be equipped with other human constant regions for the coding and generation of additional isotypes of antibodies. Such isotypes can include genes encoding $\gamma_1$, $\gamma_2$, $\gamma_3$, $\gamma_4$, $\alpha$, $\epsilon$, and $\delta$ and other constant region encoding genes with appropriate switch and regulatory sequences. As will be appreciated, and as discussed in more detail below, a variety of switch and regulatory sequences can be utilized in connection with any particular constant region selection.

The following Table indicates the diversity of antibody combinations that are possible in humans, based strictly on random V-D-J joining and combination with kappa light chains, without consideration of N-addition, deletions or somatic mutation events. Based on these considerations, there are greater than $7 \times 10^5$ possible antibody combinations in humans, of any particular isotype.

TABLE 1

| Region | Heavy Chain | Kappa Light Chain |
|---|---|---|
| Functional Variable "V" | ~41 | 25 |
| Functional Diversity "D" | ≧23 | — |
| Joining "J" | 6 | 5 |
| Combinations (V × D × J) | 5658 | 125 |
| Total Combinations (HC Combinations × LC Combinations) | 7.1 × 10⁵ | |

In connection with a preferred embodiment of the invention, through the inclusion of about 34 functional $V_H$ genes and 18 functional $V_K$ genes in a mouse with a full complement of $D_H$, $J_H$, and $J_K$ genes, the possible diversity of antibody production is on the order of $4.2 \times 10^5$ different antibodies. As before, such calculation does not take into account N-addition or somatic mutation events. Therefore, it will be appreciated that mice in accordance with the invention, such as the L6 and the XenoMouse II strains, offer substantial antibody diversity. In preferred embodiments, mice are designed to have the capability of producing greater than $2 \times 10^5$ different heavy chain V-D-J combinations and kappa light chain V-J combinations, without accounting for N-additions or somatic mutation events.

Variable Region—Qualitative Diversity

In addition to quantitative diversity, quantitative selection of V-genes (i.e., large numbers of diverse V-genes) and/or qualitative selection of V-genes (i.e., selection of particular V-genes) appears to play a role in what we refer to herein as "qualitative diversity." Qualitative diversity, as used herein, refers to diversity in V-D-J rearrangements wherein junctional diversity and/or somatic mutation events are introduced. During heavy chain rearrangement, certain enzymes (RAG-1, RAG-2, and possibly others) are responsible for the cutting of the DNA representing the coding regions of the antibody genes. Terminal deoxynucleotidyl transferase (Tdt) activity, which is responsible for N-terminal additions of nucleotides between the V-D and D-J gene exons is up-regulated. Similar enzymes and others (SCID and other DNA repair enzymes) are responsible for the deletion(s) that occurs at the junctions of these coding segments. Junctional diversity refers to both N-addition events and formation of the complementarity determining region 3 (CDR3). As will be appreciated, CDR3 is located across the D region and includes the V-D and D-J junctional events. Thus, N-additions and deletions during both D-J rearrangement and V-D rearrangement are responsible for CDR3 diversity.

The junctional diversity created by N-additions and CDR3 additions play a clear role developing antibody specificity.

In accordance with the invention, rearranged V-D-J gene sequences show N-addition lengths that are comparable to expected adult-human N-addition lengths. Further, amino acid sequences across the open reading frame (ORF) corresponding to CDR3 sequences show CDR3 lengths that are comparable to expected adult-human CDR3 lengths. Such data is indicative that quantitative variable region diversity and/or qualitative variable region diversity results in human-like junctional diversity. Such junctional diversity is expected to lead to a more human-like antibody specificity.

Variable Region—Affinities

While we have not conclusively demonstrated a direct causal connection between the increased variable region inclusion and antibody specificity, it appears, and it is expected that through providing such diversity, the ability of the mouse to mount an immune response to a wide array of antigens is possible and enhanced. Additionally, such mice appear more equipped to mount immune responses to a wide array of epitopes upon individual antigens or immunogens. From our data it also appears that antibodies produced in accordance with the present invention possess enhanced affinities. Such data includes comparisons between mice in accordance with the invention and the XenoMouse I strains, as well as consideration of the published results of GenPharm International and the MRC. In connection with the XenoMouse I strains, as mentioned above, such mice possessed sub-normal B-cell production and a only limited response to antigens. Such result appeared related in part to the limited V-gene repertoire. Similarly, results reported by GenPharm International and the MRC indicate a limited response to diverse antigens.

Without wishing to be bound to any particular theory or mode of operation of the invention, it would appear that enhanced affinities appear to result from the provision of the large number and complexity of V regions. From our data, the provision of greater numbers and/or selection of qualities of V-gene sequences, enhances junctional diversity (N-additions and formation of complementarity determining region 3 ("CDR3") diversity), which is typical of an adult-human-like immune response, and which play a substantial role in affinity maturation of antibodies. It may also be that such antibodies are more effective and efficient in somatic mutation events that lead to enhanced affinities. Each of junctional diversity and somatic mutation events are discussed in additional detail below.

With respect to affinities, antibody affinity rates and constants derived through utilization of plural $V_H$ and $V_K$ genes (i.e., the use of 32 genes on the proximal region of the $V_K$ light chain genome and 66 genes on the $V_H$ portion of the genome) results in association rates (ka in $M^{-1}$ $S^{-1}$) of greater than about $0.50 \times 10^{-6}$, preferably greater than $2.00 \times 10^{-6}$, and more preferably greater than about $4.00 \times 10^{-6}$; dissociation rates (kd in $S^{-1}$) of greater than about $1.00 \times 10^{-4}$, preferably greater than about $2.00 \times 10^{-4}$, and more preferably greater than about 4.00×10$^{-4}$; and dissociation constant (in M) of greater than about 1.00×10$^{-10}$, preferably greater than about 2.00×10$^{-10}$, and more preferably greater than about 4.00×10$^{-10}$.

Preferably, such mice additionally do not produce functional endogenous immunoglobulins. This is accomplished in a preferred embodiment through the inactivation (or knocking out) of endogenous heavy and light chain loci. For example, in a preferred embodiment, the mouse heavy chain J-region and mouse kappa light chain J-region and C$_K$-region are inactivated through utilization of homologous recombination vectors that replace or delete the region.

Variable Region—B-Cell Development

B-cell development is reviewed in Klaus *B Lymphocytes* (IRL Press (1990)) and Chapters 1-3 of T. Honjo et al., *Immunoglobulin Genes* (Academic Press Ltd. San Diego, Calif. (1989)). Generally, in mammals, blood cell development, including B- and T-cell lymphocytes, originate from a common pluripotent stem cell. The lymphocytes, then, evolve from a common lymphoid progenitor cell. Following an early gestational period, B-cell initiation shifts from the liver to the bone marrow where it remains throughout the life of the mammal.

In the life cycle of a B-cell, the first generally recognizable cell is a pro-pre-B-cell which is found in the bone marrow. Such a cell has begun heavy chain V-D-J rearrangement, but does not yet make protein. The cell then evolves into a large, rapidly dividing, pre-B-cell I which is a cytoplasmically μ$^+$ cell. This pre-B-cell I then stops dividing, shrinks, and undergoes light chain V-J rearrangement becoming a pre-B-cell II which expresses surface IgM, which leave the marrow as immature B-cells. Most of the emerging immature B-cells continue to develop and to produce surface IgD, indicative of their completion of differentiation and development as fully mature immunocompetent peripheral B-cells, which reside primarily in the spleen. [Hardy and Rolink, *Ann. NY Acad. Sci.*, 764, pp. 19-24 (1995); Rolink and Melchers, *Immunol. Lett.*, 54, pp. 157-161 (1996)]. However, it is possible to eliminate the delta constant region and still obtain immunocompetent cells.

B-cell differentiation and development can be monitored and/or tracked through the use of surface markers. For example, the B220 antigen is expressed in relative abundance on mature B-cells in comparison to pre-B-cells I or II. Thus, cells that are B220$^+$ and surface IgM$^+$ (μ$^+$) can be utilized to determine the presence of mature B-cells. Additionally, cells can be screened for surface IgD expression (δ$^+$). Another antigen, heat stable antigen, is expressed by pre-B-cells I and later developmental stages.

TABLE 2

| | Bone Marrow | | | Spleen | |
| --- | --- | --- | --- | --- | --- |
| Marker | pro-pre-B-cell | pre-B-cell I | pre-B-cell II emerging B-cell | immature B-cell | mature B-cell |
| B220 | + | + | + | + | ++ |
| HSA | − | + | + | hi | lo |
| μ | − | − | + | + | + |
| δ* | − | − | − | − | + |

*Assuming the presence of a functional copy of the Cδ gene on the transgene.

Through use of B-cell markers, such as those mentioned above, development and differentiation of B-cells can be monitored and assessed.

We have previously demonstrated that DI mice (mice that do not undergo heavy chain V-D-J rearrangement or light chain V-J rearrangement) do not produce mature B-cells. In fact, such mice arrest at the production of pro-pre-B-cells and B-cells never move from the bone marrow to peripheral tissues, including the spleen. Thus, both B-cell development and antibody production are completely arrested. The same result is seen in mice that are only heavy chain inactivated—B-cell development and differentiation arrests in the bone marrow.

Our XenoMouse I strain produced functional, somewhat mature B-cells. However, the numbers of B-cells, in both the bone marrow and peripheral tissues, were significantly reduced relative to wild type mice.

In contrast, our XenoMouse II strains and L6 strains, unexpectedly possess almost complete B-cell reconstitution. Therefore, in accordance with the invention, we have demonstrated that through the quantitative inclusion or qualitative inclusion of variable region genes B-cell differentiation and development can be greatly reconstituted. Reconstitution of B-cell differentiation and development is indicative of immune system reconstitution. In general, B-cell reconstitution is compared to wild type controls. Thus, in preferred embodiments of the invention, populations of mice having inserted human variable regions possess greater than about 50% B-cell reconstitution when compared to populations of wild type mice.

Isotype Switching by XenoMouse

As is discussed in detail herein, as expected, XenoMouse II mice undergo efficient and effective isotype switching from the human transgene encoded mu isotype to the transgene encoded gamma-2 isotype. As mentioned above, mice in accordance with the invention can additionally be equipped with other human constant regions for the generation of additional isotypes. Such isotypes can include genes encoding γ$_1$, γ$_2$, γ$_3$, γ$_4$, α, ε, δ, and other constant region encoding genes. Alternative constant regions can be included on the same transgene, i.e., downstream from the human mu constant region, or, alternatively, such other constant regions can be included on another chromosome. It will be appreciated that where such other constant regions are included on the same chromosome as the chromosome including the human mu constant region encoding transgene, cis-switching to the other isotype or isotypes can be accomplished. On the other hand, where such other constant region is included on a different chromosome from the chromosome containing the mu constant region encoding transgene, trans-switching to the other isotype or isotypes can be accomplished. Such arrangement allows tremendous flexibility in the design and construction of mice for the generation of antibodies to a wide array of antigens.

It will be appreciated that constant regions have known switch and regulatory sequences that they are associated with. All of the murine and human constant region genes had been sequenced and published by 1989. See Honjo et al. "Constant Region Genes of the Immunoglobulin Heavy Chain and the Molecular Mechanism of Class Switching" in *Immunoglobulin Genes* (Honjo et al. eds., Academic Press (1989)), the disclosure of which is hereby incorporated by reference. For example, in U.S. patent application Ser. No. 07/574,748, the disclosure of which is hereby incorporated by reference, the cloning of the human gamma-1 constant region was predicted based on known sequence information from the prior art. It was set forth that in the unrearranged, unswitched gene, the entire switch region was included in a sequence beginning less than 5 kb from the 5' end of the first γ-1 constant exon. Therefore the switch region was also included in the 5' 5.3 kb HindIII fragment that was disclosed in Ellison et al. *Nucleic Acids Res.* 10:4071-4079 (1982). Similarly, Takahashi et al. *Cell* 29:671-679 (1982) also reported that the fragment disclosed in Ellison contained the switch sequence, and this fragment together with the 7.7 kb HindIII to BamHI fragment must include all of the sequences necessary for the heavy chain isotype switching transgene construction.

Thus, it will be appreciated that any human constant region of choice can be readily incorporated into mice in accordance with the invention without undue experimentation. Such constant regions can be associated with their native switch sequences (i.e., a human $γ_{1, 2, 3, or 4}$ constant region with a human $γ_{1, 2, 3, or 4}$ switch, respectively) or can be associated with other switch sequences (i.e., a human $γ_4$ constant region with a human $γ_2$ switch). Various 3' enhancer sequences can also be utilized, such as mouse, human, or rat, to name a few. Similarly other regulatory sequences can also be included.

As an alternative to, and/or in addition to, isotype switching in vivo, B-cells can be screened for secretion of "chimeric" antibodies. For example, the L6 mice, in addition to producing fully human IgM antibodies, produce antibodies having fully human heavy chain V, D, J regions coupled to mouse constant regions, such as a variety of gammas (i.e., mouse IgG1, 2, 3, 4) and the like. Such antibodies are highly useful in their own right. For example, human constant regions can be included on the antibodies through in vitro isotype switching techniques well known in the art. Alternatively, and/or in addition, fragments (i.e., F(ab) and F(ab')$_2$ fragments) of such antibodies can be prepared which contain little or no mouse constant regions.

As discussed above, the most critical factor to antibody production is specificity to a desired antigen or epitope on an antigen. Class of the antibody, thereafter, becomes important according to the therapeutic need. In other words, will the therapeutic index of an antibody be enhanced by providing a particular isotype or class? Consideration of that question raises issues of complement fixation and the like, which then drives the selection of the particular class or isotype of antibody. Gamma constant regions assist in affinity maturation of antibodies. However, the inclusion of a human gamma constant region on a transgene is not required to achieve such maturation. Rather, the process appears to proceed as well in connection with mouse gamma constant regions which are trans-switched onto the mu encoded transgene.

EXAMPLE 1

YAC Vectors for Murine γ1-Human γ4 or Murine γ1-Human γ1

Figure 5:
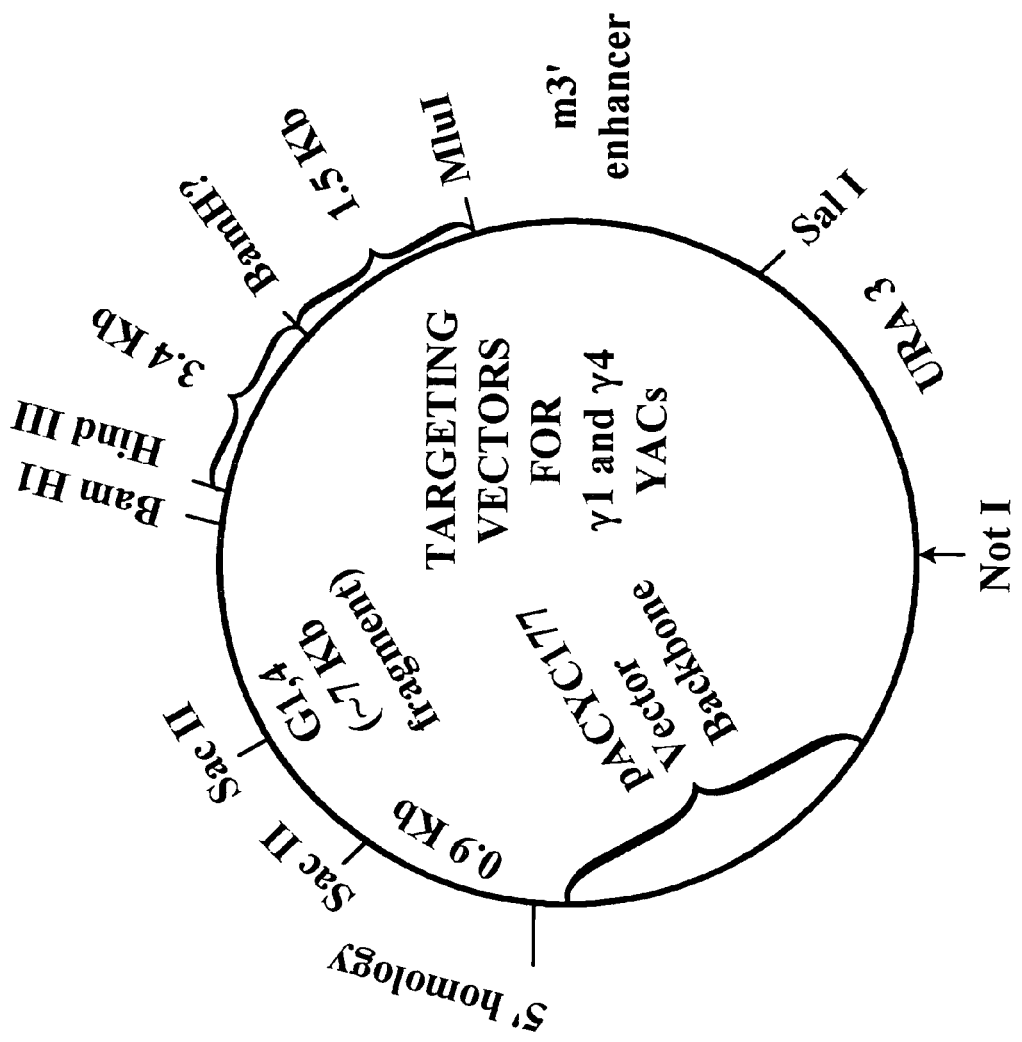
FIG. 5 is a schematic diagram of the targeting vectors (TV1 and TV4) for retrofitting yH1C to yHG1 and yHG4 YACs.

Replacement vectors for targeting the parent YAC yH1C to replace the human γ2 switch element and human CH γ2 exons with the murine γ1 switch element and either the human Cγ1 exons or the human Cγ4 exons were prepared (FIG. 1). The vectors were designated as pMuShu1 and pMuShu4 (FIG. 5). The vectors were constructed using a low copy number cloning vector known as pACYC177. This vector pACYC177 is available from New England Biolabs, Inc., Beverly, Mass. and the sequence can be found in Genbank sequence database under the sequence accession number Genebank #X 06402. A low copy number origin of replication is useful to prevent unwanted rearrangements or deletions of the plasmid DNA when propagated in *E coli*.

The first step was to introduce a linker into pACYC177 in order to accommodate the elements needed for the targeting vector. The linker contained the following restriction sites: NheI-SalI-SmaI-NotI-EcoRI-XbaI-SacI-BamHI.

The nucleotide sequence of the linker (SEQ ID NO: 2) is shown below:

5' - cta gtc gac aaa tat tcc ccg ggc ggc cgc tta cgt atg aat tca gcg cgc ttc tag aac tcg agt gag ctc The nucleotide sequence of the complimentary strand of the linker (SEQ ID NO: 3) is shown below:

5' - gat cga gct cac tcg agt tct aga agc gcg ctg aat tca tac gta agc ggc cgc ccg ggg aat att tgt cga Restriction Enzymes Unless otherwise stated all restriction enzymes were purchased from New England Biolabs Inc. (Beverly, Mass.). Furthermore, all restriction digestion conditions were standardized according to the following conditions: 1 microgram of DNA was digested in 20 μl of the appropriate restriction buffer and using 5 units of restriction enzyme for 1 hour. Restriction buffers are specified by the manufacturer for particular enzymes and the compositions are provided in the product catalog from New England Biolabs Inc. (Beverly, Mass.).

To introduce the linker, pACYC177 was digested with restriction enzymes NheI/BamHI according to the manufacturer's instructions. The linker as shown above was ligated with a 2208 bp fragment of pACYC177 isolated on an agarose gel and purified using Geneclean kit (Bio 101) (Vista, Calif.). This process removed only non-essential regions of the vector including NheI and BamHI restriction sites.

The next step was to introduce the yeast URA3 gene, with its promoter and coding sequences as a marker for selection of yeast cells containing the YAC. A DNA 1971 bp fragment of the URA3 gene containing the promoter and coding sequence was obtained from pYAC4, which is available from the American Type Culture Collection (ATCC) catalog no. 67379 (Manassas, Va.) and the sequence can be obtained from Genebank using accession no. #U01086. The URA3 fragment also provides sufficient 3' homology for targeting. The plasmid pYAC4 was digested with the restriction enzymes, SalI and MscI, according to the manufacturers instructions. Likewise, the vector-linker combination, pACYC177/linker, was digested with SalI and SmaI according to the manufacturers instructions. Subsequently, the two restriction nucleotide digested DNAs pACYC177 and URA3 were ligated together to produce Int 2.

The next step was to introduce the beta-galactosidase gene (beta Gal) by first digesting Int 2 with XbaI and SacI according to the manufacturers instructions. The beta Gal gene was cloned from the vector pGK beta Gal which can be obtained from Cell Genesys, Inc. (Foster City, Calif.). The DNA pGK beta Gal was digested with the restriction enzymes, XbaI and SacI. Linearized Int 2 and the 2553 kb fragment from pGK beta Gal were ligated together to produce the next intermediate called Int 3.

The above beta Gal expression construct is incomplete. The missing portion of beta Gal is obtained by digesting the pGK beta Gal plasmid with restriction enzyme SacI and NcoI. The 1165 kb fragment from the pGK beta gal digestion was isolated by agarose gel eletrophoresis, wherein the fragment was excised from the ethidium bromide stained gel and purified like described above using a Geneclean kit (Bio 101) (Vista, Calif.). Similarly, Int 3 was digested with the restriction enzyme SacI, according to the manufacturers instructions. The linearized Int 3 was isolated by agarose gel eletrophoresis. The 1165 bp fragment from pGK beta gal and the linearized Int 3 were ligated together using the enzyme T4 DNA ligase, purchased from New England Biolabs, Inc. The DNA fragment was reisolated and then treated with Klenow fragment to blunt the ends. The linearized DNA was circularised using the enzyme NcoI which blunt ligates to SacI blunt ends to produce Int 4.

Introduction of 5' Homology

The region of 5' homology for targeted recombination was isolated from the sequence of A-287-C10 YAC by rescue of the 3' end and had been previously cloned into plasmid ppK-Mlc [See Mendez et al., *Nature Genetics* 15:146-156 (1997)]. The A287-C10 YAC was isolated by screening DNA pools from the Washington University human YAC library (Washington University, St. Louis, Mo.) using PCR primers for the human $V_H6$ gene. Isolation and characterization of the A287-C10YAC was described in detail in International Patent application WO 94/02602, by Kucherlapati et al., published on Feb. 3, 1994, and that disclosure is hereby incorporated by reference.

Int 4 was digested with the restriction enzymes NotI and SnaBI and then treated with Calf Intestine Phosphatase as follows: 1 microgram of DNA in 20 microliters of restriction digest reaction, 5 units of calf intestine phosphatase (New England Biolabs., Beverly, Mass.). The enzyme and DNA were incubated for 30 minutes at 30° C., then heated to 65° C. for another 30 minutes to denature the phosphatase. The vector ppKMlc was digested with the restriction enzyme, EcoRI, and then treated with Klenow Fragment to create a blunt end to remove the EcoRI site. The linearized ppKM1c was isolated and digested with the restriction enzyme NotI, according to the manufacturers instructions. A fragment of approximately 1 kb 5' homology was isolated. Next, the 1 kb fragment was ligated together with the NotI and SnaBI digested Int 4. This DNA preparation was named Int 5.

The γ1 and γ4 CH1, Hinge, CH2, and CH3 coding exons, transmembrane exons and approximately 3 kb of downstream sequence (~7 kb each) were introduced into the replacement vectors through two intermediate DNAs derived from pBR322.

First, pBR322 was digested with Hind III, treated with Calf Intestine Phosphatase (CIP) and ligated with the approximately 7 kb Hind III fragment containing the γ1 sequences from P1 clone #1737 (G1). P1 phage clone was purchased from Genome Systems, Inc. (St Louis, Mo.). This resulted in intermediate plasmid pCG12.

The second intermediate was constructed by digesting pBR322 with the restriction enzymes, HindIII and BamHI. The 3986 kb fragment was treated with calf intestine phosphatase and ligated with approximately 7 kb HindIII/BamHI fragment containing the human γ4 sequences from BAC clone #176E10, purchased from Genome Systems, Inc. (St. Louis, Mo.). This intermediate plasmid was called pCG43.

In order to complete construction of targeting vectors, a new linker was cloned into the XbaI restriction site of Int 5. The linker had the following restriction sites: XbaI•kill-MfeI-SspI-HindIII-SnaBI-BclI-XhoI-M1uI-Xba•kill. Int 5 with the linker cloned into it was called Int6. The linker sequence ID NO: 4)is shown below:

5' cta ggc aat tga taa tat taa gct tta cgt atc tga tca tcc tcg aga cgc gtg

Complementary strand sequence (SEQ ID NO: 5):

5' cgt taa cta tta taa ttc gaa atg cat aga cta gta gga gct ctg cgc acg atc

The Linker was oriented in Int 6 as such:
A287—SnaBI(ex)-EcoRI-BssHII-XbaI(ex)-MfeI-HingIII-Bc1I-XhoI-M1uI-pGK-beta Gal The restriction site XbaI•kill indicates that the particular XbaI site will be eliminated upon ligation into the larger DNA. The linker is conveniently designed so that it can ligate into an XbaI site but the site does not survive the ligation. The particular XbaI site which contained the linker was determined by first cloning the linker and then digesting the DNA with the following pairs of restriction enzymes separately: NotI and HindIII; XbaI and SphI; and MluI and SphI. Introduction of the linker eliminates one XbaI site. The position of the linker in Int 6 was determined by the distance between the newly introduced Hind III site and the NotI site which was present in Int 5.

Cloning of Mouse γ1 Switch Region:

The plasmid EH10 was obtained from the University of Michigan and is a pBR3222 based plasmid containing a murine γ1 switch region on a HindIII/EcoRI fragment [M. R. Mowatt et al., *J. Immunol.* 136:2647-2683 (1983)]. The plasmid was digested with the restriction enzymes EcoRI and HindIII and the 10 kb fragment containing the mouse γ1 switch was isolated and purified as above.

Construction of pMSL4

Construction of pMSL1 involved a three way ligation. The first element was the 10 kb fragment containing the mouse γ1 switch was isolated from EcoRI and HindIII digested EH10 as described above. The second element was pBR322 digested with BamHI and EcoRI. The final element was the pBR322 based plasmid, pCG43, containing human γ4 on an approximately 7 kb HindIII and BamHI fragment. All three were ligated together to create pMSL4.

Construction of pMSL1

Construction of pMSL1 also involved a three way ligation. The first element was the 10 kb fragment containing the mouse γ1 switch was isolated from EcoRI and HindIII digested EH10 as described above. The second element was pBR322 digested with EcoRI and BamHI. The final element was pBR322 based plasmid pCG12 containing approximately 7 kb fragment of human γ1 which was modified by introduction of Hind III kill-HamHI linker into HindIII site on 3' end of the 7 kb fragment. Thusly modified plasmid after double digest with BamHI and HindIII releases 7 kb HindIII/BamHI fragment which is subsequently used in three piece ligation.

Mouse 3' Enhancer

We isolated the 0.9 kb core part of the enhancer by StuI restriction digestion from the 4 kb MluI fragment of the pIBgamma2 targeting vector containing the murine 3' enhancer (HSIg2) cloned into pIB [M. J. Mendez et al., *Nature Genetics,* 15:146-156 (1997)].

We digested Int 6 with the restriction enzyme XhoI, followed by treatment with the Klenow fragment to create blunt ends. We ligated the resulting linearized Int 6 with the 0.9 kb StuI fragment of murine 3' enhancer to create Int 7. We verified the cloning reaction by performing restriction digestion on sample clones with using EcoRI. In addition, we confirmed the desired orientation of the fragment by digests with NcoI; NcoI and HindIII; and HindIII and PvuII and the known restriction map of the 0.9 bp Stu I fragment.

We introduced another linker into plasmid Int 7. We digested Int 7 with MfeI and SnaBI (double digest), followed by treatment with calf intestine phosphatase. Next, we introduced the following linker by performing a ligation reaction and creating intermediate Int 8. The restriction sites inserted by the linker into Int 7 are as follows: MfeI•kill-HindIII-SnaBI-BclI-BglII-Bam HI-BglII-NheI•kill. Again, MfeI•kill indicates that the MfeI site was eliminated upon ligation into the larger DNA.

The nucleotide sequence of the linker (SEQ ID NO: 6):

```
5' aat taa gct tgt acg tac tga tca aga tct gga tcc
aga tct
```

The nucleotide sequence of the complementary strand (SEQ ID NO: 7):

```
5' aga tct gga tcc aga tct tga tca gta cgt aca
agt t
```

Targeting Vectors

The complete targeting vectors were constructed by digesting Int8 with the restriction enzymes SceI and HindIII, followed by treatment with calf intestine phosphatase. The plasmids pMSL1 and pMSL4 were partially digested with the restriction enzymes SceI and HindIII. A 17 kb fragment was isolated by polyacrylamide gel electrophoresis. The purified 17 kb fragment was ligated with Int 8 to create the final targeting vectors as shown in FIG. 5.

EXAMPLE 2

Targeting of γ1 or γ4 Constructs on yH1C YAC

The TV1 or TV4 vectors (5 ug DNA) were linearized by digestion with the restriction enzyme NotI (FIG. 5). The DNA was purified by phenol extraction followed by phenol/chloroform extraction. Next, the DNA was precipitated with ethanol and then used to a transform a yeast clone containing the yHIc YAC using a LiAc transformation protocol. [See Schiestl, R. H. et al., Curr. Genet. 16,339-346 (1989)]. Transformants were plated onto SC-URA agar media plates and incubated at 22° C. until colonies appeared or approximately 5-6 days. SC-URA plates contain a media for growth of yeast which lacks uracil and therefore selects for yeast colonies that can produce their own uracil. Similarly, SC-LYS plates contain a media for growth of yeast which lacks lysine and selects for yeast colonies that can produce their own lysine. The resulting colonies were repicked onto SC-URA plates and on SC-LYS plates—for genetic testing—to look for the loss of the LYS marker. Only clones which grew on SC-URA and did not grow on SC-LYS were grown in YPDA media for 48 hours at 22° C. YAC DNA was isolated and analyzed by polymerase chain reaction (PCR) to evaluate whether the desired isotype replacements occurred as expected. In this case, human γ1 or γ4 CH exons should have replaced human γ2 CH coding exons (FIG. 1). The yeast media used here was prepared from supplements obtained from BIO 101 (Vista, Calif.).

PCR Primers used for this assay are as follows:

```
HG1: 5' cac acc gcg gtc aca tgg c      (SEQ ID NO: 8)
HG3: 5' cta ctc tag ggc acc tgt cc     (SEQ ID NO: 9)
```

The PCR reaction consisted of 35 cycles of the following: 94° C. for 15 seconds followed by 60° C. for 45 seconds and then 72° C. for 90 seconds per cycle. HG1 primer was positioned at nucleotide 181 on consensus human Cγ1, Cγ2, Cγ4 alignment and primer HG3 was positioned at nucleotide 994 of this alignment. These primers will amplify DNA from Cγ1, Cγ2, and Cγ4 isotypes.

Due to restriction site polymorphism in the human Cγ genes, the particular isotype of the template DNA could be determined by restriction digestion of the PCR products to yield unique sets of DNA fragments. For example, the restriction enzyme PvuII restricts the PCR product into two fragments of 621 bp and 196 bp when Cγ2 DNA is the template for the PCR products, but does not cut the product if Cγ1 or Cγ4 is the template. Similarly, the restriction enzyme Eco47III restricts the PCR product into two fragments of 438 bp and 379 bp when Cγ1 is obtained. Finally, the restriction enzyme BglII restricts the PCR product into two fragments of 686 bp and 125 bp when Cγ4 is obtained. In this way all three isotypes of IgG could be distinguished.

In the next level of characterization, all yeast clones which exhibited correct genetics as well as the desired IgG isotype were further screened by Southern blot assay [J. Sambrook et al. Molecular Cloning: A Laboratory Manual, Chapter 9, pages 31-45, Cold Spring Harbor Laboratory Press (1989)]. A 5 microgram sample of DNA for each clone was digested overnight with the restriction enzymes Hind III, EcoRI and Bam HI. yHIC YAC DNA, which served as the original target on the replacement vectors was used as control. The digested DNAs were separated on 0.8% agarose gel, stained with ethidium bromide and photographed and then transferred onto nylon membrane (Gene Screen Hybridization Membrane, NEN Life Sciences). Next, the YAC candidates were checked on Southern blots using hybridization probes from the following Ig genes: D, mu, J, delta, murine 3' enhancer, Cg1,4,V1-6. [See M. J. Mendez et al., Genomics 26, 294-307 (1995); M. J Mendez et al., Nature genetics vol 15, 146-156 (1997) (V3 probe)]

The following probes were used for Southern blotting:

```
HG1: CAC ACC GCG GTC ACA TGG C       (SEQ ID NO: 8)
HG3: CTA CTC TAG GGC ACC TGT CC      (SEQ ID NO: 9)
```

These primers will amplify ~820 bp fragment for gamma 1,2 and 4. Either one can be used as a probe as they are highly homologous.

To amplify VH5 following primers were used:

```
                                      (SEQ ID NO: 10)
VH5A: 5' GTC GAC GGG CTC GGG GCT GGT TTC TCT (SEQ ID NO: 11)
VH5B: 5' GGG CCC TGA TTC AAA TTT TGT GTC TCC
```

For HPRT following primers were used:

```
                                     (SEQ ID NO: 12)
    REP3: 5' CTG GAG TCC TAT TGA CAT CGC C (SEQ ID NO: 13)
    REP4: 5' GGT TCT TTC CGC CTC AGA AGG
```

And, finally, to amplify Cmu following primers were used:

```
Jm1:
5' GCT GAC ACG TGT CCT CAC TGC    (SEQ ID NO: 14)

Jm4:
5' CCC CAG TTG CCC AGA CAA CGG    (SEQ ID NO: 15)
```

Finally, we confirmed the general structural integrity of the YACs using CHEF gel pulse-field gel electrophoresis (CHEF DR-II, Bio Rad Life Sciences, Hercules, Calif.).

We designated the YAC encoding Cγ1 as yH2Bm and the YAC encoding human Cγ4 as yH2Cm.

EXAMPLE 3

Construction of Vectors for Retrofitting yH1C YAC to γ1 (TV G1) and γ4 (TV G4)

Figure 6:
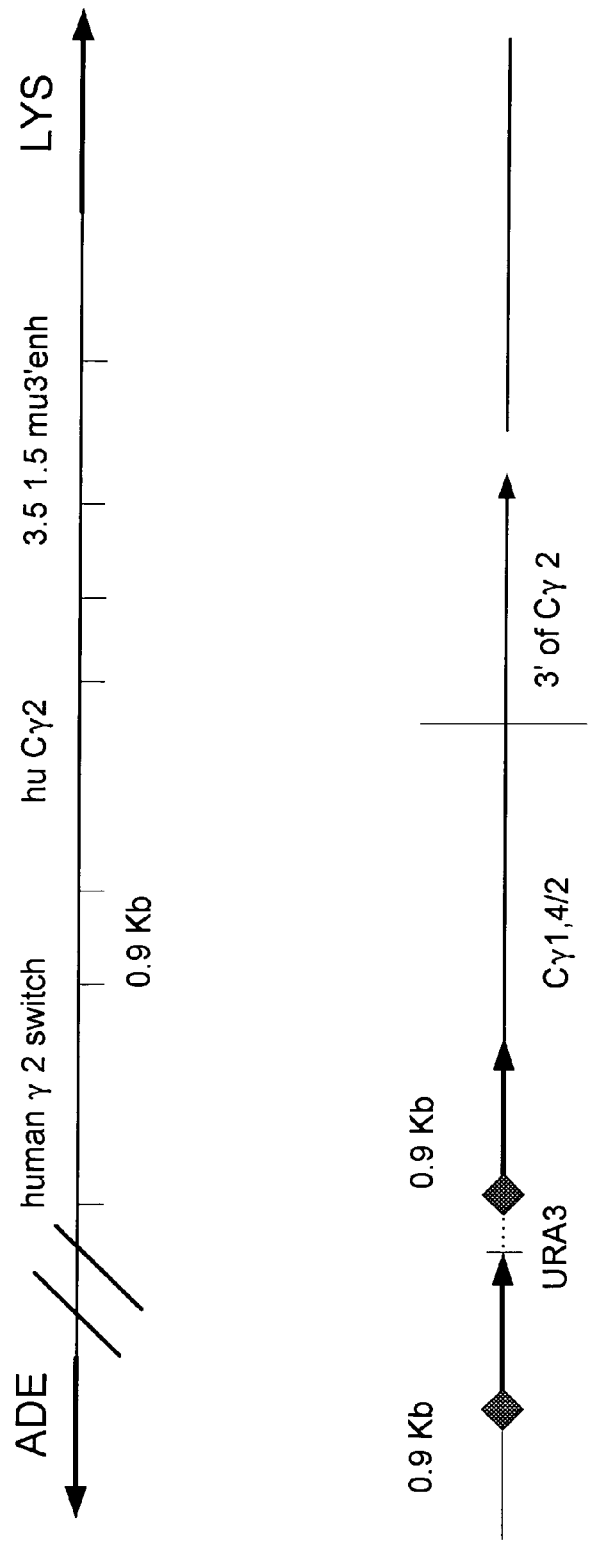
FIG. 6 illustrates the construction of the targeting vectors for retrofitting yH1C to yHG1/2 and yHG4/2 YACs.

Vector construction for preparing the targeting vectors to retrofit the yH1C YAC to yHG1 and yHG4 is schematically shown in FIG. 6. The targeting vectors were built on a backbone of pACYC177 (Genebank #X06402) available from New England Biolabs Inc. (Beverly, Mass.). We introduced a linker into pACYC177 to facilitate cloning of a murine 3' enhancer. We called the pACYC177 vector containing the linker Int 9. The arrangement of restriction enzyme cloning sites in the linker was as follows: HindIII-SalI-MluI-PacI-FseI-HindIII. The linker nucleotide sequence (SEQ ID NO: 16) is shown below:

```
5' agc ttg tcg aca cgc gtt aa tta agg ccg gcc a
```

The nucleotide sequence of the complementary strand (SEQ ID NO: 17):

```
5' agc ttg gcc ggc ctt aat taa acg cgt gtc gac a
```

We cloned the murine 3' enhancer from the yH1C targeting vector as an approximately 4 kb MluI fragment. The 4 kb enhancer fragment was cloned into the MluI site of pACYC177 modified with the linker shown above and the DNA is called Int 10. Proper orientation of murine 3' enhancer was determined by digesting prospective clones with the restriction enzymes NgoMI and EagI.

Amplification of a 5' Homology Region

A region of 5' homology was obtained by PCR amplification of the relevant portion of pIBgamma2 targeting vector [M. R. Mowatt, et al., J. Immunol. 136:2647-2683 (1983)]. The nucleotide sequence of the primers used for amplifying the 5' homology region were [See also Genbank Accession no. M12389]:

```
                                          (SEQ ID NO: 18)
Primer 1: 5' tgg tgg ccg aga agg cag gcc a (SEQ ID NO: 19)
Primer 2: 5' ccg cgg gca tgc aac ttc gta taa tgt
          atg cta tac gaa gtt att gtg gga cag agc
          tgg gcc cag g
```

Primer 2 contains SacII and SphI sites as well as a lox p element. The 5' homology region was PCR amplified using the following PCR conditions: 20 cycles of 94° C. for 3 seconds, followed by 55° C. for 30 seconds, and then 72° C. for 60 seconds. The region was then sequenced after cloning it into TA-TOPO vector. TA-TOPO is available from Invitrogen, Inc. (Carlsbad, Calif.).

The primers for 5' homology sequencing are shown below:

```
seq1:      gtc tgg ccc ctc tgc tgc    (SEQ ID NO: 20)

seq2:      cac cca taa aag gct gga    (SEQ ID NO: 21)

rev.       acg gct cat gcc cat tgg    (SEQ ID NO: 22)
seq1:

rev.       tag tga gtg ggc ctg act    (SEQ ID NO: 23)
seq2:
```

We compared the resulting sequence to the human switch γ2 sequence (Genebank #U39934) and determined that it is identical.

Cloning of γ4 Coding and 3' Homology Regions

We obtained human γ4 coding exons and a region of 3' homology by performing partial enzymatic digestion of the plasmid pCG43 using the restriction enzyme SacII. We then digested plasmid pGS43 with the restriction enzyme BamHI and we cloned a purified approximately 7 kb fragment into the TA vector containing 5' homology. We called this intermediate recombinant DNA molecule IntI G4.

IntI G4 was digested with BamHI, treated with calf intestine phosphatase and then the vector were isolated using agarose gel electrophoresis. The isolated vector was ligated as described before with 3.4 kb BamHI fragment from pIB gamma2. Orientation of the insert was determined by double digest NotI/Hind III. The HindIII site was determined to be at the 5' end of 3.4 kb BamHI fragment as determined by the sizes of fragments after digests.

Next we needed to determine orientation of the linker in pACYC177/enhancer plasmid. This was done by preparing a panel of double digestions of pACYC177/linker with SmaI and with one of each of the following second enzymes, SalI, MluI, PacI and FseI. Linker orientation was determined by sizes of resulting fragments.

The positions of restriction sites in pACYC177/enhancer plasmid is as follows: ClaI/SmaI (pACYC177)-HindIII-FseI-PacI-MluI-((enhancer:PstI-PvuII-EcoRI-NcoI-NheI-ApaI))-MluI-SalI)-PfmII (pACYC177).

The next step was to clone URA 3 gene into pACYC177/enhancer plasmid. The purpose of this is to retrofit the targeting vector with a selectable yeast marker, as well as 3' homology to drive homologous recombination. In order to clone URA3 gene, Int 2 (constructed for original TV1 and 4, described in Example 1) was digested using SacII/SalI. Similarly, the pACYC177/enhancer plasmid was digested with SacII/SalI. 3.8 kb fragment from Int 2 digestion and a 5 kb fragment from pACYC177/enhancer were isolated on agarose gel electrophoresis and ligated together. The resulting plasmid contains enhancer and URA3 gene in pACYC177 backbone. The next step was to introduce two more linkers into Int1 G4 with cloned 3.4 kb Bam HI fragment. The resulting intermediate was called Int 2 G4.

The Linkers were as follows: NotIkill-FseI-NotIkill and Linker sequences:

```
    GGCCATGGCCGGCCAT        (SEQ ID NO: 24)

TACCGGCCGGTACCGG        (SEQ ID NO: 25)
```

The second linker had the following restriction sites: BamHI-KpnI-EcoRV-MfeI-FseI-SfiI-BamHIkill:

```
                                            (SEQ ID NO: 26)
    GATCCGGTACCGATATCCAATTGGGCCGGCCGGCCATATAGGCCT (SEQ ID NO: 27)
    GCCATGGCTATAGGTTAACCCGGCCGGCCGGTATATCCGGACTAG
```

The purpose of introducing linker 1 was to provide an FseI site for the final cloning step, as well as eliminating one of NotI sites. In addition, this leaves the final targeting vector with a unique NotI site, which was used to linearize the targeting vector before transformation. The second linker was used to clone the last fragment needed to restore the complete downstream region of yH1C YAC, a 1.5 kb BamHI/EcoRI fragment.

Linker 2 was introduced via partial digest with Bam HI. IntI G4 (with cloned 3.4 kb BamHI fragment) was partially digested with BamHI and the partial digest was isolated on agarose gel as a 13 kb fragment. The 13 kb fragment was treated with calf intestine phospohatase and ligated with linker. The position of the linker and its orientation (whether it went into correct BamHI site at 3' end of 3.4 BamHI fragment) was determined by digesting clones with MfeI and NotI (double digest). The MfeI site is introduced with a linker and the NotI site is present in the vector. Relative fragment sizes permit allowed identification of the position and orientation of the linker. The plasmids retrofitted with linker are now Int 3 G1 and Int 3 G4.

The next step was to clone into Int 3 G4 plasmid, a 1.5 kb fragment obtained by BamHI/EcoRI double digest of pIBgamma2 plasmid. The 1.5 kb fragment was cloned into BamHI partial digest/MfeI digest of Int 3 G4. Since it was directional cloning, no orientation determination was needed in this step. The resulting plasmid was called Int 4 G4.

The next step was to introduce the linker with the restriction sites NotIkill-FseI-NotIkill. Int 4 G4 was digested with NotI, treated with calf intestine phosphatase, isolated on agarose gel and ligated with the linker. The resulting plasmid was called Int 5 G4. Again, there was no need to determine linker orientation in this step. As a result, a unique Not I site was eliminated and one FseI site was added. The purpose of introducing the FseI site was to allow cloning of a fragment spanning from 5' homology region to the 1.5 kb fragment to pACYC177/enhancer/URA3 plasmid.

The final cloning step was a partial digest of Int 5 G4 with FseI, followed by isolation of a 13 kb fragment on agarose gel and ligation into the unique FseI site of pACYC177/enhancer/URA3. The orientation of this insert was determined by a double restriction digest with NotI/FseI. The final targeting vectors were called TV G4.

To construct the TVG1 targeting vector to retrofit the yH1C YAC with human Cγ1 coding exons and a a region of 3' homology, we use the procedure described above for the construction of TV G4. We obtain the Cγ1 coding exons and 3' homology region from plasmid pCG12.

EXAMPLE 4

Figure 3:
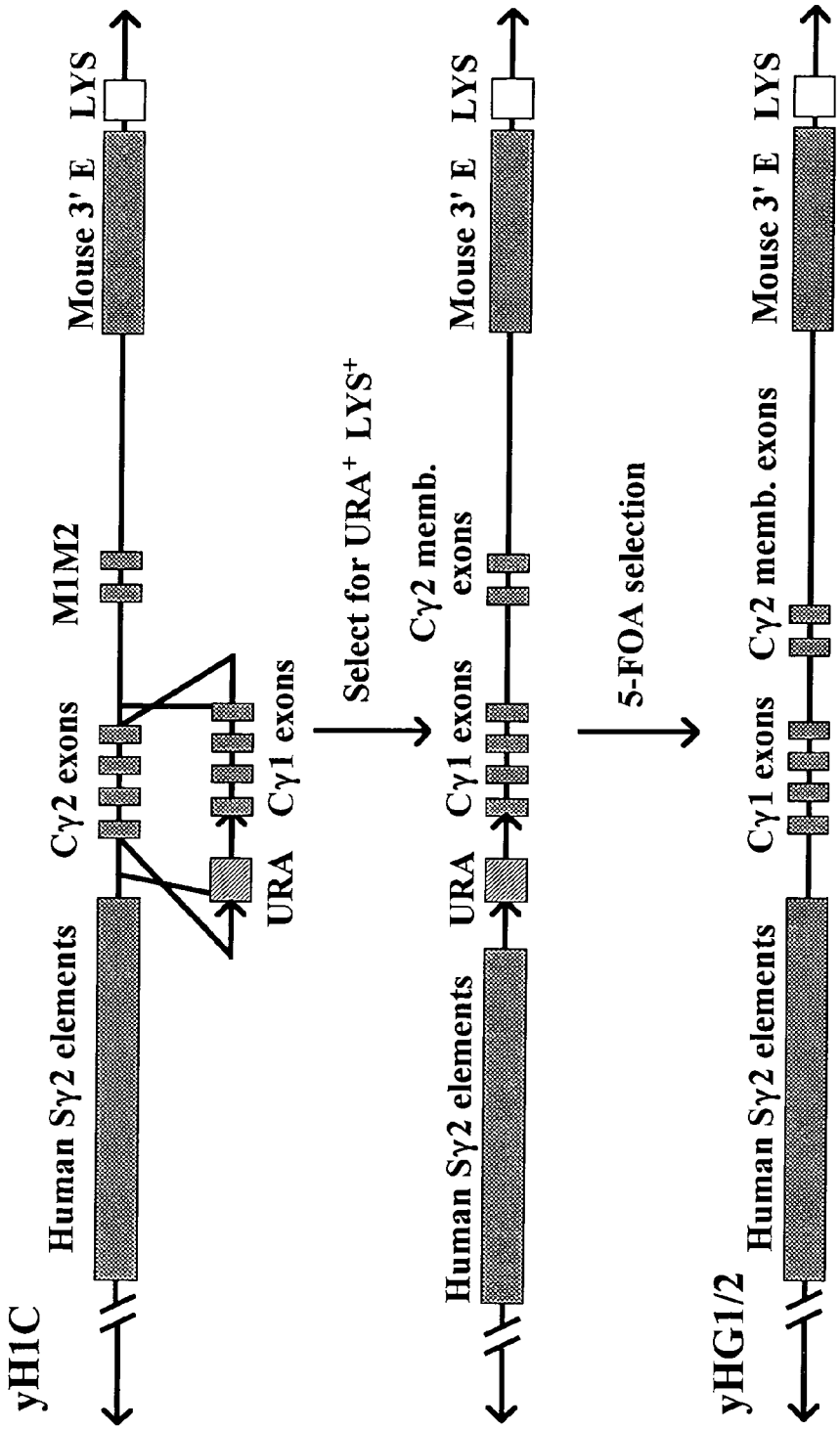
FIG. 3 is a schematic depiction of the yH1C and yHG1/2 yeast artificial chromosomes (YACs).

Construction of Targeting Vectors TV G1/2 and TV G4/2 for Targeting of yH1C YAC for Non-cognate Switching Next, we constructed a vector, TV G1/2, which has a chimeric construct of human γ1 CH coding exons attached downstream of 5 kb of human switch γ2 region DNA (FIG. 3). In addition, this vector contains human γ2 transmembrane exons located 3' of the γ1 CH coding exons (FIG. 3). The vector is based on pACYC177 vector, which is available from New England Biolabs (Beverly, Mass.). We constructed the vector, which we call TV G1/2, using the following procedure:

1. First, 5 ug of pIBgamma2 was digested with the restriction enzymes, HindIII and BamHI, and a 6.5 kb fragment was isolated on an agarose gel. The vector, pIBgamma2, contains 22 kb of human genomic DNA with γ2 flanked by two EcoRI restriction enzyme sites and was previously used to generate yH1C. The 6.5 kb fragment was then ligated into the pCR™2.1 vector from Invitrogen, Inc. (Carlsbad, Calif.). pCR2.1 was prepared by digesting 1 μg of plasmid with BamHI/HindIII and treating with calf intestine phosphatase and then isolated on an agarose gel.

2. The resulting plasmid (6.5 kb fragment+pCR™2.1 vector) was subjected to partial digestion with restriction enzyme XmnI followed by digestion with the restriction enzyme HindIII. The digestion with XmnI occurs 75 bp upstream of the γ2 stop codon. Therefore, the 4th exon of the γ1/γ2 chimeric gene initially contains 75 bp of γ2 in addition to the two 3' γ2 membrane exons. The coding region fo γ1 and γ2 are identical throughout this 75 bp region and there is no effect.

3. Next, 5 ug of pCG12 was digested with the restriction enzymes HindIII and XmnI and a 1.7 kb fragment was isolated by agarose gel electrophoresis. The vector pCG12, which is described in Example 1, contains approximately 7 kb of human γ1.

4. The 1.7 kb HindIII/XmnI fragment comprising most of the coding sequences of γ1 obtained from pCG12 was ligated into the HindIII/XmnI partially digested vector (6.5 kb fragment+pCR™2.1 vector) described in step 2.

5. The resulting plasmid contains chimeric sequences of coding regions of γ1 attached to a downstream region of γ2 that contains transmembrane exons. We verified the composition of the plasmid by restriction digestion with Eco47III.

6. The pCR™2.1 vector having cloned 5' homology, described in Example 3, was digested with SacII and BamHI. Likewise, we digested the plasmid described in step 5 with SacII and Bam HI (double digest) and cloned an approximately 5 kb fragment from the plasmid into the pCR2.1 vector with the 5' homology. Then we digested the resulting vector with SacII and SacII and cloned into this site fragments obtained from the vector described in step 5). We determined the Orientation of the SacII insert by SphI digests. The resulting plasmid contained chimeric γ1/γ2 $C_H$ exons downstream from a region of 5' homology in a pCR2.1 vector. We called this vector TA G1/2, indicating that it is derived from pCR2.1, known as TA cloning vector, and contain chimeric γ1/γ2 $C_H$ exons.

7. We retrofitted the pCR™2.1 vector with cloned 5' homology described in step 6 with the yeast selectable marker, URA3, gene as follows:

a. We obtained the URA3 gene by digesting Int 2 (described in Example 1) with SalI. The products of the SalI digestion are subjected to an additional reaction with Klenow fragment to create blunt ends. These products are consecutively digested with SacI.
b. The pCR™2.1 vector produced in step 6 was digested with BamHI, then blunted with Klenow fragment and further digested with SacI.
c. The URA3 gene obtained in 7(a) was ligated into the pCR™2.1 vector prepared as in 7(b). The resulting vector contains a 5' homology region with a downstream URA3 gene, flanked by NotI sites (one from the linker in Int2 and another originally present in pCR2.1).

8. We excised the NotI fragment from the plasmid produced in step 7 and cloned it into the NotI site of Int 1 (also used for TV1 and 4 cloning). We determined the correct orientation of the NotI fragment by using an EcoRI digest. The resulting plasmid, which we designated Int 3, has a 5' homology region with a URA3 gene downstream in the low copy origin background (pACYC177).

9. To finish construction of the final targeting vector for the G1/2 chimeric YAC, we partially digested the vector having the cloned 5' homology and G1/2 chimeric IgG constant region in the pCR2.1 background (produced in step 6) with EcoRI restriction enzyme and subsequently recut with SacI restriction enzyme. We isolated an 8 Kb fragment containing the 5' homology and the chimeric G1/2 IgG constant region and cloned it into EcoRI and SacI sites of Int 3, which resulted in the TV G1/2 targeting vector. There was no need to determine the insert orientation, since we introduced the fragment by directional cloning.

Figure 7:
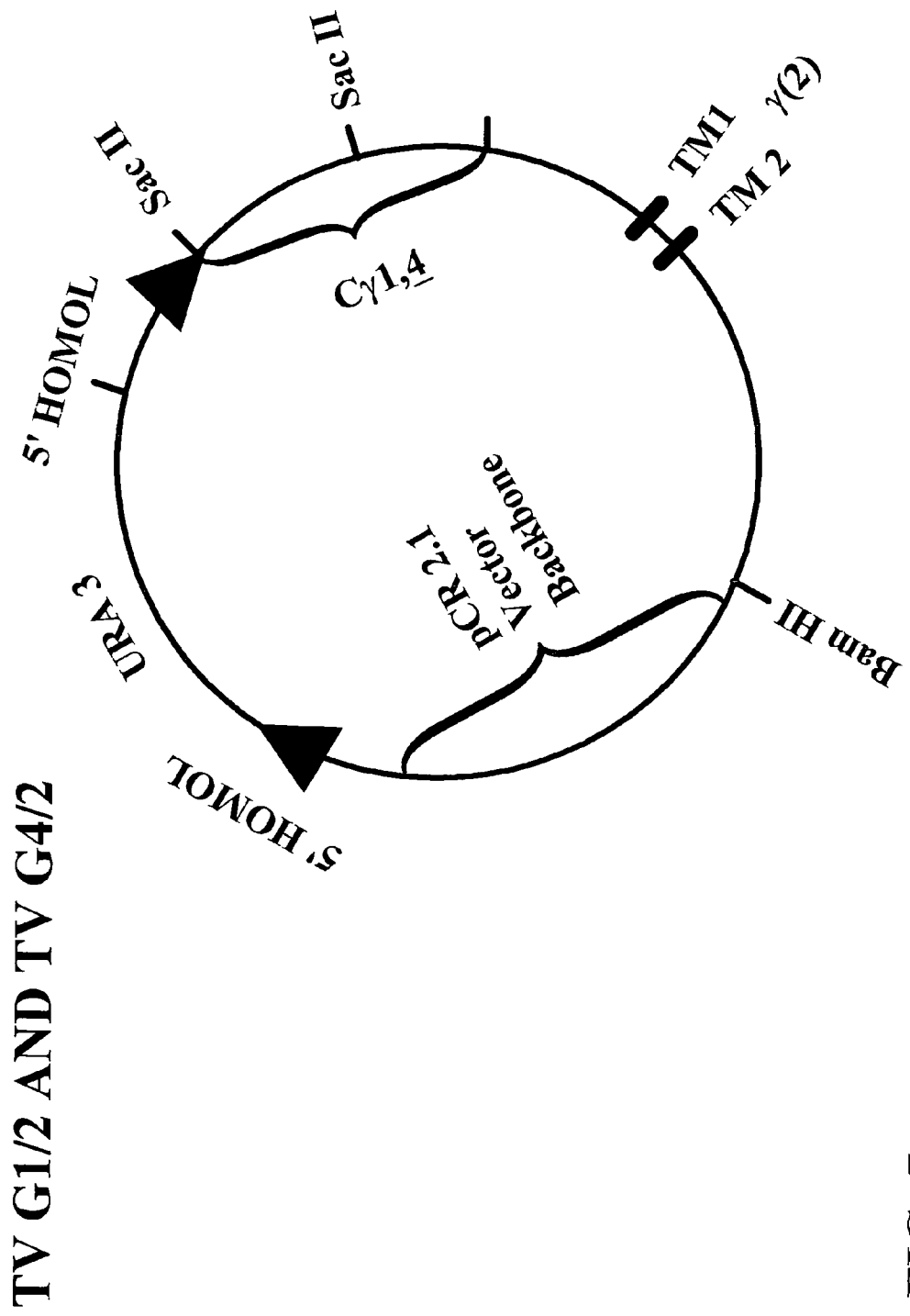
FIG. 7 is a schematic diagram of the targeting vectors (TV G1/2 and TV G4/2) for retrofitting yH1C to yHG1/2 and yHG4/2 YACs.
Figure 8A:
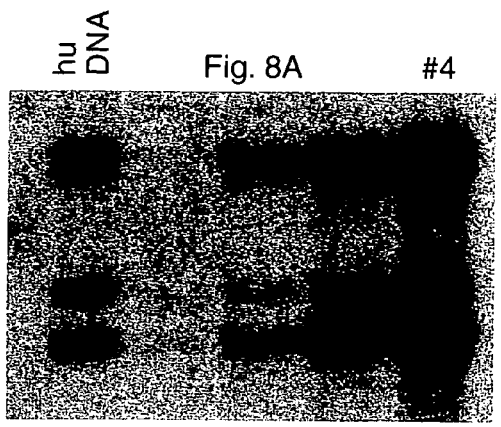
FIG. 8 shows Southern blot analyses of ES clones fused with yH3B YAC (Clone Z 70.17.1)
Figure 8B:
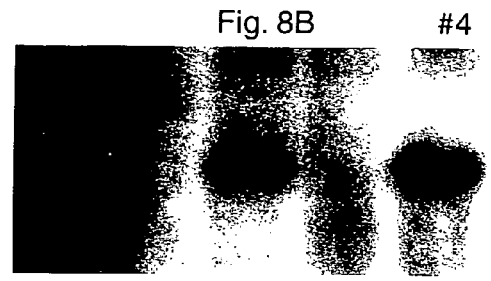
Figure 8C:
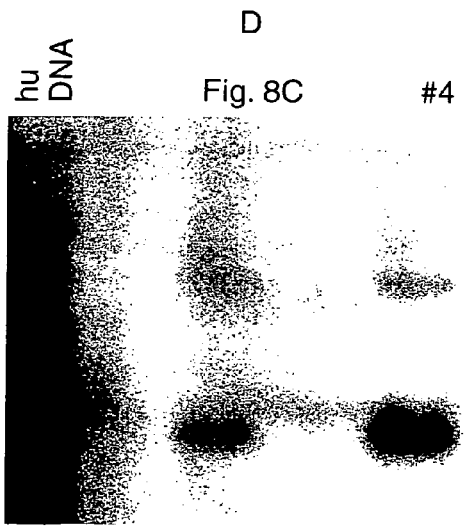
Figure 8E:
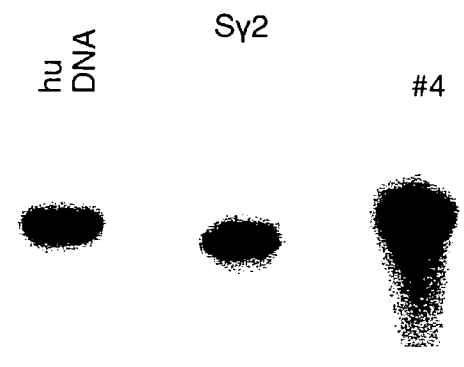
Figure 8D:
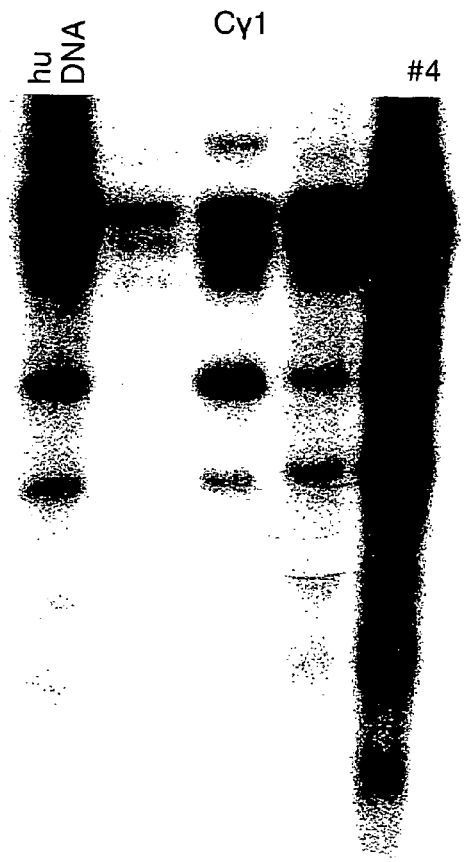

Alternatively, after step 7 we remove the 5' homology and URA3 gene from the plasmid described in step 7 by digesting with XbaI. Then we clone the 5' homology and URA3 gene into the XbaI site of the plasmid described in step 6 to produce the TV G1/2 vector shown in FIG. 7.

Figure 4:
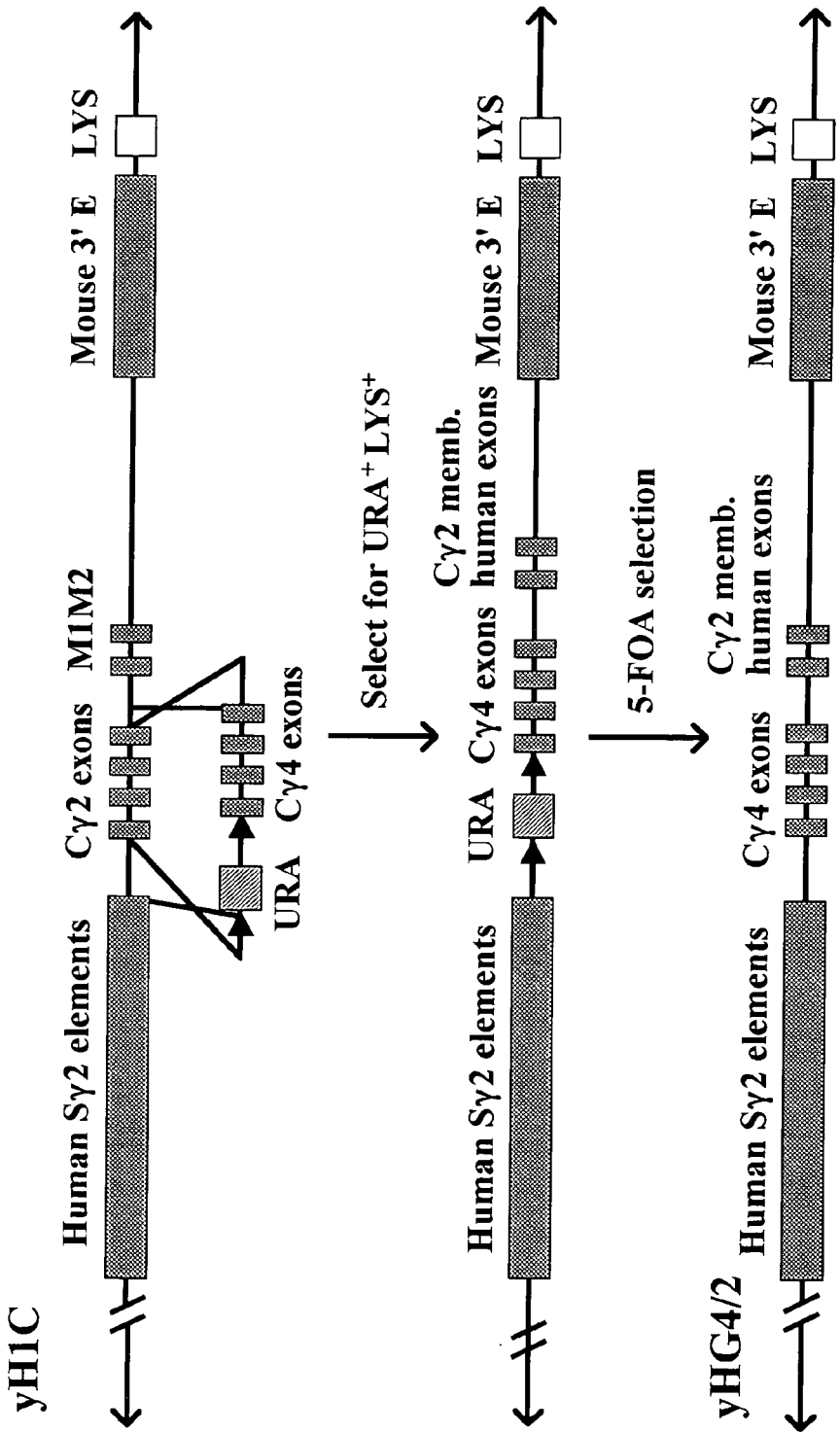
FIG. 4 is a schematic depiction of the yH1C and yHG4/2 yeast artificial chromosomes (YACs).

We construct the TV G4/2 targeting vector, which has a chimeric construct with human γ4 coding exons attached downstream of 5 kb of human switch γ2 region DNA and human γ2 CH coding exons (FIG. 4) utilizing the above-described procedures with some modifications.

The plasmid produced in step 1 is subjected to partial digestion with restriction enzyme XmnI followed by digestion with the restriction enzyme HindIII. The digestion with XmnI occurs 75 bp upstream of the γ2 stop codon. Therefore, the 4th exon of the γ4/γ2 chimeric gene initially contains 75 bp of γ2 in addition to the two 3' γ2 membrane exons. There is a single base pair difference between γ4 and γ2 in this region, which results in a single amino acid change. To correct this, we perform site directed mutagenesis to a C to T at the human gamma 2 gene using a Directed Mutagenesis Kit from Clontech Laboratories Inc. (Palo Alto, Calif.).

The we perform the repair using two synthetic oligonucleotides: one to replace the nucleotide necessary to switch sequence from γ2 to γ4 and an auxiliary oligonucleotide to eliminate a NotI site in the pCR2.1 vector with the cloned chimeric G4/2 7 kb fragment.

For replacing C with T, we use the following oligonucleotide:

CCTCTCCCTGTCTCTGGGTAAATGAGTGCC    (SEQ ID NO: 28)

The T residue in bold is replacing C in original plasmid. The second oligonucleotide (to eliminate NotI site) is:

TATCCATCACACTGGCGACCGCTCGAGCAT    (SEQ ID NO:29)

This oligo contains a Not I site (shown in bold) in which a G has been replace with an A to disrupt the site. We sequence part of the plasmid to confirm that the correct nucleotide was replaced.

EXAMPLE 5

Targeting Strategy

We linearized the above described vectors, TV1, TV4, TV G1, TV G4, TVG ½ and TV G4/2 and used them to transform yeast cell cultures with yH1C YAC by lithium acetate transformation. We subsequently used the linearized vectors to replace the targeted genes on yH1C as described below, to produce the new YACs yH2Bm, yH2Cm, yHG1, yHG4, yHG1/2 and yHG4/2 respectively (FIGS. 1-4). We plated yeast cells on SC-URA media after transformation to select for the integration of the URA3 marker. We checked any resulting clones for YAC integrity using pulse field gel electrophoresis. In addition, we analyzed clones by Southern blot to validate the structure and identity.

In the case of yHG1/2, the URA3 gene in resulting YACs was flanked by 5' homology sequences which we removed as follows.

We plated yeast cultures containing yHG1/2 YAC on agar plates with 5 FOA (negative selection for URA). We checked the resulting 5 FOA-resistant clones for integrity by pulse field gel and Southern blots as outlined above.

We use the TVG1 vector and the TV G4/2 vector to produce the yHG1 and yHG4/2 YACs, respectively, following the above-described strategies.

EXAMPLE 6

Introduction of the yH2BM YAC into ES Cells

We introduced the YAC, yH2BM, into mouse embryonic stem (ES) cells through yeast spheroplast fusion as described in detail below. [See B. Birren et al., *Genome Analysis: A Laboratory Manual*, Volume 3, Cloning Systems, "Chapter 5: Introduction of YACs into mammalian cells by spheroplast fusion", pages 548-550, Cold Spring Harbor Laboratory Press, Plainview, N.Y.]. yH2BM containing yeast cells were spheroplasted using zymolase 20T at 0.15 mg/ml. The yH2BM spheroplasts were fused with HPRT-deficient E 14.TG3B1 mouse ES cells which had been cultured as described below [See Tsuda et al., Genomics 42:413-421 (1997)]. HAT selection was initiated 48 hours after fusion. HPRT-positive ES cell clones were selected at a frequency of 1 clone/15-20×10$^6$ fused cells. Twenty-one HAT resistant colonies were expanded for genome analysis and were analyzed for YAC integrity by Southern and CHEF blot analyses. In control experiments fusing ES cells alone and yeast spheroplasts alone, no colonies were detected.

The detailed procedure is as follows:

Producing Yeast Spheroplasts

Excess yeast cells were prepared because up to 50% will be lost during the spheroplasting procedure. For fusing 5×10$^7$ ES cells, approximately 5×10$^9$ yeast cells are needed.

We inoculated selective medium (SC-) with freezer stock to give a starting inoculum of approximately 5×10$^6$ cells/ml.

We determined the cell density in the culture by use of a hemocytometer. We grew the cells at 23° C. with shaking at 250 rpm overnight. Incubation can also be at 14° C. or 18° C. to increase YAC stability. Culturing at 30° C. may result in deletion of some Ig gene segments in the YAC. In the morning, the culture density was be $2\times10^7$ cells/ml. We stepped down to $1\times10^7$ cells/ml with YPDA (rich) medium, and incubated for 2-3 hours. Culture density at this step should not exceed $2\times10^7$ cells/ml because exponentially growing yeasts are needed for efficient and complete spheroplasting.

We poured the desired amount of culture (to provide $5\times10^9$ cells) into sterile 50 ml tubes, centrifuged at 1000-1200 g (2300-2500 rpm in a Jouan GR4-22 centrifuge) at room temperature for 5-10 minutes, and discarded the supernatant. Alternatively, large volumes of cells can be pelleted in large conical centrifuge tubes.

We added 20 ml of sterile $H_2O$ to each tube of yeast cells, resuspended the cells by vortexing (or with a pipette), centrifuged as above, and discarded the supernatant. Next, we added 20 ml of 1 M sorbitol to each tube of yeast cells, resuspended the cells by vortexing (or with a pipette), centrifuged as above, and discarded the supernatant. We resuspended the cells in SPE buffer (1 M sorbitol, 10 mM sodium phosphate, 10 mM EDTA) containing a 1:500 dilution of freshly added 2-mercaptoethanol to a final cell concentration of $5\times10^8$ cells/ml.

We combined 10 µl of the previous cell suspension with 90 µl of 5% (w/v) SDS and another 10 µl of the cell suspension with 90 µl of 1 M sorbitol. We determined the cell concentration of each mixture with a hemocytometer. Warm the yeast cell suspension from the previous paragraph to 30° C. For each 1 ml of yeast cell suspension, add 1.5 µl of a 100 mg/ml stock of Zymolyase-20T (ICN). We incubated stationary at 30° C. At 5 minute intervals, combine 10 µl of the cell suspension with 90 µl of 5% (w/v) SDS and determine the cell concentration with a hemocytometer. We monitored the decrease in the number of cells that remain in the presence of SDS treatment (compared with the initial cell concentration in the presence of sorbitol).

When 95% of the cells become lysed in SDS, immediately centrifuged the sample at 200-300 g (1000-1200 rpm in a Jouan GR4-22 centrifuge) at room temperature for 5 minutes and poured off the supernatant carefully (the pellet should be very loose and some loss of cells will occur).

The total time for spheroplasting (steps after zymolase is added) is typically 5-20 minutes.

We gently resuspended the spheroplasts in 20 ml of STC buffer (0.98 M sorbitol, 10 mM Tris, 10 mM $CaCl_2$) by inversion or careful pipetting, centrifuged the sample at 200-300 g (1000-1200 rpm in a Jouan GR4-22 centrifuge) at room temperature for 5 minutes, and carefully poured off the supernatant. We repeated this procedure one time. We resuspended the spheroplasts at $2.5\times10^8$ cells/ml in STC and kept them at room temperature (or on ice) until used in step 14.

Fusion with ES Cells

We transferred 1 ml containing $2.5\times10^8$ spheroplasts of the spheroplast suspension to a 15-ml tube and centrifuged 1 ml at 200-300 g (1000-1200 rpm in a Jouan GR4-22 centrifuge) at room temperature for 5 minutes. We removed all of the supernatant by slow aspiration with a drawn-out glass pipette. With the tube in a semihorizontal position, we gently added 1 ml of ES cells (at $5\times10^6$ cells/ml) without disturbing the spheroplast pellet. The spheroplast:ES cell ratio can vary from 25:1 to 50:1.

We prepared the ES cells in advance as follows: we started ES cultures in plates coated with mouse primary feeders, with a starting density of $6\times10^6$ ES cells per 100-mm plate and standard ES medium (DMEM high glucose, 100 units/ml of penicillin, 100 µg/ml of streptomycin, 2 mM L-glutamine, 100 µm 2-mercaptoethanol, 1000 units/ml of murine Leukemia inhibitory Factor [ESGRO™], and 15% heat-inactivated fetal calf serum). Following 48 hours of standard growth conditions, we trypsinized the cultures and used the resulting cells to start cultures on gelatin-coated plates at $10^7$ ES cells per 100-mm plate. We allowed growth to continue for 16-24 hours. Four hours before fusion, we replaced the medium on the ES plates with fresh medium. Immediately before fusion, we trypsinized the cells, washed three times with serum-free ES medium at room temperature, and resuspended in serum-free ES medium at $5\times10^6$ cells/ml.

We centrifuged the combined spheroplast/ES cell sample at 300 g (1200 rpm in a Jouan GR4-22 centrifuge) at room temperature for 3 minutes and carefully aspirated off all medium with a drawn-out glass pipette.

We gently tapped the tube to loosen the cell pellet and used a P1000 tip to slowly add 0.5 ml of 50% (w/v) PEG 1500 (pH 8.0; e.g., Boeringer Mannheim 783641) containing 10 mM $CaCl_2$ (prewarmed to 37° C.) While this solution was being added, we gently mixed the cells with the pipette tip. Once all of the solution was added, we slowly pipetted the cell suspension up and down one time. We incubated the cell suspension at room temperature for 90 seconds. We slowly added 5 ml of serum-free ES medium by pipetting it from the bottom of the tube. We incubated cells at room temperature for 30 minutes and, after 30 minutes, centrifuged the cell suspension at 300 g (1200 rpm in a Jouan GR4-22 centrifuge) at room temperature for 3 minutes and carefully aspirated off all medium with a drawn-out glass pipette.

We resuspended the cells in 10 ml of standard ES medium and plated the entire sample (~$5\times10^6$ ES cells) on a 100-mm mouse primary-feeder-coated plate. If initial attempts result in the generation of too many colonies, the amount of the sample plated on each 100-mm plate may need to be adjusted downward.

We incubated the plates under standard ES cell growth conditions overnight and then replaced the medium with fresh ES medium.

Following 48 hours of culturing (after the spheroplast fusion), we began growth under the appropriate selective conditions (i.e., dictated by the specific mammalian selectable marker present on the YAC). We replaced the medium every 2 days. We picked and plate ES colonies on mouse primary-feeder-coated plates for expansion per standard procedures. We typically observed ES colonies 10-15 days following spheroplast fusion.

Here, seven ES cell clones (referred to as 1 through 7 in Table 3) derived from ES cell fusion with yH2Bm-containing yeast were found to contain all expected EcoRI and BamHI yH2 fragments detected by probes spanning the entire insert. As shown in Table 3, the following human genes were detected in the ES cell genome as part of characterization of the ES cell DNA prior to transgenic mouse generation: all the different $V_H$ families could be detected $V_H1$, $V_H2$, $V_H3$, $V_H4$, $V_H5$, and $V_H6$; human $D_H$, and $J_H$; human $C_\mu$ and $C_\delta$ constant regions; mouse switch γ1 (mSγ1) and human Cγ1 $C_H$ exons.

TABLE 3

| h or 1m genes | ES Cell Clone | | | | | | |
|---|---|---|---|---|---|---|---|
| | 1 | 2 | 3 | 4 | 5 | 6 | 7 |
| $V_H1$ | + | + | + | + | + | + | + |
| $V_H2$ | + | + | + | + | + | + | + |
| $V_H3$ | + | + | + | + | + | + | + |
| $V_H4$ | + | + | + | + | + | + | + |

TABLE 3-continued

| h or ¹m genes | ES Cell Clone | | | | | | |
|---|---|---|---|---|---|---|---|
| | 1 | 2 | 3 | 4 | 5 | 6 | 7 |
| $V_H5$ | + | + | + | + | + | + | + |
| $V_H6$ | + | + | + | + | + | + | + |
| $D_H$ | + | + | + | + | + | + | + |
| $J_H$ | + | + | + | + | + | + | + |
| $C_\mu$ | + | + | + | + | + | + | + |
| $C_\delta$ | + | + | + | + | + | + | + |
| mSγ1 | + | + | + | + | + | + | + |
| Cγ1 | + | + | + | + | + | + | + |

¹m - denotes mouse genes (mSγ1)

EXAMPLE 7

Introduction of ES Cells Containing the yH2BM YAC into Mice

In order to generate chimeric mice from ES cells containing the YAC yH2BM DNA, we microinjected of blastocysts, followed by breeding. We isolated ES cells containing the YAC yH2BM DNA as described in Example 5, and expanded for the generation of chimeric mice. Next, we microinjected yH2BM-bearing ES cell clones into mouse C57Bl/6 blastocysts [See B. Hogan et al., "Manipulating the Mouse Embryo: A Laboratory Manual", Section D, Introduction of New Genetic Information, "*Injection of Cells into the Blastocyst*" pages 188-196, (1986) (Cold Spring Harbor Laboratory Press, Cold Spring Harbor, N.Y.)]. Chimeric offspring were identified by coat color.

TABLE 4

| Clone | # embryos Injected | # live born pups | # of chimeras | # chimera breedings | # germline |
|---|---|---|---|---|---|
| 2BM-1 | 162 | 16 | 15 | 8 | 4 |
| 2BM-2 | 144 | 5 | 5 | 3 | 2 |
| 2BM-3 | 335 | 20 | 15 | 6 | 0 |
| 2BM-4 | 261 | 6 | 4 | 3 | 0 |
| 2BM-5 | 344 | 15 | 15 | 7 | 1 |
| 2BM-6 | 382 | 27 | 27 | 8 | 6 |
| 2BM-7 | 201 | 29 | 27 | 7 | 5 |

Table 4 summarizes the data for generating transgenic mice using seven different yH2BM containing ES cell lines. Five out of seven clones were transmitted through the mouse germline.

EXAMPLE 8

Breeding Mice Containing yH2BM YAC DNA with yK2:DI Mice

In order to generate mice that produce human antibodies in the absence of endogenous antibodies, we bred yK2-transgenic mice with double-inactivated (DI) mouse strains. The DI mouse strains are homozygous for gene targeted-inactivated mouse heavy and kappa light chain loci and, thus, lack in antibody production [see Jakobovits et al., *Nature* 362:255-258 (1993); Green et al., *Nature Genetics* 7:13-21 (1994)]. We bred one of the yK2-transgenic mouse strains, J23.1, with DI mice to generate mice hemizygous or homozygous for yK2 YACs on a homozygous inactivated mouse heavy and kappa chain background (yK2;DI). The breeding scheme for generating a new XenoMouse, which is hemizygous for the yH2BM YAC is shown below. Subsequent breeding of XenoMouse males to XenoMouse females yields XenoMouse progeny who are either hemizygous or homozygous for yH2BM and/or yK2. From these progeny, breeding of males and females, both of which are homozygous for both yH2BM and yK2, will yield a true breeding line of XenoMouse yH2BM.

XenoMouse H2BM Breeding scheme

Generation 1: (Chimera or Transgenic bred to YK2: DI)

yH2BM$^+$; yK2$^-$; mJ$_H^{+/+}$; mCκ$^{+/+}$ × yH2BM$^-$; yK2$^+$; mJ$_H^{-/-}$; mCκ$^{-/-}$
Generation 2: (Xenohet × YK2: DI)

yH2BM$^+$; yK2$^+$; mJ$_H^{+/-}$; mCκ$^{+/-}$ × yH2BM$^-$; yK2$^+$; mJ$_H^{-/-}$; mCκ$^{-/-}$
Generation 3 (Almost Xenomouse × yK2: DI)
or Xenomouse × yK2; DI)

yH2BM+; yK2$^+$; mJ$_H^{+/-}$; mCκ$^{-/-}$ × yH2BM$^-$; yK2$^+$; mJ$_H^{-/-}$; mCκ$^{-/-}$
yH2BM+; yK2$^+$; mJ$_H^{-/-}$; mCκ$^{-/-}$ × yH2BM$^-$; yK2$^+$; mJ$_H^{-/-}$; mCκ$^{-/-}$

XenoMouse: yH2BM$^+$; yK2$^+$; mJ$_H^{-/-}$; mCκ$^{-/-}$

We confirmed the integrity of the human heavy and kappa chain YACs in XenoMouse H2BM strains by Southern blot analysis. In all XenoMouse H2BM strains analyzed, yH2BM was transmitted unaltered through multiple generations with no apparent deletions or rearrangements.

EXAMPLE 9

Flow Cytometry Analysis

To further characterize Xenomouse H2BM transgenic mice, peripheral blood and spleen lymphocytes were isolated from 8-10 week old mice and controls. The cells were purified on Lympholyte M (Accurate) (San Diego, Calif.) and treated with purified anti-mouse CD32/CD16 Fc receptor (Pharmingen, 01241D) (San Diego, Calif.) to block non-specific binding to Fc receptors. Next, the cells were stained with various antibodies and analyzed on a FACStar$^{PLUS}$ (Becton Dickinson, CELLQuest software). The panel of antibodies used to stain XenoMouse H2BM cells included: Cychrome (Cyc) anti-B220 (Pharmingen, 01128A); fluoroscein isothiocyanate (FITC) anti-human IgM (Pharmingen, 34154X); FITC anti-mouse IgM (Pharmingen, 02204D).

Lymphocytes from four animals from three different XenoMouse H2BM strains were evaluated and compared to wild type B6/129 mice using flow cytometry, as shown in Table 5 below.

Strains XM-2BM-1, XM-2BM-2 and XM-2BM-6 showed about a 60-80% reconstitution in the B-cell compartment compared to wild-type mice (Table 5). Trangenic mice having the yH2BM YAC DNA show significant human antibody and immune system development.

TABLE 5

| strain | % of B220$^+$ IgM$^+$ | AVG. % B CELLs |
|---|---|---|
| XM-2BM-1 #1 | 34 | 24 |
| XM-2BM-1 #2 | 24 | |
| XM-2BM-1 #3 | 19 | |
| XM-2BM-1 #4 | 17 | |
| XM-2BM-2 #1 | 28 | 28 |
| XM-2BM-2 #2 | 27 | |

TABLE 5-continued

| strain | % of B220+ IgM+ | AVG. % B CELLs |
|---|---|---|
| XM-2BM-2 #3 | 29 | |
| XM-2BM-2 #4 | 27 | |
| XM-2BM-6 #1 | 27 | 25 |
| XM-2BM-6 #2 | 28 | |
| XM-2BM-6 #3 | 22 | |
| XM-2BM-6 #4 | 23 | |
| WT B6X129 #1 | 40 | 39 |
| WT B6X129 #2 | 38 | |
| WT B6X129 #3 | 35 | |
| WT B6X129 #4 | 43 | |

EXAMPLE 10

Serum Levels of Human Antibodies in Unimmunized Mice

An ELISA for determination of human antibodies in unimmunized mouse serum was carried out. For more detailed information and procedures on immunoassays see E. Harlow et al., *Antibodies: A Laboratory Manual*, Chapter 14, *"Immunoassay"*, pages 553-614, Cold Spring Harbor Laboratory Press, Cold Spring Harbor, N.Y. (1988). The concentration of human immunoglobulins were determined using the following capture antibodies: mouse anti-human IgM (CGI/ATCC, HB-57) (Manassas, Va.). The detection antibodies used in ELISA experiments were mouse anti-human IgG1-HRP (Southern Biotechnology, 9050-05) (Birmingham, Ala.), mouse anti-human IGM-HRP (Southern Biotechnology, 9020-05) (Birmingham, Ala.). Standards used for quantitation of human Ig were: human IgMκ (Cappel, 13000) (Costa Mesa, Calif.) and human IgG1 (Calbiochem 400126) (San Diego, Calif.).

As shown in Table 6, XenoMouse H2BM mice produced significant baseline levels of both human IgM and human IgG in the absence of immunization.

TABLE 6

Quantitation of hIgγ1 and hIgM in XenoMouse H2BM

| | | Igγ1 µg/ml | IgM µg/ml |
|---|---|---|---|
| XM-2BM-7 | H-781-2 | 298 | 140 |
| | H-850-1 | 172 | 101 |
| | H-850-2 | 250 | 110 |
| XM-2BM-1 | H-908-1 | 1.3 | 70 |
| | H-908-5 | 0.35 | 51 |
| | H-953-8 | 3.7 | 81 |
| XM-2BM-2 | H-873-2 | 0.8 | 38 |
| | H-873-3 | 1.5 | 52 |
| | H-873-4 | 1.7 | 90 |
| XM-2BM-6 | H-910-4 | 1 | 68 |
| | H-911-3 | 0.8 | 47 |
| | H-912-4 | 0.3 | 44 |

EXAMPLE 11

Immunization and Hybridoma Generation

Groups of six 8 to 10 weeks old XenoMice H2BM were immunized subcutaneously at the base of the tail (or other route of administration (IP, footpad, etc.) with 10 µg of either recombinant human IL-8, 5 µg TNF-α or CEM cells (for CD147). The antigen is emulsified in complete Freund's adjuvant for the primary immunization and in incomplete Freund's adjuvant for the additional immunizations. For more detailed information and procedures on animal immunizations see E. Harlow et al., *Antibodies: A Laboratory Manual*, Chapter 5, *"Immunizations"* pages 53-138, Cold Spring Harbor Laboratory Press, Cold Spring Harbor, N.Y. (1988). Immunizations are carried out at 3-4 week intervals for at least 3 booster immunizations (boosts).

When making monoclonal antibodies, the mice receive a final injection of antigen or cells in PBS four days before the fusion. For more detailed information and procedures on making monoclonal antibodies see E. Harlow et al., *Antibodies: A Laboratory Manual*, Chapter 6, *"Monoclonal Antibodies"*, pages 139-244, Cold Spring Harbor Laboratory Press, Cold Spring Harbor, N.Y. (1988). Lymph node lymphocytes from immunized mice are fused with the non-secretory myeloma NSO cell line [S. Ray, et al., *Proc. Natl. Acad. Sci. USA*, 91:5548-5551 (1994)] or the P3-X63-Ag8.653 myeloma and are subjected to HAT selection as previously described [G. Galfre, et al., *Methods Enzymol.* 73:3-46 (1981)].

Table 7 shows that transgenic mice produced according to Examples 6-8 above, and immunized with recombinant human IL-8, 5 µg TNF-α or CEM cells (for CD147) yielded human IgG1 monoclonal antibodies.

EXAMPLE 12

Evaluation of Antibody Specifity and Isotype

We performed an ELISA for the determination of whether transgenic mice were producing antigen-specific antibodies (Table 7). We determined the antigen specificity and isotype of antibodies isolated from mouse serum and from hybridoma supernatants as described [Coligan et al., Unit 2.1, "Enzyme-linked immunosorbent assays," in *Current Protocols in Immunology* (1994).], using recombinant human IL-8, CD147 and TNF-α to capture the antigen-specific antibodies. We determined the concentration of human immunoglobulins using the following capture antibodies: rabbit anti-human IgG (Southern Biotechnology, 6145-01). The detection antibodies used in ELISA experiments were mouse anti-human IgG1-HRP (Caltag, MH1015) (Burlingame, Calif.), mouse anti-human IGM-HRP (Southern Biotechnology, 9020-05), and goat anti-human kappa-biotin (Vector, BA-3060). Standards used for quantitation of human and mouse Ig are: human $IgG_1$ (Calbiochem, 400122), human IgMκ (Cappel, 13000), human $IgG_2$κ (Calbiochem, 400122), mouse IgGκ (Cappel 55939), mouse IgMκ (Sigma, M-3795), and mouse $IgG_4$λ (Sigma, M-9019).

Table 7 further shows that transgenic mice produced according to Examples 6-8 above, and immunized with recombinant human IL-8, 5 µg TNF-α or CEM cells (for CD147) yielded human IgG1 monoclonal antibodies that were antigen specific and of the predicted isotype.

TABLE 7

| Fusion | # animals | XM mice yH2BM mice = G1 | # cells × 10⁶ | # Hybridomas | | | |
|---|---|---|---|---|---|---|---|
| | | | | IgG2 | IgG4 | IgG1 | IgM |
| IL-8 | | | | | | | |
| (CEM21)CD147 | 10 | G1-1 | 325 | | | 1 | 1 |
| (CEM22)CD147 | 14 | G1-1 | 198 | | | | 15 |
| IL8-16 | 10 | G1-5 | 243 | | | 20 | 5 |
| IL8-17 | 12 | G1-6 | 268 | | | 31 | 5 |
| IL8-18 | 10 | G1-1 | 213 | | | 10 | |
| IL8-19 | 10 | G1-2 | 136 | | | 4 | |
| TNF-a | | | | | | | |
| TNF-38 | 10 | G1-1/2 | 179 ing. | | | 1 | 3 |
| | | | 116 popl. | | | 2 | 6 |
| TNF-39 | 10 | G1-6 | 180 | | | 4 | 6 |

EXAMPLE 13

Introduction of the yH2CM YAC into ES Cells

We introduced the YAC, yH2CM, into mouse embryonic stem (ES) cells by yeast spheroplast fusion as described in detail in Example 6. [See B. Birren et al., *Genome Analysis: A Laboratory Manual*, Volume 3, Cloning Systems, Chapter 5: "Introduction of YACs into mammalian cells by spheroplast fusion", pages 548-550, Cold Spring Harbor Laboratory Press, Plainview, N.Y.]. Generally, yH2CM containing yeast cells were spheroplasted using zymolase 20T at 1.5 mg/ml. The yH2CM spheroplasts were fused with HPRT-deficient E 14.TG3B1 mouse ES cells which had been cultured as described [see Jakobovits et al., *Nature* 362:255-258 (1993); Green et al., *Nature Genetics* 7:13-21 (1994); E. Robertson in Teratocarcinomas and Embryonic Stem Cells, pages 71-112, IRL, Oxford (1987)] HAT selection was initiated 48 hours after fusion. HPRT-positive ES cell clones were selected at a frequency of 1 clone/15-20×10⁶ fused cells. HAT resistant colonies were expanded for genome analysis and were analyzed for YAC integrity by Southern and CHEF blot analyses. In control experiments with mock fusions of ES cells and yeast spheroplasts, no colonies were detected.

Ten ES cell clones (referred to as Clones 1-10 in Table 8) derived from ES cell fusion with yH2CM-containing yeast contained all expected EcoRI and BamHI yH2 fragments detected by probes spanning the entire insert. As shown in Table 8, we detected the following human genes in the ES cell genome as part of characterization of the ES cell DNA prior to transgenic mouse generation: all the different $V_H$ families could be detected $V_H1$, $V_H2$, $V_H3$, $V_H4$, $V_H5$, and $V_H6$; human $D_H$ and $J_H$; human $C_\mu$ and $C_\delta$ constant regions; mouse switch γ1 (mSγ1) and human Cγ4 $C_H$ exons.

TABLE 8

| h or ¹m genes | ES Cell Clone | | | | | | | | | |
|---|---|---|---|---|---|---|---|---|---|---|
| | 1 | 2 | 3 | 4 | 5 | 6 | 7 | 8 | 9 | 10 |
| $V_H1$ | + | + | + | + | + | + | + | + | + | + |
| $V_H2$ | + | + | + | + | + | + | + | + | + | + |
| $V_H3$ | + | + | + | + | + | + | + | + | + | + |
| $V_H4$ | + | + | + | + | + | + | + | + | + | + |
| $V_H5$ | + | + | + | + | + | + | + | + | + | + |
| $V_H6$ | + | + | + | + | + | + | + | + | + | + |

TABLE 8-continued

| h or ¹m genes | ES Cell Clone | | | | | | | | | |
|---|---|---|---|---|---|---|---|---|---|---|
| | 1 | 2 | 3 | 4 | 5 | 6 | 7 | 8 | 9 | 10 |
| $D_H$ | + | + | + | + | + | + | + | + | + | + |
| $J_H$ | + | + | + | + | + | + | + | + | + | + |
| $C_\mu$ | + | + | + | + | + | + | + | + | + | + |
| $C_\delta$ | + | + | + | + | + | + | + | + | + | + |
| mSγ1 | + | + | + | + | + | + | + | + | + | + |
| Cγ4 | + | + | + | + | + | + | + | + | + | + |

¹m - denotes mouse genes (mSγ1)

EXAMPLE 14

Introduction of ES Cells Containing the yH2CM YAC into Mice

In order to generate chimeric mice from the YAC yH2CM DNA containing ES cells, microinjection of blastocysts was conducted, followed by breeding. ES cells containing the YAC yH2CM DNA were isolated as described in Example 6, and expanded for the generation of chimeric mice. Next, yH2CM-bearing ES cell clones were microinjected into mouse C57B1/6 blastocysts [See B. Hogan et al., "Manipulating the Mouse Embryo: A Laboratory Manual", Section D, Introduction of New Genetic Information, *"Injection of Cells into the Blastocyst"* pages 188-196, (1986) (Cold Spring Harbor Laboratory Press, Cold Spring Harbor, N.Y.)]. Chimeric offspring were identified by coat color.

TABLE 9

| Clone | # embryos Injected | # live born pups | # of chimeras | # chimera breedings | # germline |
|---|---|---|---|---|---|
| 2CM-1 | 381 | 26 | 24 | 8 | 4 |
| 2CM-2 | 399 | 26 | 14 | 10 | 5 |
| 2CM-3 | 224 | 21 | 10 | 5 | 0 |
| 2CM-4 | 217 | 21 | 14 | 4 | 0 |
| 2CM-5 | 276 | 19 | 15 | 9 | 0 |
| 2CM-6 | 296 | 18 | 12 | 2 | 0 |
| 2CM-7 | 269 | 22 | 16 | 6 | 0 |
| 2CM-8 | 133 | 12 | 12 | 9 | 0 |
| 2CM-9 | 177 | 5 | 3 | 1 | 0 |

Table 9 summarized the data for generating transgenic mice using nine different yH2CM containing ES cell lines. Two out of nine clones were transmitted through the mouse germline.

EXAMPLE 15

Breeding Mice Containing yH2CM YAC DNA with yK2:DI Mice

In order to generate mice that produced human antibodies in the absence of endogenous antibodies, yK2-transgenic mice were previously bred with double-inactivated (DI) mouse strains. The DI mouse strains were homozygous for gene targeted-inactivated mouse heavy and kappa chain loci and thus were deficient in antibody production [see Jakobovits et al., *Nature* 362:255-258 (1993); Green et al., *Nature Genetics* 7:13-21 (1994)]. One of the yK2-transgenic mouse strains, J23.1, was bred with DI mice to generate mice hemizygous or homozygous for yK2 YACs on a homozygous inactivated mouse heavy and kappa chain background (yK2; DI). The breeding scheme for generating a new Xenomouse, which is hemizygous for the yH2CM YAC is shown below. Subsequent breeding of XenoMouse males to XenoMouse females yields XenoMouse progeny who are either hemizygous or homozygous for yH2CM and/or yK2. From these progeny, breeding of males and females, both of which are homozygous for both yH2CM and yK2, will yield a true breeding line of XenoMouse H2CM.

| XenoMouse H2CM Breeding scheme |
| --- |
| Generation 1: (Chimera or Transgenic bred to YK2: DI) |
| yH2CM$^+$; yK2$^-$; mJ$_H^{+/+}$; mCκ$^{+/+}$ × yH2CM$^-$; yK2$^+$; mJ$_H^{-/-}$; mCκ$^{-/-}$ |
| Generation 2: (Xenohet × YK2: DI) |
| yH2CM$^+$; yK2$^+$; mJ$_H^{+/-}$; mCκ$^{+/-}$ × yH2CM$^-$; yK2$^+$; mJ$_H^{-/-}$; mCκ$^{-/-}$ |
| Generation 3 (Almost Xenomouse × yK2: DI) or Xenomouse × yK2; DI) |
| yH2CM+; yK2$^+$; mJ$_H^{+/-}$; mCκ$^{-/-}$ × yH2CM$^-$; yK2$^+$; mJ$_H^{-/-}$; mCκ$^{-/-}$ |
| yH2CM+; yK2$^+$; mJ$_H^{-/-}$; mCκ$^{-/-}$ × yH2CM$^-$; yK2$^+$; mJ$_H^{-/-}$; mCκ$^{-/-}$ |
| XenoMouse: yH2CM$^+$; yK2$^+$; mJ$_H^{-/-}$; mCκ$^{-/-}$ |

The integrity of the human heavy and kappa chain YACs in XenoMouse H2CM strains was confirmed by Southern blot analysis. In all XenoMouse H2CM strains analyzed, yH2CM was transmitted unaltered through multiple generations with no apparent deletions or rearrangements.

EXAMPLE 16

Flow Cytometry Analysis

To further characterize Xenomouse H2CM transgenic mice, peripheral blood and spleen lymphocytes were isolated from 8-10 week old mice and controls. The cells were purified on Lympholyte M (Accurate) (San Diego, Calif.) and treated with purified anti-mouse CD32/CD16 Fc receptor (Pharmingen, 01241D) (San Diego, Calif.) to block non-specific binding to Fc receptors. Next, the cells were stained with various antibodies and analyzed on a FACStar$^{PLUS}$ (Becton Dickinson, CELLQuest software). The panel of antibodies used to stain XenoMouse H2CM cells included: Cychrome (Cyc) anti-B220 (Pharmingen, 01128A); fluoroscein isothiocyanate (FITC) anti-human IgM (Pharmingen, 34154X); FITC anti-mouse IgM (Pharmingen, 02204D).

Lymphocytes from two animals from two different XenoMouse H2CM strains were evaluated and compared to wild type B6/129 mice using flow cytometry as shown in Table 10 below.

Strain XM2Cm-2 homo showed about a 80-100% reconstitution in the B-cell compartment (Table 10). Trangenic mice having the yH2CM YAC DNA show significant human antibody and immune system development. Control 129xB6, DI, Xenomouse 2a heterozygous and homozygous were compared to mice heterozygous and homozygous for the yH2CM YAC.

TABLE 10

| ID | % B220$^+$μ$^+$ |
| --- | --- |
| 129 × B6 | 22.2 |
| 129 × B6 | 24.8 |
| 129 × B6 | 24.5 |
| DI | 0.6 |
| XM2A-5 het | 29.2 |
| XM2A-5 het | 23.7 |
| XM2A-5 homo | 23.4 |
| XM2A-5 homo | 25.5 |
| XM2Cm-2 het | 19.3 |
| XM2Cm-2 het | 19.2 |
| XM2Cm-2 homo | 29.8 |
| XM2Cm-2 homo | 23.6 |
| Avg. 129 × B6 | 23.8 ± 1.4 |
| DI | 0.6 |
| Avg. XM2A-5 het | 26.5 ± 3.9 |
| Avg. XM2A-5 homo | 24.5 ± 1.5 |
| Avg. XM2Cm-2 het | 19.3 ± 0.1 |
| Avg. XM2Cm-2 homo | 26.7 ± 4.4 |

EXAMPLE 17

Serum Levels of Human Antibodies in Unimmunized Mice

An ELISA for determination of human antibodies in unimmunized mouse serum was carried out. For more detailed information and procedures on immunoassays see E. Harlow et al., *Antibodies: A Laboratory Manual*, Chapter 14, *"Immunoassay"*, pages 553-614, Cold Spring Harbor Laboratory Press, Cold Spring Harbor, N.Y. (1988). The concentration of human immunoglobulins were determined using the following capture antibodies: mouse anti-human IgM (CGI/ATCC, HB-57) (Manassas, Va.). The detection antibodies used in ELISA experiments were mouse anti-human IgG$_4$-HRP (Southern Biotechnology, 9050-05) (Birmingham, Ala.), mouse anti-human IGM-HRP (Southern Biotechnology, 9020-05) (Birmingham, Ala.). Standards used for quantitation of human Ig were: human IgMκ (Cappel, 13000) (Costa Mesa, Calif.) and human IgG1 (Calbiochem 400126) (San Diego, Calif.).

As shown in Table 11, rows 15-30, Xenomouse H2CM produced significant baseline levels of both human IgM and IgG4 in the absence of immunization.

TABLE 11

| | hIgM (μg/ml) | hIgG2 (μg/ml) | hIgG4 (μg/ml) |
| --- | --- | --- | --- |
| Mouse ID | | | |
| 1 129 × B6 | | | |
| 2 129 × B6 | | | |
| 3 129 × B6 | | | |
| 4 DI | | | |

TABLE 11-continued

| | hIgM (µg/ml) | hIgG2 (µg/ml) | hIgG4 (µg/ml) |
|---|---|---|---|
| 5 DI | | | |
| 6 DI | | | |
| 7 XM2A-5 | 89.5 | 37.6 | |
| 8 XM2A-5 | 97.1 | 37.6 | |
| 9 XM2A-5 | 98 | 409.7 | |
| 10 XM2A-5 | 85.1 | 18.2 | |
| 11 XM2A-5 | 72 | 423.1 | |
| 12 XM2A-5 | 74.3 | 273.3 | |
| 13 XM2A-5 | 98.6 | 16.8 | |
| 14 XM2A-5 | 126.8 | 28.8 | |
| Xenomouse H2CM | | | |
| 15 XM2Cm-1 | 109.4 | | 33.2 |
| 16 XM2Cm-1 | 83.6 | | 187.1 |
| 17 XM2Cm-1 | 84.9 | | 665.3 |
| 18 XM2Cm-1 | 88.7 | | 61.3 |
| 19 XM2Cm-1 | 93.1 | | 177.2 |
| 20 XM2Cm-1 | 79.4 | | 36.9 |
| 21 XM2Cm-1 | 80.4 | | 91.2 |
| 22 XM2Cm-1 | 76.9 | | 238.6 |
| 23 XM2Cm-2 | 35.2 | | 20.9 |
| 24 XM2Cm-2 | 35.4 | | 88.8 |
| 25 XM2Cm-2 | 28 | | 42.5 |
| 26 XM2Cm-2 | 25 | | 20.6 |
| 27 XM2Cm-2 | 66.8 | | 23 |
| 28 XM2Cm-2 | 28.1 | | 14.8 |
| 29 XM2Cm-2 | 27.3 | | 30.1 |
| 30 XM2Cm-2 | 32.6 | | 69.3 |
| 129 × B6 | N.D. | N.D. | N.D. |
| DI | N.D. | N.D. | N.D. |
| XM2A-5 | 92.7 ± 17.2 | 155.6 ± 182.1 | N.D. |
| XM2Cm-1 | 87.1 ± 10.4 | N.D. | 186.4 ± 208.0 |
| XM2Cm-2 | 34.8 ± 13.5 | N.D. | 38.8 ± 26.7 |

EXAMPLE 18

Immunization and Hybridoma Generation

Groups of six 8 to 10 weeks old XenoMice H2CM were immunized subcutaneously at the base of the tail with 10 µg of either recombinant human IL-6 or IL-8. The antigen is emulsified in complete Freund's adjuvant for the primary immunization and in incomplete Freund's adjuvant for the additional immunizations. For more detailed information and procedures on animal immunizations see E. Harlow et al., *Antibodies: A Laboratory Manual*, Chapter 5, *"Immunizations"* pages 53-138, Cold Spring Harbor Laboratory Press, Cold Spring Harbor, N.Y. (1988). Immunizations are carried out at 3-4 week intervals for at least 3 booster immunizations (boosts).

When making monoclonal antibodies, the mice receive a final injection of antigen or cells in PBS four days before the fusion. For more detailed information and procedures on making monoclonal antibodies see E. Harlow et al., *Antibodies: A Laboratory Manual*, Chapter 6, *"Monoclonal Antibodies"*, pages 139-244, Cold Spring Harbor Laboratory Press, Cold Spring Harbor, N.Y. (1988). Lymph node lymphocytes from immunized mice fused with the non-secretory myeloma NSO cell line [S. Ray, et al., *Proc. Natl. Acad. Sci. USA*, 91:5548-5551 (1994)] or P3-X63-Ag8.653 myeloma cells and subjected to HAT selection as previously described [G. Galfre, et al., *Methods Enzymol*. 73:3-46 (1981)].

Table 12 shows that transgenic mice produced according to Examples 14-16 above, and immunized with recombinant human IL-6 or IL-8, yielded human IgG4 monoclonal antibodies.

EXAMPLE 19

Evaluation of Antibody Specifity and Isotype

We performed an ELISA to determine whether transgenic mice were producing antigen-specific antibodies (Table 12). We also determined the human antibody isotype produced (Table 12). Antigen specificity and isotype determinations were performed on antibodies isolated from mouse serum and from hybridoma supernatants as described [Coligan et al., Unit 2.1, "Enzyme-linked immunosorbent assays," in *Current protocols in immunology* (1994).] using recombinant human IL-6 or IL-8, to capture the antigen-specific antibodies. The concentration of human and mouse immunoglobulins were determined using the following capture antibodies: rabbit anti-human IgG (Southern Biotechnology, 6145-01). The detection antibodies used in ELISA experiments was mouse anti-human IgG1-HRP (Caltag, MH1015) (Burlingame, Calif.), mouse anti-human IGM-HRP (Southern Biotechnology, 9020-05), and goat anti-human kappa-biotin (Vector, BA-3060). Standards used for quantitation of human and mouse Ig were: human $IgG_1$ (Calbiochem, 400122), human IgMκ (Cappel, 13000), human $IgG_2$κ (Calbiochem, 400122), mouse IgGκ (Cappel 55939), mouse IgMκ (Sigma, M-3795), and mouse $IgG_4$λ (Sigma, M-9019).

Table 12 further shows that transgenic mice produced according to Examples 14-16 above, and immunized with recombinant human IL-6 or IL-8 yielded human IgG4 monoclonal antibodies that were antigen specific and of the predicted isotype.

TABLE 12

| Fusion | # animals | XM mice yH2CM mice = G4 | # cells × 106 | # Hybridomas | | | |
|---|---|---|---|---|---|---|---|
| | | | | IgG2 | IgG4 | IgG1 | IgM |
| IL-6 | | | | | | | |
| IL6-1 | 12 | G4-2 | 132 | | 13 | | |
| IL-8 | | | | | | | |
| IL8-13 | 10 | G4 1-2 | 66 | | 27 | | |
| IL8-14 | 10 | G4 1-2 | 41 | | 7 | | |
| IL8-15 | | G4 1-2 | 41 | | 14 | | |

EXAMPLE 20

Introduction of the yHG1/2 YAC into ES Cells

We introduced the YAC, yHG1/2, into mouse embryonic stem (ES) cells by yeast spheroplast fusion as described in Example 6. [See B. Birren et al., *Genome Analysis: A Laboratory Manual*, Volume 3, Cloning Systems, Chapter 5: "Introduction of YACs into mammalian cells by spheroplast fusion", pages 548-550, Cold Spring Harbor Laboratory Press, Plainview, N.Y.]. Generally, yHG1/2 containing yeast cells were spheroplasted using zymolase 20T at 0.15 mg/ml. The yHG1/2 spheroplasts were fused with HPRT-deficient E 14.TG3B1 mouse ES cells which were cultured as described [see Jakobovits et al., *Nature* 362:255-258 (1993); Green et al., *Nature Genetics* 7:13-21 (1994); E. Robertson in Teratocarcinomas and Embryonic Stem Cells, pages 71-112, IRL, Oxford (1987)] HAT selection was initiated 48 hours after fusion. HPRT-positive ES cell clones were selected. HAT resistant colonies are expanded for genome analysis and were analyzed for YAC integrity by Southern and CHEF blot analyses. Control experiments were "mock" fusions of ES cells alone and yeast spheroplasts alone.

We examined four ES cell clones derived from ES cell fusion with yHG1/2-containing yeast using Southern blot with probes spanning the entire insert to determine whether the clones contain all expected EcoRI, HindIII and BamHI yH2 fragments. We found that all four ES cell clones contained intact YACs. We detected the following human genes in the ES cell genome as part of characterization of the ES cell DNA prior to transgenic mouse generation: all the different $V_H$ families ($V_H1$, $V_H2$, $V_H3$, $V_H4$, $V_H5$, and $V_H6$); human $D_H$, and $J_H$; human $C_\mu$ and $C_\delta$ constant regions; human switch γ2 (hSγ2) and human Cγ1 $C_H$ exons (see FIG. 8 and Table 13).

TABLE 13

| ES CLONE | D | μ | Cγ | Cd | Sg | 3'e | J | V2 | V3 | V4 | V5 | V6 |
|---|---|---|---|---|---|---|---|---|---|---|---|---|
| # 1 Z 72.12.1 | + | + | + | + | + | + | + | + | + | + | + | + |
| # 2 Z 72.7.1 | + | + | + | + | + | + | + | + | + | + | + | + |
| # 3 Z 72.8.1 | + | + | + | + | + | + | + | + | + | + | + | + |
| # 4 Z 70.17.1 | + | + | + | + | + | + | + | + | + | + | + | + |

Southern Blot Analysis of ES Clones after Fusion with yH3B YAC

EXAMPLE 21

Introduction of ES Cells Containing the yHG1/2 YAC into Mice

To generate chimeric mice from ES cells containing YAC yHG1/2 DNA we used blastocyst microinjection followed by breeding. We isolated ES cells containing the YAC yHG1/2 DNA as described in Example 6, and expanded for the generation of chimeric mice. Next, we microinjected yHG1/2-bearing ES cell clones into mouse C57Bl/6 blastocysts [See B. Hogan et al., *Manipulating the Mouse Embryo: A Laboratory Manual*, Section D, Introduction of New Genetic Information, "Injection of Cells into the Blastocyst" pages 188-196, (1986) (Cold Spring Harbor Laboratory Press, Cold Spring Harbor, N.Y.)].

EXAMPLE 22

Breeding Mice Containing yHG1/2 YAC DNA with yK2:DI Mice

In order to generate mice that produce human antibodies in the absence of endogenous antibodies, yK2-transgenic mice are previously bred with double-inactivated (DI) mouse strains. The DI mouse strains are homozygous for gene targeted-inactivated mouse heavy and kappa chain loci and thus are deficient in antibody production [see Jakobovits et al., *Nature* 362:255-258 (1993); Green et al., *Nature Genetics* 7:13-21 (1994)]. One of the yK2-transgenic mouse strains, J23.1, is bred with DI mice to generate mice hemizygous or homozygous for yK2 YACs on a homozygous inactivated mouse heavy and kappa chain background (yK2;DI). The breeding scheme for generating a new Xenomouse, which is hemizygous for the yHG1/2 YAC is shown below. Subsequent breeding of XenoMouse males to XenoMouse females yields XenoMouse progeny who are either hemizygous or homozygous for yHG1/2 and/or yK2. From these progeny, breeding of males and females, both of which are homozygous for both yHG1/2 and yK2, will yield a true breeding line of XenoMouse HG1/2.

XenoMouse yHG1/2 Breeding scheme

Generation 1: (Chimera or Transgenic bred to YK2: DI)

yHG1/2$^+$; yK2$^-$; mJ$_H^{+/+}$; mCκ$^{+/+}$ × yHG1/2$^-$; yK2$^+$; mJ$_H^{-/-}$; mCκ$^{-/-}$
Generation 2: (Xenohet × YK2: DI)

yHG1/2$^+$; yK2$^+$; mJ$_H^{+/-}$; mCκ$^{+/-}$ × yHG1/2$^-$; yK2$^+$; mJ$_H^{-/-}$; mCκ$^{-/-}$
Generation 3 (Almost Xenomouse × yK2: DI) or Xenomouse × yK2; DI)

yHG1/2+; yK2$^+$; mJ$_H^{+/-}$; mCκ$^{-/-}$ × yHG1/2$^-$; yK2$^+$; mJ$_H^{-/-}$; mCκ$^{-/-}$
yHG1/2+; yK2$^+$; mJ$_H^{-/-}$; mCκ$^{-/-}$ × yHG1/2$^-$; yK2$^+$; mJ$_H^{-/-}$; mCκ$^{-/-}$

XenoMouse: yHG1/2$^+$; yK2$^+$; mJ$_H^{-/-}$; mCκ$^{-/-}$

The integrity of the human heavy and kappa chain YACs in XenoMouse H2CM strains is confirmed by Southern blot analysis. In all XenoMouse HG1/2M strains analyzed, yHG1/2 is transmitted unaltered through multiple generations with no apparent deletions or rearrangements.

EXAMPLE 23

Flow Cytometry Analysis

To further characterize Xenomouse HG1/2 transgenic mice, peripheral blood and spleen lymphocytes are isolated from 8-10 week old mice and controls. The cells are purified on Lympholyte M (Accurate) (San Diego, Calif.) and treated with purified anti-mouse CD32/CD16 Fc receptor (Pharmingen, 01241D) (San Diego, Calif.) to block non-specific binding to Fc receptors. Next, the cells are stained with various antibodies and analyzed on a FACStar$^{PLUS}$ (Becton Dickinson, CELLQuest software). The panel of antibodies used to stain XenoMouse HG1/2M cells include: Cychrome (Cyc) anti-B220 (Pharmingen, 01128A); fluoroscein isothiocyanate (FITC) anti-human IgM (Pharmingen, 34154X); FITC anti-mouse IgM (Pharmingen, 02204D).

Lymphocytes from four animals from different XenoMouse H2G1/2M strains are evaluated and compared to wild type B6/129 mice using flow cytometry.

Trangenic mice having the yHG1/2 YAC DNA will show significant human antibody and immune system development. Control 129xB6, DI, Xenomouse 2a heterozygous and homozygous are compared to mice heterozygous and homozygous for the yHG1/2 YAC.

EXAMPLE 24

Serum Levels of Human Antibodies in Unimmunized Mice

An ELISA for determination of human antibodies in unimmunized mouse serum is carried out. For more detailed information and procedures on immunoassays see E. Harlow et al., *Antibodies: A Laboratory Manual*, Chapter 14, "Immunoassay", pages 553-614, Cold Spring Harbor Laboratory Press, Cold Spring Harbor, N.Y. (1988). The concentration of human immunoglobulins are determined using the following capture antibodies: mouse anti-human IgM (CGI/ATCC, HB-57) (Manassas, Va.). The detection antibodies used in ELISA experiments are mouse anti-human IgG1-HRP (Southern Biotechnology, 9050-05) (Birmingham, Ala.), mouse anti-human IGM-HRP (Southern Biotechnology, 9020-05) (Birmingham, Ala.). Standards used for quantitation of human Ig are: human IgMκ (Cappel, 13000) (Costa Mesa, Calif.) and human IgG1 (Calbiochem 400126) (San Diego, Calif.).

EXAMPLE 25

Immunization and Hybridoma Generation

Groups of six 8 to 10 weeks old XenoMice yHG1/2 are immunized subcutaneously at the base of the tail (or other route of administration (IP, footpad, etc.) with 10 μg of antigen of choice. The antigen is emulsified in complete Freund's adjuvant for the primary immunization and in incomplete Freund's adjuvant for the additional immunizations. For more detailed information and procedures on animal immunizations see E. Harlow et al., *Antibodies: A Laboratory Manual*, Chapter 5, "Immunizations" pages 53-138, Cold Spring Harbor Laboratory Press, Cold Spring Harbor, N.Y. (1988). Immunizations are carried out at 3-4 week intervals for at least 3 booster immunizations (boosts).

When making monoclonal antibodies, the mice receive a final injection of antigen or cells in PBS four days before the fusion. For more detailed information and procedures on making monoclonal antibodies see E. Harlow et al., *Antibodies: A Laboratory Manual*, Chapter 6, *"Monoclonal Antibodies"*, pages 139-244, Cold Spring Harbor Laboratory Press, Cold Spring Harbor, N.Y. (1988). Lymph node lymphocytes from immunized mice are fused with the non-secretory myeloma NSO cell line [S. Ray, et al., *Proc. Natl. Acad. Sci. USA*, 91:5548-5551 (1994)] or the P3-X63-Ag8.653 myeloma cells and are subjected to HAT selection as previously described [G. Galfre, et al., *Methods Enzymol.* 73:3-46 (1981)].

EXAMPLE 26

Evaluation of Antibody Specifity and Isotype

To determine of whether transgenic mice are producing antigen-specific antibodies, we performed an ELISA. We also determine the human antibody isotype produced. We perform antigen specificity and isotype determinations on antibodies isolated from mouse serum and from hybridoma supernatants as described [Coligan et al., Unit 2.1, "Enzyme-linked immunosorbent assays," in *Current Protocols in Immunology* (1994).], using antigen to capture the antigen-specific antibodies. The concentration of human and mouse immunoglobulins are determined using the following capture antibodies: rabbit anti-human IgG (Southern Biotechnology, 6145-01). The detection antibodies used in ELISA experiments are: mouse anti-human IgG1-HRP (Caltag, MH1015) (Burlingame, Calif.), mouse anti-human IGM-HRP (Southern Biotechnology, 9020-05), and goat anti-human kappa-biotin (Vector, BA-3060). Standards used for quantitation of human and mouse Ig are: human $IgG_1$ (Calbiochem, 400122), human IgMκ (Cappel, 13000), human $IgG_2κ$ (Calbiochem, 400122), mouse IgGκ (Cappel 55939), mouse IgMκ (Sigma, M-3795), and mouse $IgG_4λ$ (Sigma, M-9019).

Transgenic mice produced according to Examples 20-22 above, and immunized with an antigen yield human $IgG_1$ monoclonal antibodies that are antigen specific and of the predicted isotype.

EXAMPLE 27

Introduction of the yHG4 YAC into ES Cells

We introduced the YAC, yHG4, into mouse embryonic stem (ES) cells by yeast spheroplast fusion as described in Example 6. [See B. Birren et al., *Genome Analysis: A Laboratory Manual*, Volume 3, Cloning Systems, Chapter 5: "Introduction of YACs into mammalian cells by spheroplast fusion", pages 548-550, Cold Spring Harbor Laboratory Press, Plainview, N.Y.]. Generally, yHG4 containing yeast cells were spheroplasted using zymolase 20T at 1.5 mg/ml. The yHG4 spheroplasts were fused with HPRT-deficient E 14.TG3B1 mouse ES cells which were cultured as described [see Jakobovits et al., *Nature* 362:255-258 (1993); Green et al., *Nature Genetics* 7:13-21 (1994); E. Robertson in Teratocarcinomas and Embryonic Stem Cells, pages 71-112, IRL, Oxford (1987)] HAT selection was initiated 48 hours after fusion. HPRT-positive ES cell clones were selected. HAT resistant colonies were expanded for genome analysis and were analyzed for YAC integrity by Southern and CHEF blot analyses. Control experiments included "mock" fusions of ES cells alone and yeast spheroplasts alone.

We examined eight ES cell clones derived from ES cell fusion with yHG4-containing yeast using Southern blot with probes spanning the entire insert to determine whether the clones contain all expected EcoRI and BamHI yH2 fragments. We found that the yHG4 YAC was intact in all eight clones. We detected the following human genes in the ES cell genome as part of characterization of the ES cell DNA prior to transgenic mouse generation: all the different $V_H$ families ($V_H1$, $V_H2$, $V_H3$, $V_H4$, $V_H5$, and $V_H6$); human $D_H$, and $J_H$; human $C_\mu$ and $C_\delta$ constant regions; human switch γ2 (hSγ2) and human Cγ4 $C_H$ exons.

EXAMPLE 28

Introduction of ES Cells Containing the yHG4 YAC into Mice

To generate chimeric mice from the YAC yHG4 DNA containing ES cells, we used microinjection of blastocysts followed by breeding. We isolated ES cells containing the YAC yHG4 DNA as described in Example 6, and expanded for the generation of chimeric mice. Next, we microinjected yHG4-bearing ES cell clones into mouse C57Bl/6 blastocysts [See B. Hogan et al., *Manipulating the Mouse Embryo: A Laboratory Manual*, Section D, Introduction of New Genetic Information, *"Injection of Cells into the Blastocyst"* pages 188-196, (1986) (Cold Spring Harbor Laboratory Press, Cold Spring Harbor, N.Y.)]. We identified chimeric offspring by coat color.

Germline transmission was obtained. We identified yHG4 transgenic mice by PCR using primers specific for human V6.

EXAMPLE 29

Breeding Chimeric or Transgenic Mice Containing yHG4 YAC DNA with yK2:DI Mice

To generate mice that produce human antibodies in the absence of endogenous antibodies, yK2-transgenic mice were previously bred with double-inactivated (DI) mouse strains, which are homozygous for gene targeted-inactivated mouse heavy and kappa chain loci and, thus, are deficient in antibody production [see Jakobovits et al., Nature 362:255-258 (1993); Green et al., Nature Genetics 7:13-21 (1994)]. One of the yK2-transgenic mouse strains, J23.1, was bred with DI mice to generate mice hemizygous or homozygous for yK2 YACs on a homozygous inactivated mouse heavy and kappa chain background (yK2;DI). The breeding scheme used to generate a new Xenomouse, which is hemizygous for the yHG4 YAC is shown below. Subsequent breeding of hemizygous XenoMouse males to hemizygous XenoMouse females yields XenoMouse progeny that are homozygous for yHG4 and/or yK2. From these progeny, breeding of males and females, both of which are homozygous for both yHG4 and yK2, will yield a true breeding line of XenoMouseG4.

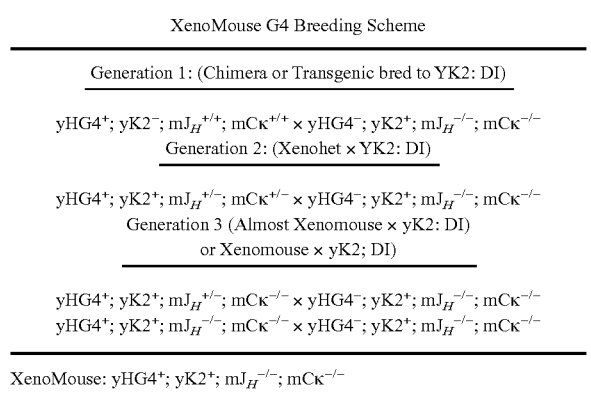

XenoMouse G4 Breeding Scheme

Generation 1: (Chimera or Transgenic bred to YK2: DI)

yHG4$^+$; yK2$^-$; mJ$_H^{+/+}$; mCκ$^{+/+}$ × yHG4$^-$; yK2$^+$; mJ$_H^{-/-}$; mCκ$^{-/-}$

Generation 2: (Xenohet × YK2: DI)

yHG4$^+$; yK2$^+$; mJ$_H^{+/-}$; mCκ$^{+/-}$ × yHG4$^-$; yK2$^+$; mJ$_H^{-/-}$; mCκ$^{-/-}$

Generation 3 (Almost Xenomouse × yK2: DI) or Xenomouse × yK2; DI)

yHG4$^+$; yK2$^+$; mJ$_H^{+/-}$; mCκ$^{-/-}$ × yHG4$^-$; yK2$^+$; mJ$_H^{-/-}$; mCκ$^{-/-}$
yHG4$^+$; yK2$^+$; mJ$_H^{-/-}$; mCκ$^{-/-}$ × yHG4$^-$; yK2$^+$; mJ$_H^{-/-}$; mCκ$^{-/-}$

XenoMouse: yHG4$^+$; yK2$^+$; mJ$_H^{-/-}$; mCκ$^{-/-}$

The integrity of the human heavy and kappa chain YACs in XenoMouse G4 strains was confirmed by Southern blot analysis. In all XenoMouse G4 strains analyzed, yHG4 wass transmitted unaltered through multiple generations with no apparent deletions or rearrangements.

EXAMPLE 30

Flow Cytometry Analysis

To further characterize Xenomouse G4 transgenic mice, peripheral blood and spleen lymphocytes are isolated from 8-10 week old mice and controls. The cells are purified on Lympholyte M (Accurate) (San Diego, Calif.) and treated with purified anti-mouse CD32/CD16 Fc receptor (Pharmingen, 01241D) (San Diego, Calif.) to block non-specific binding to Fc receptors. Next, the cells are stained with various antibodies and analyzed on a FACStar$^{PLUS}$ (Becton Dickinson, CELLQuest software). The panel of antibodies used to stain XenoMouse G4 cells include: Cychrome (Cyc) anti-B220 (Pharmingen, 01128A); fluoroscein isothiocyanate (FITC) anti-human IgM (Pharmingen, 34154X); FITC anti-mouse IgM (Pharmingen, 02204D).

Lymphocytes from four animals from three different XenoMouse G4 strains are evaluated and compared to wild type B6/129 mice using flow cytometry.

Trangenic mice having the G4 YAC DNA will show significant human antibody and immune system development. Control 129xB6, DI, Xenomouse 2a heterozygous and homozygous are compared to mice heterozygous and homozygous for the G4 YAC.

EXAMPLE 31

Serum Levels of Human Antibodies in Unimmunized Mice

An ELISA for determination of human antibodies in unimmunized mouse serum is carried out. For more detailed information and procedures on immunoassays see E. Harlow et al., Antibodies: A Laboratory Manual, Chapter 14, "Immunoassay", pages 553-614, Cold Spring Harbor Laboratory Press, Cold Spring Harbor, N.Y. (1988). The concentration of human immunoglobulins are determined using the following capture antibodies: mouse anti-human IgM (CGI/ATCC, HB-57) (Manassas, Va.). The detection antibodies used in ELISA experiments are mouse anti-human IgG1-HRP (Southern Biotechnology, 9050-05) (Birmingham, Ala.), mouse anti-human IGM-HRP (Southern Biotechnology, 9020-05) (Birmingham, Ala.). Standards used for quantitation of human Ig are: human IgMκ (Cappel, 13000) (Costa Mesa, Calif.) and human IgG1 (Calbiochem 400126) (San Diego, Calif.).

EXAMPLE 32

Immunization and Hybridoma Generation

Groups of six 8 to 10 weeks old XenoMice yHG4 are immunized subcutaneously at the base of the tail or other route of administration (IP, footpad, etc.) with 10 μg of antigen. The antigen is emulsified in complete Freund's adjuvant for the primary immunization and in incomplete Freund's adjuvant for the additional immunizations. For more detailed information and procedures on animal immunizations see E. Harlow et al., Antibodies: A Laboratory Manual, Chapter 5, "Immunizations" pages 53-138, Cold Spring Harbor Laboratory Press, Cold Spring Harbor, N.Y. (1988). Immunizations are carried out at 3-4 week intervals for at least 3 booster immunizations (boosts).

When making monoclonal antibodies, the mice receive a final injection of antigen or cells in PBS four days before the fusion. For more detailed information and procedures on making monoclonal antibodies see E. Harlow et al., Antibodies: A Laboratory Manual, Chapter 6, "Monoclonal Antibodies", pages 139-244, Cold Spring Harbor Laboratory Press, Cold Spring Harbor, N.Y. (1988). Lymph node lymphocytes from immunized mice are fused with the non-secretory myeloma NSO line [S. Ray, et al., Proc. Natl. Acad. Sci. USA, 91:5548-5551 (1994)] or the P3-X63-Ag8.653 myeloma and are subjected to HAT selection as previously described [G. Galfre, et al., Methods Enzymol. 73:3-46 (1981)].

EXAMPLE 33

Evaluation of Antibody Specifity and Isotype

An ELISA for the determination of whether transgenic mice are producing antigen-specific antibodies is performed. It is further desired to confirm the human antibody isotype produced. Antigen specificity and isotype determination are performed on antibodies isolated from mouse serum and from hybridoma supernatants as described [Coligan et al., Unit 2.1, "Enzyme-linked immunosorbent assays," in Current protocols in immunology (1994).] using recombinant antigen to capture the antigen-specific antibodies. The concentration of human and mouse immunoglobulins are determined using the following capture antibodies: rabbit anti-human IgG (Southern Biotechnology, 6145-01). The detection antibodies used in ELISA experiments is mouse anti-human IgG1-HRP (Caltag, MH1015) (Burlingame, Calif.), mouse anti-human IGM-HRP (Southern Biotechnology, 9020-05), and goat anti-human kappa-biotin (Vector, BA-3060). Standards used for quantitation of human and mouse Ig are: human $IgG_1$ (Calbiochem, 400122), human IgMκ (Cappel, 13000), human $IgG_2κ$ (Calbiochem, 400122), mouse IgGκ (Cappel 55939), mouse IgMκ (Sigma, M-3795), and mouse $IgG_4λ$ (Sigma, M-9019).

Transgenic mice produced according to Examples 27-29 above, and immunized with antigen yield human IgG4 monoclonal antibodies that are antigen specific and of the predicted isotype.

Biological Materials:

The following biological materials are disclosed and discussed in connection with the above Examples and are exemplary of materials that can be utilized and prepared in accordance with the present invention:

ppKM1C (yH1C targeting vector)
p1B (targeting vector)
TV1 (mSg1-hCg1 plasmid DNA vector for targeting yH1C to make yH2Bm)
TV4 (mSg1-hCg4 plasmid DNA vector for targeting yH1C to make yH2Cm)
TV G1 (hCg1 plasmid DNA vector for targeting yH1C to make yHG1)
TV G4 (hCg1 plasmid DNA vector for targeting yH1C to make yHG4)
yH2Cm (mSg1-hCg4 YAC) (deposited with the ATCC on Jun. 27, 2000 and having accession number PTA-2161)
yH2Bm (mSg1-hCg1 YAC) (deposited with the ATCC on Jun. 27, 2000 and having accession number PTA-2163)
yHG1 (hSg2-hCg1 YAC)
yHG4 (also referred to as yH3C) (hSg2-hCg4 YAC) (deposited with the ATCC on Jun. 27, 2000 and having accession number PTA-2160)
yH3B (also referred to as yHG1/2) (hSg2-hCg1-hCg2 (TM) YAC) (deposited with the ATCC on Jun. 27, 2000 and having accession number PTA-2162)
ES-yH2Cm clone 1
ES-yH2Cm clone 2
ES-yH2Bm clone 1
ES-yH2Bm clone 2
ES-yH2Bm clone 3
ES-yH2Bm clone 4
ES-yH2Bm clone 5
ES-yH2Bm clone 6
ES-yH2Bm clone 7
ES-yH2Bm clone 8
ES-yH2Bm clone 9

INCORPORATION BY REFERENCE

All references cited herin, including patents, patent applications, papers, text books and the like, and the references cited therein, to the extent that they are not already, are hereby incorporated by reference in their entirety. In addition, the following fererences are also incorporated by reference herein in their entirety, including references cited in such references.

M. J. Mendez et al., "Functional Transplant of Megabase Human Immunoglobulin Loci Recapitulates Human Antibody Response in Mice," *Nature Genetics*, 15:146-156 (1997)

G. T. Williams et al., "Membrane Immunoglobulin Without Sheath or Anchor," *Molecular Immunology*, 30:1427-1432, (1993)

G. T. Williams et al., "The α/β Sheath and Its Cytoplasmic Tyrosine Are Requires For Signaling By The B-cell Antigen Receptor But Not for Capping or For Serine/Threonine-Kinase Recruitment," *Immunology*, 91:474-478 (1994)

A. R. Venkitaraman et al., "The B-cell Antigen Receptor of the Five Immunoglobulin Classes," *Nature*, 352:777-781 (1991)

G. T. Williams et al., "The Sequence of The μ Transmembrane Segment Determines the Tissue Specificity of the Transport of Immunoglobulin M to The Cell Surface," *J. Exp. Med.* 171:947-952 (1990)

S. Pettersson et al., "A Second B cell-specific Enhancer 3' of The Immunoglobulin Heavy-chain Locus," *Nature*, 344: 165-168 (1990)

P. Dariavach et al, "The Mouse IgH 3'-Enhancer," *Eur. J. Immunol.*, 21:1499-1504 (1991)

G. P. Cook et al., "Regulated Activity of the IgH Intron Enhancer (Eμ) in the T Lymphocyte Lineage," *International Immunology*, 7:89-95 (1995)

K. B. Meyer et al., "The IgK 3'-Enhancer Triggers Gene Expression in Early B Lymphocytes but Its Activity is Enhanced on B cell Activation," *International Immunology*, 8:1561-1568 (1996)

M. S. Neuberger et al., "Recombinant Antibodies Possessing Novel Effector Functions," *Nature*, 312:604-608 (1984)

C. I. Bindon et al., "Human Monoclonal IgG Isotypes Differ in Complement Activating Function at the Level of C4 As Well AS C1q," *J. Exp. Med.*, 168:127-142 (1988)

S. Huck et al., "Sequence of a Human Immunoglobulin Gamma 3 Heavy Chain Constant Reguion Gene: Comparison With the Other Human Cγ Genes," *Nucleic Acids Research*, 14: 1779-1789 (1986)

J. Ellison et al., "Nucleotide Sequence of a Human Immunoglobulin $Cγ_4$ Gene," *DNA*, 1: 11-18 (1981)

J. W. Ellison et al., "The Nucleotide Sequence of a Human Immunoglobulin $Cγ_1$ Gene," *Nucleic Acids Research*, 10:4071-4079 (1982)

J. Ellison et al., "Linkage and Sequence Homology of Two Human Immunoglobulin γ Heavy Chain Constant Region Genes," *Immunology*, 79:1984-1988 (1982)

H. Hayashida et al., "Concerted Evolution of the Mouse Immunoglobulin Gamma Chain Genes," *The EMBO Journal*, 3:2047-2053 (1984)

A. Jakobovits et al., "Analysis of Homozygous Mutant Chimeric Mice: Deletion of the Immunoglobulin Heavy-chain Joining Region Blocks B-cell Development and Antibody Production," *Genetics*, 90:2551-2555 (1993)

A. Jakobovits, "The Long-Awaited Magic Bullets: Therapeutic Human Monoclonal Antibodies From Transgenic Mice," *Exp. Opin. Invest. Drugs*, 7:607-614 (1998)

P. T. Jones et al., "Replacing The Complementarity-determining Regions in a Human Antibody with Those From a Mouse," *Nature*, 321:522-525 (1986)

M. S. Neuberger et al., "Isotype Exclusion and Transgene Down-regulation in Immunoglobulin-λ Transgenic Mice," *Nature*, 338:350-352 (1989)

M. Brüggemann et al., (A Repertoire of Monoclonal Antibodies with Human Heavy Chains from Transgenic Mice," *Immunology*, 86:6709-6713 (1989)

C. J. Jolly et al., "Rapid Methods for the Analysis of Immunoglobulin Gene Hypermutation: Application to Transgenic and Gene Targeted Mice," *Nucleic Acids Research*, 25:1913-1919 (1997)

C. J. Jolly et al, "The Targeting of Somatic Hypermutation," *Immunology*, 8:159-168 (1996)

S. Pettersson et al., "Cellular Selection Leads to Age-Dependent and Reversible Down-regulation of Transgenic Immunoglobulin Light Chain Genes," *International Immunology*, 1:509-516 (1989)

K. B. Meyer et al., "The IgK 3'-Enhancer Triggers Gene Expression in Eary B Lymphocytes but its Activity is enhanced on B Cell Activation," *International Immunology*, 8:1561-1568 (1996)

G. P. Cook et al., "Regulated Acticity of the IgH Intron Enhancer (Eµ) in the T Lymphocyte Lineage," *International Immunology*, 7:89-95 (1995)

C. J. Jolly et al., "The Targeting of Somatic Hypermutation," *Immunology*, 8:159-168 (1996)

S. Pettersson et al., "Cellular Selection Leads to Age-dependent and Reversible Down-regulation of Transgenic Immunoglobulin Light Chain Genes," *International Immunology*, 1:509-516 (1989)

L. E. Reid et al., "A Single DNA response element can confer inducibility by both α- and γ-interferon," *Biochemistry*, 86:840-844 (1989)

J. Stavnezer et al., "Immunoglobulin Heavy-chain Switching May be Directed by Prior Induction of Transcripts from Constant-region genes," *Immunology*, 85:7704-7708 (1988)

F. C. Mills et al., "Sequences of Human Immunoglobulin Switch Regions: Implications for Recombination and Transcription," *Nucleic Acids Research*, 18:7305-7316 (1990)

P. Rothman et al., (Structure and Expression of Germline Immunoglobulin γ3 Heavy Chain Gene Transcripts: Implications for Mitogen and Lymphokine Directed class-switching," *International Immunology*, 2:621-627 (1990)

P. Sideras et al., "Production of Sterile Transcripts of Cγ Genes in an IgM-producing Human Neoplastic B Cell Line that Switches to IgG-producing Cells," *International Immunology*, 1:632-642 (1989)

J. P. Manis et al., "Class Switching in B Cells Lacking 3' Immunoglobulin Heavy Chain Enhancers," *J. Exp. Med.*, 188: 1421-1431 (1998)

J. Durdik et al., "Isotype Switching by a Microinjected µ Immunoglobulin Heavy Chain Gene in Transgenic Mice," *Immunology*, 86:2346-2350 (1989)

N. Takahashi et al., "Structure of Human Immunoglobulin Gamma Genes: Implications for Evolution of a Gene Family," *Cell*, 29:671-679 (1982)

J. Zhang et al., "A Selective Defect in IgG2b Switching as a Result of Targeted Mutation of the Iγ2b Promoter and Exon," *The EMBO Journal*, 12:3529-3537: (1993)

S. Jung et al., "Shutdown of Class Switch Recombination by Deletion of a Switch Region Control Element," *Science*, 259: 984-987 (1993)

L. Xu et al., "Replacement of Germ-line ε promoter by Gene Targeting Alters Control of Immunoglobulin Heavy Chain Class Switching," *Immunology*, 90:3705-3709 (1993)

A. Bottaro et al., "S Region Transcription per se Promotes Basal IgE Class Switch Recombination But Additional Factors Regulate the Efficiency of the Process," *The EMBO Journal*, 13:665-674 (1994)

F. C. Mills et al., "Human IgSγ Regions and Their Participation in Sequential Switching to IgE," *The Journal of Immunology*, 155:3021-3036 (1995)

S. C. Li et al., "Expression of Iµ-Cγ Hybrid Germline Transcripts Subsequent to Immunoglobulin Heavy Chain Class Switching," *International Immunology*, 6:491-497 (1994)

Q. Pan et al., "Characterization of Human γ4 Switch Region Polymorphisms Suggess a Meiotic Recombinational Hot Spot Within the Ig Logus: Influence of S Region Length on IgG4 Production," *The Journal of Immunology*, 161:3520-3526 (1998)

T. Honjo et al., "Constant-Region Genes of the Immunoglobulin Heavy Chain and the Molecular Mechanism of Class Switching," *Immunoglobulin Genes*, (1989)

N. Lonberg et al., "Human Antibodies from Transgenic Mice," *Intern. Rev. Immunol.*, 13:65-93 (1995)

G. Pluschke et al., "Generation of Chimeric Monoclonal Antibodies from Mice that Carry Human Immunoglobulin Cγ1 Heavy or Cκ Light Chain Gene Segments," *Journal of Immunological Methods*, 215:27-37 (1998)

M. Brüggemann et al., "The Immunogenicity of Chimeric Antibodies," *J. Exp. Med.*, 170:2153-2157 (1989)

F. A. Harding et al., "Class Switching in Human Immunoglobulin Transgenic Mice," *GenPharm International*, N. Lonberg et al., "Antigen-specific Human Antibodies from Mice Comprising Four Distinct Genetic Modifications," *Nature*, 368:856-859 (1994)

A. Cattaneo et al., "Polymeric Immunoglobulin M is Secreted by Transfectants of Non-lymphoid Cells in the Absence of Immunoglobulin J Chain A. L. Defranco, "The Complexity of Signaling Pathways Activated byt eh BCR," *Current Opinion in Immunology*, 9:296-308 (1997)

V. Arulampalam et al., "The Enhancer Shift: A Model to Explain the Developmental Control of IgH Gene Expression in B-lineage Cells," *Immunology Today*, 18:549-554 (1997)

S. Pettersson et al., "Temporal Control of IgH Gene Expression in Developing B Cells by the 3' Locus Control Region," *Immunobiol.*, 198:236-248 (1997)

K. Kuze et al., "Characterization o the Enhancer Region for Germline Transcription of the Gamma 3 Constant Region Gene of Human Immunoglobulin," *International Immunology*, 3:647-655 (1991)

R. Mocikat et al., "The effect of the Rat Immunoglobulin Heavy-chain 3' Enhancer is position Dependent," *Gene*, 136:349-353 (1993)

P. Dariavach et al., "The Mouse IgH 3'-Enhancer," *Eur. J. Immunol.*, 21:1499-1504 (1991)

J. S. Michaelson et al., "Identification of 3' α-hs4, a Novel Ig Heavy Chain Enhancer Element Regulated at Multiple Stages of B Cell Differentiation," *Nucleic Acids Research*, 23:975-981 (1995)

S. Pettersson et al., "A Second B Cell-specific Enhancer 3' of the Immunoglobulin Heavy-chain Locus," *Nature*, 344: 165-168 (1990)

V. Arulampalam et al., "Elevated Expression Levels of an Ig Transgene in Mice Links the IgH 3' Enhancer to the Regulation of IgH Expression," *International Immunology*, 8:1149-1157 (1996)

S. Delphin et al., "Characterization of an Interleukin 4 (IL-4) Responsive Region in the Immunoglobulin Heavy Chain Germline ε Promoter: Regulation by NF-IL-4, a C/EBP Family Member and Nf-κB/p50,"*J. Exp. Med.*, 181:181-192 (1995)

P. Matthias et al., "The Immunoglobulin Heavy Chain Locus Contains Another B-Cell-Specific 3' Enhancer Close to the α Constant Region," *Molecular and Cellular Biology*, 13:1547-1553 (1993)

R. Lieberson et al., "An Enhancer at the 3' End of the Mouse Immunoglobulin Heavy Chain Locus," *Nucleic Acids Research*, 19:933-937 (1991)

P. Dariavach et al., "The Mouse IgH 3'-Enhancer," *Eur. J. Immunol.*, 21:1499-1504 (1991)

J. S. Michaelson et al., "Regulation of 3' IgH Enhancers by a Common Set of Factor, Including κB-Binding Proteins," *The Journal of Immunology*, 156:2828-2839 (1996)

J. Chen et al., "Mutations of the Intronic IgH Enhancer and its Flanking Sequences Differentially Affect Acccessibility of the $J_H$ Locus, "*The EMBC Journal*, 12:4635-4645 (1993)

M. Cogné et al., "A Class Switch Control Region at the 3' End of the Immunoglobulin Heavy Chain Locus," *Cell*, 77: 737-747 (1994)

S. Huck et al., "Sequence of a Human Immunoglobulin Gamma 3 Heavy Chain Constant Region Gene: Comparison with the Other Human Cγ Genes," *Nucleic Acids Research*, 13:1779-1789 (1986)

J. W. Ellison et al., "The Nucleotide Sequence of a Human Immunoglobulin $Cγ_1$ Gene," *Nucleic Acids Research*, 10:4071-4079 (1982)

J. Ellison et al., "Linkage and Sequence Homology of Two Human Immunoglobulin γ Heavy Chain Constant Region Genes," *Immunology*, 79:1984-1988 (1982)

J. B. Bolen, "Protein Tyrosine Kinases in the Initiation of Antigen Receptor Signaling," *Current Opinion in Immunology*, 7:306-311 (1995)

L. O'Rourke et al., "Co-receptors of B Lymphocytes," *Current Opinion in Immunology*, 9:324-329 (1994)

T. Kurosaki, "Molecular Mechanisms in B Cell Antigen Receptor Signaling," *Current Opinion in Immunology*, 9:309-318 (1997)

B. E. Pearson et al., "Expression of the Human β-amyloid Precursor Protein Gene from a Yeast Artificial Chromosome in Transgenic Mice," *Genetics*, 90:10578-10582 (1993)

J. F. Loring et al., "Rational Design of an Animal Model for Alzheimer's Disease: Introduction of Multiple Human Genomic Transgenes to Reproduce AD Pathology in a Rodent," *Neurobiology of Aging*, 17:173-182 (1996)

J. J. MacQuitty, "The Real Implications of Dolly," *Nature Biotechnology*, 15:294 (1997)

M. T. F. Huang, "Gene Targeting Technology for Creating Transgenic Models of Lymphopoiesis," *Laboratory Animal Science*, 43:156-159 (1993)

J. J. MacQuitty, "GenPharm's Knockout Mice," *Science*, 257: 1188 (1992)

M. T. F. Huang, "T Cell Development in CD3-ς Mutant Mice," *Intern. Rev. Immunol.*, 13:29-41 (1995)

L. D. Taylor et al., "A Transgenic Mouse That Expreses a Diversity of Human Sequence Heavy and Light Chain Immunoglobulins," *Nucleic Acids Research*, 20:6287-6295 (1992)

D. M. Fishwild et al., "High-avidity Human IgGκ Monoclonal Antibodies from a Novel Strain of Minilocus Transgenic Mice," *Nature Biotechnology*, 14:845-851 (1996)

L. D. Taylor et al., "Human Immunoglobulin Transgenes Undergo Rearrangement, Somatic Mutation and Class Switching in Mice that Lack Endogenous IgM," *International Immunology*, 6:579-591 (1994)

N. Tuaillon et al., "Human Immunoglobulin Heavy-chain Minilocus Recombination in Transgenic Mice: Gene-segment Use in μ and γ Transcripts," *Immunology*, 90:3720-3724 (1993)

N. Lonberg et al., "Antigen-specific Human Antibodies from Mice Comprising Four Distinct Genetic Modifications," *Nature*, 368:856-859 (1994)

M. J. Shlomchic et al., "The Role of B Cells in 1pr/1pr-induced Autoimmunity," *J. Exp. Med.*, 180:1295-1306 (1994)

L. Pricop et al., "Antibody Response Elicited by T-dependent and T-independent Antigens in Gene Targeted κ-deficient Mice," *International Immunology*, 6:1839-1847 (1994)

Y. Liu et al., "Gene-targeted B-deficienty Mice Reveal a Critical Role for B Cells in the CD4 T Cell Response," *International Immunology*, 7:1353-1362 (1995)

T. K. Choi et al., "Transgenic Mice Containing a Human Heavy Chain Immunoglobulin Gene Fragment Cloned in a Yeast Artificial Chromosome," *Nature Genetics*, 4:117-123 (1993)

S. D. Wager et al., "Antibody Expression from the Core Region of the Human IgH Locus Reconstructed in Transgenic Mice Using Bacteriophage P1 Clones," *Genomics*, 35:405-414 (1996)

S. D. Wagner et al., "The Diversity of Antigen-specific Monoclonal Antibodies from Transgenic Mice Bearing Human Immunoglobulin Gene Miniloci," *Dur. J. Immunol.*, 24:2672-2681 (1994)

S. D. Wagner et al., "Antibodies Generalted from human Immunoglobulin Miniloci in Transgenic Mice," *Nucleic Acids Research*, 22:1389-1393 (1994)

N. P. Davies et al., "Creation of Mice Expressing Human Antibody Light Chains by Introduction of a Yeast Artificial Chromosome Containing the Core Region of the Human Immunoglobulin κ Locus," *Bio/Technology*, 11:91-914 (1993)

F. D. Batista et al., "Affinity Dependence of the B Cell Response to Antigen: A Threshold, a Ceiling, and the Importance of Off-Rate," *Immunity*, 8:751-759 (1998)

M. R. Ehrenstein et al., "Targeted Gene Disruption Reveals a Role for Natural Secretory IgM in the Maturation of the Primary Immune Response," *Immunology*, 95:10089-10093 (1998)

C. Milstein et al., "Both DNA Strands of Antibody Genes are Hypermutation Targets," *Immunology*, 95:8791-8794 (1998)

J. E. Sale et al., "TdT-Accessible Breaks Are Scattered over the Immunoglobulin V Domain in a Constitutively Hypermutating B Cell Line," *Immunity*, 9:859-869 (1998)

M. S. Neuberger, "Antigen Receptor Signaling Gives Lymphocytes a Long Life," *Cell*, 90:971:973 (1997)

B. Goyenechea et al., "Cells Strongly Expressing Igκ Transgenes Show Clonal Recruitment of Hypermutation: A Role for Both MAR and the Enhancers," *The EMBO Journal*, 16:3987-3994 (1997)

Y. M. The et al., "The Immunoglobulin (Ig)α and Igβ Cytoplasmic Domains Are Independently Sufficient to Signal B Cell Maturation and Activation in Transgenic Mice," *J. Exp. Med.*, 185:1753-1758 (1997)

J. Yélamos et al., "Targeting of Non-Ig Sequences in Place of the V Segment by Somatic Hypermutation," *Nature*, 376: 225-229 (1995)

S. D. Wagner et al., "Codon bias Targets Mutation," *Nature*, 376:732 (1995)

N. Klix et al., "Multiple Sequences from Downstream of the Jκ Cluster Can Combine to Recruit Somatic Hypermutation to a Heterologous, Upstream Mutation Domain," *Eur. J. Immunol.*, 28:317-326 (1996)

M. Neuberger et al., "Mice Perform a Human Repertoire," *Nature*, 386:25-26 (1997)

N. P. Davies et al., "Targeted Alterations in Yeast Artificial Chromosomes for Inter-species Gene Transfer," *Nucleic Acids Research*, 20:2693-2698 (1992)

M. Brüggemann et al., "Strategies for Expressing Human Antibody Repertoires in Transgenic Mice," *Immunology Today*, 17:391-397 (1996)

X. Zou et al., "Dominant Expression of a 1.3 Mb Human IgK Locus Replacing Mouse Light Chain Production," *The FASEB Journal*, 10:1227-1232 (1996)

I. K. Jarmer et al., "Chimaeric Monoclonal Antibodies Encoded by the Human $V_H{}^{26}$ Gene From Naïve Transgenic Mice Display a Wide Range of Antigen-binding Specificities," *Immunology*, 88:174-182 (1996)

X. Zou et al., "Subtle Differences in Antibody Responses and Hypermutation of λ Light Chains in Mice with a Disrupted χ Constant Region," *Eur. J. Immunol.*, 25:2154-2162 (1995)

A. V. Popov et al., "Yeast Colony Size Reflects YAC Copy Number," *Nucleic Acids Rsearch*, "25:2039-2040 (1997)

N. P. Davies et al., "Extension of Yeast Artificial Chromosomes by Cosmid Multimers," *Nucleic Acids Research*, 21:767-768 (1993)

C. Bützler et al., "Rapid Induction of B-cell Lymphomas in Mice Carrying a Human IgH/c-MYCYAC," *Oncogene*, 14:1383-1388 (1997)

A. V. Popov et al., "Assembly and Extension of Yeast Artificial Chromosomes to Build Up a Large Locus," *Gene*, 177:195-201 (1996)

H. Waldmann et al., "Monoclonal Antibodies for Immunosuppression," *Monoclonal Antibody Therapy Prog Allergy*, 45:16-30 (1988)

M. Brüggemann et al., "Designer Mice: The Production of Human Antibody Repertoires in Transgenic Animals," *generation of Antibodies by Cell and Gene Immortalization*, 7:33-40 (1993)

A. G. Betz et al., "Discriminating Intrinsic and Antigen-selected Mutational hotspots in Immunoglobulin V Genes," *Immunology Today*, 14:405-409

M. Brüggemann et al, "Construction, Function and Immunogenicity of Recombinant Monoclonal Antibodies," *Behring, Inst. Mitt.*, 87:21-14 (1990)

M. Brüggemann et al., "Production of Human Antibody Repertoires in Transgenic Mice," *Current Opinion in Biotechnology*, 8:455-458 (1997)

K. B. Meyer et al., "The Immunoglobulin χ Locus Contains a Second, Stronger B-cell-specific Enhancer Which is Located Downstream of the Constant Region," *The EMBO Journal*, 8:1959-1964 (1989)

M. Brüggemann et al., "Sequence of a Rate Immunoglobulin $γ_{2c}$ Heavy Chain Constant Region cDNA: Extensive Homology to Mouse $γ_3$, *Eur. J. Immunol.*, 18:317-319 (1988)

M. Brüggemann et al., "Human Antibody Production in Transgenic Mice: Expression fro 100 kb of the Human IgH Locus," *Eur. J. Immunol.*, 21:1323-1326 (1991)

M. Brüggemann, "Evolution of the Rate Immunoglobulin Gamma Heavy-chain Gene Family," *Gene*, 74:473-482 (1988)

R. Sitia et al., "Regulation of Membrane IgM Expression in Secretory B Cells: Translational and Post-transnational Events," *The EMBO Journal*, 6:3969-3977 (1987)

M. J. Sharpe et al., "Somatic Hypermutation of Immunoglobulin χ may depend on Sequences 3' of Cχ and Occurs on Passenger Transgenes," *The EMBO Journal*, 10:2139-2145 (1991)

S. Biocca et al., "Expression and Targeting of Intracellular Antibodies in Mammalian Cells," *The EMBO Journal*, 9:101-108 (1990)

K. J. Patel et al., "Antigen Presentation by the B Cell Antigen Receptor Is Driven by the α/β Sheath and Occurs Independently of Its Cytoplasmic Tyrosines," *Cell*, 74:939-946 (1993)

K. B. Meyer et al., "The Improtance of the 3'-Enhancer Region in Immunoglobulin χ Gene Expression," *Nucleic Acids Research*, 18:5609-56115 (1990)

A. G. Betz et al., "Elements Regulating Somatic Hypermutation of an Immunoglobulin κ Gene: Critical Role for the Intron Enhancer/Matrix Attachment Region," *Cell*, 77:239-248 (1994)

J. O. Mason et al, "Transcription Cell Type Specificity Is Conferred by an Immunoglobulin $V_H$ Gene Promoter That Includes a Functional Consensus Sequence," *Cell*, 41:479-487 (1985)

M. S. Neuberger et al., "Activation of Mouse Complement by Monoclonal Mouse Antibodies," *Eur. J. Immunol.*, 11:1012-1016 (1981)

M. R. Walker et al., "Interaction of Human IgG Chimeric Antibodies with the Human FcRI and FcRII Receptors: Requirements for Antibody-Mediated Host Cell-Target Cell Interaction," *Molecular Immunology*, 26:403-411 (1989)

M. Brüggemann et al, "Comparison of the Effector Functions of Human Immunoglobulins Using a Mastched Set of Chimeric Antibodies," *J. Exp. Med.* 166:1351-1361 (1987)

R. Sherman-Gold, "Monoclonal Antibodies: The Evolution from '80s Magic Bullets to Mature, Mainstream Applications as Clinical Therapeutics," *Genetic Engineering News*, 17 (1997)

We claim:

1. A transgenic mouse and its progeny, wherein the somatic and germ cells comprise a heavy chain transgene comprising a DNA fragment comprising a DNA sequence of a human D segment gene, a human heavy chain J segment gene and a human heavy chain constant region gene Cμ, wherein said DNA fragment is operably linked to at least one human heavy chain V segment gene, and wherein said DNA fragment further is operably linked to an additional constant region gene, said additional constant region gene comprising a human switch region, human CH1, $C_{hinge}$, CH2 and CH3 exons and human membrane exons, wherein said human switch region and said human membrane exons are from the same isotype and the human CH1, $C_{hinge}$, CH2 and CH3 exons are from a different isotype than said human switch region and said human membrane exons.

2. The transgenic mouse and progeny according to claim 1, further comprising a human immunoglobulin kappa light chain transgene.

3. The transgenic mouse and progeny according to claim 1 or 2, further comprising inactivated endogenous immunoglobulin heavy and kappa light chain loci.

4. A method for producing the transgenic mouse and its progeny according to claim 2 and that produces high affinity, fully human antibodies of a desired isotype specific for an antigen of interest following immunization with the antigen of interest, comprising:

(a) introducing said heavy chain transgene into a mouse embryonic stem cell;

(b) producing from the embryonic stem cell a transgenic mouse whose somatic and germ cells comprise said heavy chain transgene; and (c) breeding said transgenic mouse comprising said heavy chain transgene with a transgenic mouse whose somatic and germ cells comprise a human kappa light chain transgene to produce a transgenic mouse and its progeny that produces high affinity, fully human antibodies of a desired isotype specific for an antigen of interest following immunization with the antigen of interest.

5. A method for producing a high-affinity, fully human antibody of a desired isotype, wherein said antibody is specific for an antigen of interest, comprising contacting the transgenic mouse according to claim 2 with the antigen of interest to induce antibody production in the B-cells of said mouse and collecting said human antibody.

6. The method according to claim 5, wherein the antibody is collected from the blood stream of said transgenic mouse.

7. The method according to claim 5, further comprising 1) harvesting a B-cell from said mouse, and 2) collecting an antibody from said B-cell.

8. The method according to claim 5, further comprising 1) harvesting a B-cell from said mouse, 2) transfecting a host cell with DNA isolated from said B-cell, wherein said DNA comprises a rearranged heavy chain and a rearranged light chain, and 3) collecting an antibody from said host cell.

9. A transgenic mouse and its progeny, wherein the somatic and germ cells comprise a heavy chain transgene comprising a DNA fragment comprising a DNA sequence of a human D segment gene, a human heavy chain J segment gene and a human heavy chain constant region gene Cµ, wherein said DNA fragment is operably linked to at least one human heavy chain V segment gene, and wherein said DNA fragment further is operably linked to an additional constant region gene, said additional constant region gene comprising (1) a human switch region; (2) a region comprising human CH1, $C_{hinge}$, CH2 and CH3 exons; and (3) human membrane exons, wherein said human switch region, said region comprising human CH1, $C_{hinge}$, CH2 and CH3 exons, and said human membrane exons are from three different isotypes.

10. The transgenic mouse and progeny according to claim 9, further comprising a human immunoglobulin kappa light chain transgene.

11. The transgenic mouse and progeny according to claim 9 or 10, further comprising inactivated endogenous immunoglobulin heavy and kappa light chain loci.

12. A transgenic mouse and its progeny, wherein the somatic and germ cells comprise a heavy chain transgene comprising a DNA fragment comprising a DNA sequence of a human D segment gene, a human heavy chain J segment gene and a human heavy chain constant region gene Cµ, wherein said DNA fragment is operably linked to at least one human heavy chain V segment gene, and wherein said DNA fragment further is operably linked to an additional constant region gene, said additional constant region gene comprising a human switch region, human CH1, $C_{hinge}$, CH2 and CH3 exons and human membrane exons, wherein said human switch region and said human CH1, $C_{hinge}$, CH2 and CH3 exons are from the same isotype and said human membrane exons are from a different isotype than said human switch region and said human CH1, $C_{hinge}$, CH2 and CH3 exons.

13. The transgenic mouse and progeny according to claim 12, further comprising a human immunoglobulin kappa light chain transgene.

14. The transgenic mouse and progeny according to claim 12 or 13, further comprising inactivated endogenous immunoglobulin heavy and kappa light chain loci.

15. A method for producing the transgenic mouse and its progeny according to claim 10 and that produces high affinity, fully human antibodies of a desired isotype specific for an antigen of interest following immunization with the antigen of interest, comprising:

(a) introducing said heavy chain transgene into a mouse embryonic stem cell;

(b) producing from the embryonic stem cell a transgenic mouse whose somatic and germ cells comprise said heavy chain transgene; and (c) breeding said transgenic mouse comprising said heavy chain transgene with a transgenic mouse whose somatic and germ cells comprise a human kappa light chain transgene to produce a transgenic mouse and its progeny that produces high affinity, fully human antibodies of a desired isotype specific for an antigen of interest following immunization with the antigen of interest.

16. A method for producing a high-affinity, fully human antibody of a desired isotype, wherein said antibody is specific for an antigen of interest, comprising contacting the transgenic mouse according to claim 10 with the antigen of interest to induce antibody production in the B-cells of said mouse and collecting said human antibody.

17. The method according to claim 16, wherein the antibody is collected from the blood stream of said transgenic mouse.

18. The method according to claim 16, further comprising 1) harvesting a B-cell from said mouse, and 2) collecting an antibody from said B-cell.

19. The method according to claim 16, further comprising 1) harvesting a B-cell from said mouse, 2) transfecting a host cell with DNA isolated from said B-cell, wherein said DNA comprises a rearranged heavy chain and a rearranged light chain, and 3) collecting an antibody from said host cell.

20. The method of claim 18, wherein the B-cell has been immortalized.

21. A method for producing the transgenic mouse and its progeny according to claim 13 and that produces high affinity, fully human antibodies of a desired isotype specific for an antigen of interest following immunization with the antigen of interest, comprising:

(a) introducing said heavy chain transgene into a mouse embryonic stem cell;

(b) producing from the embryonic stem cell a transgenic mouse whose somatic and germ cells comprise said heavy chain transgene; and (c) breeding said transgenic mouse comprising said heavy chain transgene with a transgenic mouse whose somatic and germ cells comprise a human kappa light chain transgene to produce a transgenic mouse and its progeny that produces high affinity, fully human antibodies of a desired isotype specific for an antigen of interest following immunization with the antigen of interest.

22. A method for producing a high-affinity, fully human antibody of a desired isotype, wherein said antibody is specific for an antigen of interest, comprising contacting the transgenicmouse according to claim 13 with the antigen of interest to induce antibody production in the B-cells of said mouse and collecting said human antibody.

23. The method according to claim 22, wherein the antibody is collected from the blood stream of said transgenic mouse.

24. The method according to claim 22, further comprising 1) harvesting a B-cell from said mouse, and 2) collecting an antibody from said B-cell.

25. The method according to claim 22, further comprising 1) harvesting a B-cell from said mouse, 2) transfecting a host cell with DNA isolated from said B-cell, wherein said DNA comprises a rearranged heavy chain and a rearranged light chain, and 3) collecting an antibody from said host cell.

26. The method of claim 24, wherein the B-cell has been immortalized.

* * * * *

UNITED STATES PATENT AND TRADEMARK OFFICE
CERTIFICATE OF CORRECTION

PATENT NO. : 7,547,817 B2  Page 1 of 1
APPLICATION NO. : 11/223359
DATED : June 16, 2009
INVENTOR(S) : Green et al.

It is certified that error appears in the above-identified patent and that said Letters Patent is hereby corrected as shown below:

Col. 74, add claim: --27. The method of claim 7, wherein the B-cell has been immortalized.--

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,547,817 B2  Page 1 of 1
APPLICATION NO. : 11/223359
DATED : June 16, 2009
INVENTOR(S) : Green et al.

It is certified that error appears in the above-identified patent and that said Letters Patent is hereby corrected as shown below:

Col. 74, line 3, add claim: --27. The method of claim 7, wherein the B-cell has been immortalized.--

This certificate supersedes the Certificate of Correction issued September 15, 2009.

Signed and Sealed this

Sixth Day of October, 2009

David J. Kappos
*Director of the United States Patent and Trademark Office*